United States Patent
Athey et al.

(10) Patent No.: US 10,553,318 B2
(45) Date of Patent: *Feb. 4, 2020

(54) INDIVIDUAL AND COHORT PHARMACOLOGICAL PHENOTYPE PREDICTION PLATFORM

(71) Applicant: THE REGENTS OF THE UNIVERSITY OF MICHIGAN, Ann Arbor, MI (US)

(72) Inventors: Brian D. Athey, Ann Arbor, MI (US); Ari Allyn-Feuer, Ann Arbor, MI (US); Gerald A. Higgins, Ann Arbor, MI (US); James S. Burns, Ann Arbor, MI (US); Alexandr Kalinin, Ann Arbor, MI (US); Brian Pauls, Ann Arbor, MI (US); Alex Ade, Ann Arbor, MI (US); Narathip Reamaroon, Ann Arbor, MI (US)

(73) Assignee: THE REGENTS OF THE UNIVERSITY OF MICHIGAN, Ann Arbor, MI (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/267,546

(22) Filed: Feb. 5, 2019

(65) Prior Publication Data
US 2019/0172584 A1    Jun. 6, 2019

Related U.S. Application Data

(63) Continuation of application No. 15/977,347, filed on May 11, 2018, now Pat. No. 10,249,389.
(Continued)

(51) Int. Cl.
*G16H 50/20* (2018.01)
*G16H 50/30* (2018.01)
(Continued)

(52) U.S. Cl.
CPC ............. *G16H 50/20* (2018.01); *A61K 31/37* (2013.01); *G06N 3/08* (2013.01); *G16B 20/00* (2019.02);
(Continued)

(58) Field of Classification Search
CPC ........ G16H 50/20; G16H 10/60; G16H 50/30; G16H 50/70
(Continued)

(56) References Cited

U.S. PATENT DOCUMENTS 9,111,028 B2    8/2015  Mrazek et al.
10,249,389 B2*  4/2019  Athey .................... G16B 20/00
(Continued)

FOREIGN PATENT DOCUMENTS

WO    WO-2013022995 A2    2/2013

OTHER PUBLICATIONS

Allyn-Feuer et al., "The pharmacoepigenomics informatics pipeline defines a pathway of novel and known warfarin pharmacogenomics variants," Pharmacogenomics, vol. 19, No. 5 (Feb. 5, 2018).
(Continued)

*Primary Examiner* — Daryl C Pope
(74) *Attorney, Agent, or Firm* — Marshall, Gerstein & Borun LLP

(57) ABSTRACT

For patients who exhibit or may exhibit primary or comorbid disease, pharmacological phenotypes may be predicted through the collection of panomic data over a period of time. A machine learning engine may generate a statistical model based on training data from training patients to predict pharmacological phenotypes, including drug response and dosing, drug adverse events, disease and comorbid disease risk, drug-gene, drug-drug, and polypharmacy interactions. Then the model may be applied to data for new patients to predict their pharmacological phenotypes, and enable deci-
(Continued)

sion making in clinical and research contexts, including drug selection and dosage, changes in drug regimens, polypharmacy optimization, monitoring, etc., to benefit from additional predictive power, resulting in adverse event and substance abuse avoidance, improved drug response, better patient outcomes, lower treatment costs, public health benefits, and increases in the effectiveness of research in pharmacology and other biomedical fields.

20 Claims, 15 Drawing Sheets

Related U.S. Application Data

(60) Provisional application No. 62/633,355, filed on Feb. 21, 2018, provisional application No. 62/505,422, filed on May 12, 2017.

(51) Int. Cl.
- G16H 10/60 (2018.01)
- A61K 31/37 (2006.01)
- G06N 3/08 (2006.01)
- G16H 50/70 (2018.01)
- G16B 30/00 (2019.01)
- G16B 40/00 (2019.01)
- G16B 20/00 (2019.01)

(52) U.S. Cl.
CPC ............ *G16B 30/00* (2019.02); *G16B 40/00* (2019.02); *G16H 10/60* (2018.01); *G16H 50/30* (2018.01); *G16H 50/70* (2018.01)

(58) Field of Classification Search
USPC ............ 340/506, 3.1, 539.1, 539.11, 539.13, 340/539.12, 573.1
See application file for complete search history.

(56) References Cited

U.S. PATENT DOCUMENTS

| | | |
|---|---|---|
| 2011/0183924 A1 | 7/2011 | Mintz et al. |
| 2014/0038836 A1 | 2/2014 | Higgins et al. |
| 2014/0046696 A1 | 2/2014 | Higgins et al. |
| 2014/0222349 A1 | 8/2014 | Higgins et al. |
| 2015/0347699 A1 | 12/2015 | Vidwans et al. |

OTHER PUBLICATIONS

Search Report and Written Opinion for International application No. PCT/US2018/032179, dated Aug. 21, 2018.
Office Action for U.S. Appl. No. 15/977,347, dated Oct. 5, 2018.

\* cited by examiner

INDIVIDUAL AND COHORT PHARMACOLOGICAL PHENOTYPE PREDICTION PLATFORM

CROSS-REFERENCE TO RELATED APPLICATIONS

This application is a continuation of and claims priority to U.S. application Ser. No. 15/977,347, filed on May 11, 2018, entitled "Individual and Cohort Pharmacological Phenotype Prediction Platform," which claims priority to and the benefit of the filing date of (1) provisional U.S. Application Ser. No. 62/505,422, filed on May 12, 2017, entitled "Individual and Cohort Pharmacological Phenotype Prediction Platform," and (2) provisional U.S. Application Ser. No. 62/633,355, filed on Feb. 21, 2018, entitled "Individual and Cohort Pharmacological Phenotype Prediction Platform," the entire disclosures of each of which is hereby expressly incorporated by reference herein.

FIELD OF THE INVENTION

The present application relates to pharmacological patient phenotypes and, more specifically, to a method and system for utilizing machine learning and statistical techniques to predict drug response phenotypes for patients, and stratified cohorts of patients, based on their biological, ancestry, demographic, clinical, sociological, and environmental characteristics.

BACKGROUND

Today, drug response for some patients may be predicted based on a patient's coding genome. Specific genetic traits may be mapped to a particular response to a drug and a drug may be selected for a patient based on the patient's predicted response.

However, noncoding genomic variants account for the vast majority of genetic differences for traits such as drug response, adverse drug response, and disease risk in patients. The convergence of epigenomic regulation research and genome wide association studies (GWAS) has also shown that epigenomic alterations may be indicators of disease risk, drug response, and adverse drug response in both human and animals, in a broad set of medical specialties and pharmacological research settings. Moreover, disease-related phenotype variation may be dictated by differences in chromatin state which had previously been attributed to genetic differences.

Current systems do not utilize chromatin state, genomic regulatory elements, epigenomics, proteomics, metabolomics, or transcriptomics to predict pharmacological phenotypes for patients. Current systems also do not factor in environmental and sociological characteristics that may alter genetic traits for determining the pharmacological phenotypes. Additionally, such systems do not utilize machine learning techniques to train the systems to adapt to changes in biological characteristics and/or pharmacological phenotypes corresponding to the biological characteristics over time.

Accordingly, there is a need for a system that accurately predicts pharmacological phenotypes including pharmacological response, disease risk, substance abuse or other pharmacological phenotypes based on panomic characteristics including genomics, epigenomics, chromatin state, proteomics, metabolomics, transcriptomics, etc., and sociological and environmental characteristics of a patient in near real-time.

SUMMARY

To predict pharmacological phenotypes for a patient, a pharmacological phenotype prediction system may be trained using various machine learning techniques. More specifically, the pharmacological phenotype prediction system may be trained to analyze a patient's panomic, sociological, and environmental data to predict the patient's response to various drugs, a likelihood of substance abuse for the patient, a risk of various illnesses, or any other pharmacological phenotype for the patient. The pharmacological phenotype prediction system may be trained by obtaining panomic, sociological, and environmental data (also referred to herein as "training data") for a group of patients (also referred to herein as "training patients").

In some embodiments, the sociological and environmental data for a patient may be obtained at several points in time to capture a detailed account of the patient's experiences. For each of the training patients, the pharmacological phenotype prediction system may obtain pharmacological phenotypes for the patient as training data, such as whether the patient suffers from substance abuse problems, the patient's chronic illnesses, the patient's responses to various drugs prescribed to the patient, etc. The training data may be analyzed using the various machine learning techniques to generate a statistical model which may be used to predict a patient's response to various drugs, a likelihood of substance abuse for the patient, a risk of various illnesses, or any other pharmacological phenotype for the patient. For example, the statistical model may be a neural network generated based on a combination of a network analysis of gene regulatory networks and environmental impacts on gene expression.

After the training period, the pharmacological phenotype prediction system may receive panomic, sociological, and environmental data, collected at several points in time, for a patient whose pharmacological phenotypes are unknown (e.g., the patient has not yet been prescribed lithium for bipolar disorder and therefore the patient's response to lithium is unknown). The panomic, sociological, and environmental data may be applied to the statistical model to predict pharmacological phenotypes for the patient, which may be displayed on a health care provider's client device.

For example, for a particular drug, the pharmacological phenotype prediction system may determine a likelihood that the patient will have an adverse drug reaction. Additionally, the pharmacological phenotype prediction system may generate an indicator of the predicted efficacy or appropriate dose of the drug for the patient. In some embodiments, the likelihood that the patient will have an adverse drug reaction may be compared to a threshold likelihood and the predicted efficacy may be compared to a threshold efficacy. When the likelihood exceeds the threshold likelihood, the predicted efficacy is less than the threshold efficacy, and/or a combination of the likelihood of an adverse drug reaction and predicted efficacy exceeds a threshold, an indication of the likelihood and/or the efficacy for the drug may be provided to the health care provider. Accordingly, the health care provider may alter the dose, not prescribe the drug to the patient, or suggest an alternate drug of higher efficacy for the patient.

In this manner, the pharmacological phenotype prediction system may identify an optimal drug for a patient corresponding to a particular illness. For example, for a particular illness, the pharmacological phenotype prediction system may select one of several drugs designed to treat the illness having a maximum predicted efficacy for the patient and a minimum likelihood and/or severity of an adverse drug reaction. The present embodiments advantageously allow health care providers to accurately and efficiently identify optimal drugs to recommend and prescribe to patients. Additionally, by incorporating panomic, sociological, and environmental data to generate the statistical model, the present embodiments advantageously include a comprehensive bioinformatics analysis of patients' biological characteristics that may be altered over time. This comprehensive bioinformatics analysis allows for a more accurate prediction system that not only predicts pharmacological phenotypes based on inherent traits of a patient, but also incorporates sociological and environmental traits which are constantly changing over time and may alter the expression of genetic traits.

Moreover, by generating a statistical model that accurately predicts disease risk and a likelihood of adverse drug reactions, the health care provider may proactively address these issues before the patient exhibits symptoms of the illness or begins to suffer from substance abuse problems or other disease symptoms.

In an embodiment, a computer-implemented method for identifying pharmacological phenotypes is provided. The method includes identifying a plurality of single nucleotide polymorphisms (SNPs) correlated with a particular set of pharmacological phenotypes, comparing the plurality of SNPs to a database of SNPs to identify additional SNPs that are linked to the plurality of SNPs, wherein the plurality of SNPs and additional SNPs are included in a set of permissive candidate variants, performing a bioinformatics analysis to filter the set of permissive candidate variants into a subset of intermediate candidate variants based on at least one of: regulatory function, variant dependence, a presence of target gene relationships for the permissive candidate variants, or whether the permissive candidate variants are non-synonymous coding variants with a minor allele frequency, and performing a network analysis to filter the subset of intermediate candidate variants into candidate variants of SNPs, genes associated with the SNPs, or networks associated with the SNPs which are causally related to the particular set of pharmacological phenotypes. The method further includes obtaining a biological sample of a patient, comparing the biological sample to the SNPs which are causally related to the particular set of pharmacological phenotypes, and providing an indication of one or more pharmacological phenotypes for the patient for display to a health care provider based on the comparison.

In another embodiment, a computing device for identifying pharmacological phenotypes is provided. The computing device includes a communication network, one or more processors, and a non-transitory computer-readable memory coupled to the one or more processors and storing instructions thereon. When executed by the one or more processors, the instructions cause the system to identify a plurality of single nucleotide polymorphisms (SNPs) correlated with a particular set of pharmacological phenotypes, compare the plurality of SNPs to a database of SNPs to identify additional SNPs that are linked to the plurality of SNPs, wherein the plurality of SNPs and additional SNPs are included in a set of permissive candidate variants, perform a bioinformatics analysis to filter the set of permissive candidate variants into a subset of intermediate candidate variants based on at least one of: regulatory function, variant dependence, a presence of target gene relationships for the permissive candidate variants, or whether the permissive candidate variants are non-synonymous coding variants with a minor allele frequency, and perform a network analysis to filter the subset of intermediate candidate variants into candidate variants of SNPs, genes associated with the SNPs, or networks associated with the SNPs which are causally related to the particular set of pharmacological phenotypes. The instructions further cause the computing device to obtain a biological sample of a patient, compare the biological sample to the SNPs which are causally related to the particular set of pharmacological phenotypes, and provide, via the communication network, an indication of one or more pharmacological phenotypes for the patient for display to a health care provider based on the comparison.

DETAILED DESCRIPTION

Figure 1A:
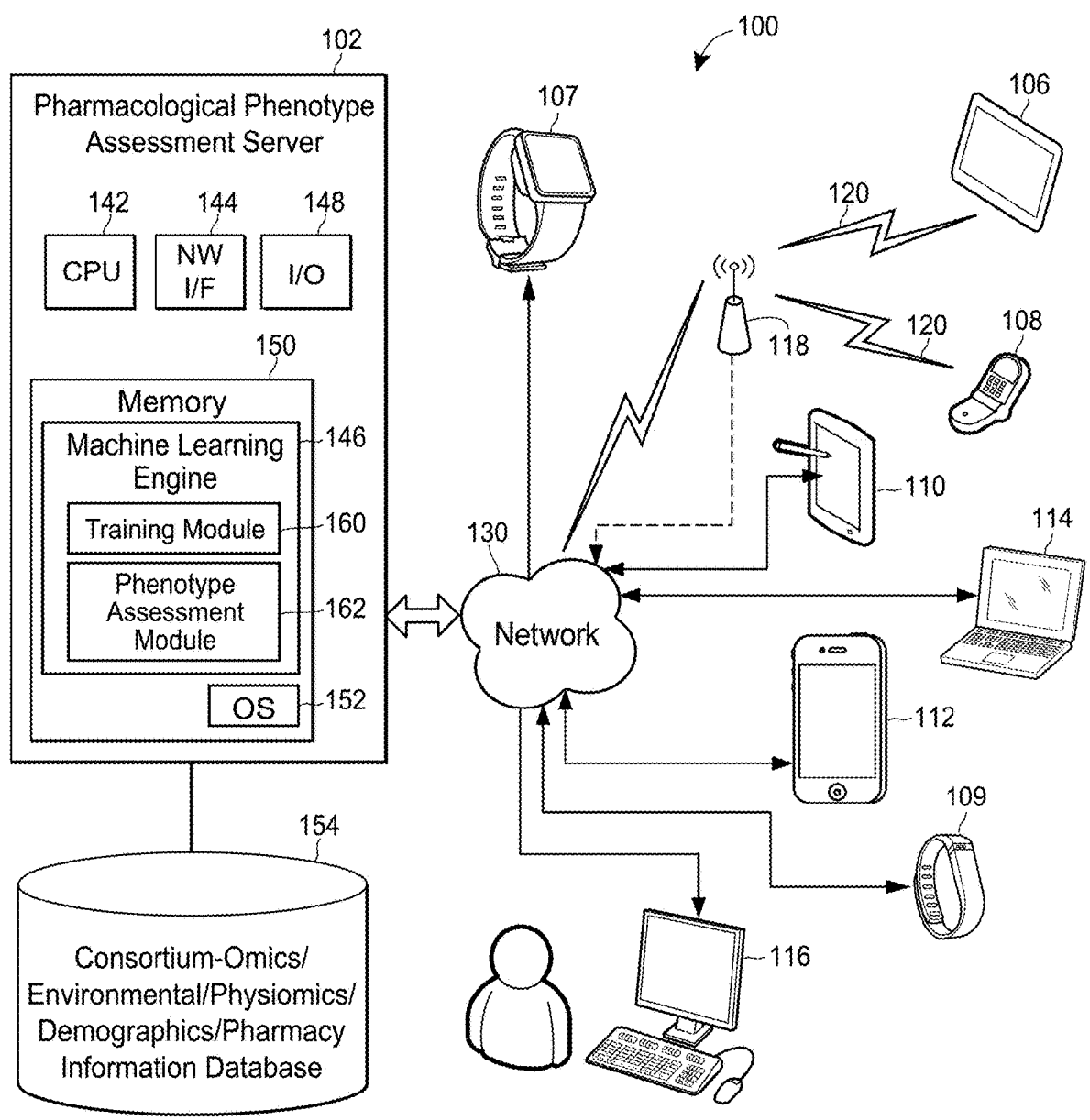
FIG. 1A illustrates a block diagram of a computer network and system on which an exemplary pharmacological phenotype prediction system may operate in accordance with the presently described embodiments.

Although the following text sets forth a detailed description of numerous different embodiments, it should be understood that the legal scope of the description is defined by the words of the claims set forth at the end of this disclosure. The detailed description is to be construed as exemplary only and does not describe every possible embodiment since describing every possible embodiment would be impractical, if not impossible. Numerous alternative embodiments could be implemented, using either current technology or technology developed after the filing date of this patent, which would still fall within the scope of the claims.

It should also be understood that, unless a term is expressly defined in this patent using the sentence "As used herein, the term '_____' is hereby defined to mean . . . " or a similar sentence, there is no intent to limit the meaning of that term, either expressly or by implication, beyond its plain or ordinary meaning, and such term should not be interpreted to be limited in scope based on any statement made in any section of this patent (other than the language of the claims). To the extent that any term recited in the claims at the end of this patent is referred to in this patent in a manner consistent with a single meaning, that is done for sake of clarity only so as to not confuse the reader, and it is not intended that such claim term be limited, by implication or otherwise, to that single meaning. Finally, unless a claim element is defined by reciting the word "means" and a function without the recital of any structure, it is not intended that the scope of any claim element be interpreted based on the application of 35 U.S.C. § 112, sixth paragraph.

Accordingly, as used herein, the term "health care provider" may refer to any provider of medical or health services. For example, a health care provider may be a physician, clinician, nurse practitioner, physician assistant, an insurer, a pharmacist, a hospital, a clinical facility, a pharmacy technician, a pharmaceutical company, a research scientist, other medical organization or medical professional licensed to prescribe medical products and medicaments to patients, etc.

As used herein, the term "patient" may refer to any human or other organism, or combination thereof, whose health, longevity, or other medical outcomes is the object of clinical or research interest, investigation, or effort.

Additionally, as used herein, the term "panomics" may refer to a range of molecular biology technologies related to the interaction of biological functions within a cell and with other functions within the human body. For example, panomics may include genomics, epigenomics, chromatin state, transcriptomics, proteomics, metabolomics, biological networks and systems models, etc. Panomic data may be specific to various point in time and to specific tissues and linages of cells, so that panomic data collection is connected to these features and may also be collected and used for a plurality of tissues, lineages, and temporal points connected to phenotypes of interest for a patient. A patient's panomics may relate to biomarkers for multiple phenotypes such as pharmacologic responses to drugs, disease risks, comorbidities, substance abuse problems, etc. Panomics data may be generated and collected for the purpose of a specific set of medical decisions at a discrete point in time, and also may be harvested from the sum record of previously collected panomics data at points in the past for an individual patient.

As used herein, the term "pharmacological phenotype" may refer to any discernible phenotype which may have bearing on medical treatment, patient longevity and outcomes, quality of life, etc., in the context of clinical care, management and finance of clinical care, and pharmaceutical and other medical and biomedical research in humans and other organisms. Such phenotypes may include pharmacokinetic (PK) and pharmacodynamic phenotypes (PD) including all phenotypes of rates and characters of absorption, distribution, metabolism, and excretion of drugs (ADME), as well as response to drugs related to efficacy, therapeutic dosages of drugs, half-lives, plasma levels, clearance rates, etc., as well as adverse drug events, adverse drug response and corresponding severities of the adverse drug events or adverse drug response, organ injury, substance abuse and dependence and the likelihood thereof, as well as body weight and changes thereof, mood and behavioral changes and disturbances. Such phenotypes may also include reactions, beneficial and adverse, to combinations of drugs, drugs interactions with genes, sociological and environmental factors, dietary factors, etc. They may also include adherence to a pharmacological or non-pharmacological treatment regime. They may also include medical phenotypes such as the propensity of the patient to contract a certain disease or comorbid condition, outcomes and prognoses of disease, whether the patient will suffer particular symptoms of disease, and patient outcomes like longevity, clinical scores and parameters, test results, health care spending, and other phenotypes.

Furthermore, as used herein the term "pharmacophenomics" may refer to an individual patient pharmacological phenotype based on integrating genetic, epigenetic, panomic, pharmacometabolomic, sociomic, electronic health records (EHR), and other patient data, matched against stratified patient cohorts and population datasets enabled by machine learning.

"Precision patient phenotypes" as used herein may refer to an integrated analysis of pharmacophenomic data to provide a precise and accurate clinical decision patient treatment profile which can be updated periodically to incorporate changing patient phenomic data.

As used herein, the term "phenotype transitions" may refer to periodic changes in clinical patient phenotypes, either recurring or intermittent over time, as a function of disease progression, sociological and environmental factors, and/or the result of initial, ongoing or changing pharmacological and non-pharmacological treatment, essentially a longitudinal record of patients' clinical progression.

Moreover, as used herein the term "disease predisposition" may refer to risk factors associated with direct genetic inheritance or through transgenerational epigenetic modifications.

"Sociomic risk factors" as used herein may refer to sociological and cultural clinical risk factors associated with behavior harmful to self or others; adverse cultural environment, economic and community living conditions; childhood and/or adolescent neglect and abuse, referred to as Adverse Childhood Experiences (ACE); adult trauma associated with sexual, physical and psychological abuse; other acute or chronic traumatic events (e.g., military conflict, crimes, crashes, illnesses, family deaths); heightened or chronic stress resulting from adverse conditions; age-related health, isolation or cognitive circumstances.

A "disease diagnosis" as used herein may refer to a probable or definitive diagnosis leading to treatment decisions. A "treatment selection" as used herein may refer to pharmacological and/or non-pharmacological treatment(s) to alleviate, neutralize or improve a patient's condition.

Also as used herein, the term "initial treatment response" may refer to a stable condition, lack of response, improved clinical response, or adverse events (AEs) resulting from pharmacological treatment within the first several weeks to months; may involve dose adjustments or adjunctive medications. Time period is generally within six months up to one year.

The term "recurring response" as used herein may refer to periodic changes in patient response to treatment, resulting from pharmacological adverse reactions, drug-drug interactions, drug dosing changes, new or recurring comorbidities, trauma, stress, and other sociomic factors, measured via biological samples such as, but not limited to, blood, urine, sweat (e.g., cortisol), odor, or via remote sensing, transmitters, or other active or passive data collection methods.

As used herein, the term "environment" shall refer to any objects, substances, emanations, conditions, experiences, communications, or information external to a human or other animal or organism, or originating externally to such a human or other organism, occurring either in the present or in the past (including to biological generations preceding such a human or other organism), either at one or more discrete points in time or over a period of time, which may affect or modify the physical, biological, chemical, physiological, medical, psychological, or psychiatric properties of such a human or other organism in a measurable, discernable, or other significant way. Such conditions may include the type, quantity, quality, presence/absence, timing, or other features of food, nutritional supplements, minerals, water and other fluids, clothing, sanitation, and other goods and services to which the human or other organism was exposed, as well as exposures to chemical, atmospheric, and organismal entities, whether by the skin or through ingestion, inhalation, intubation, supposition, or other means in the present or in the past. Such conditions may include temperature, noise, light, electromagnetic and/or particle radiation, vibration, mechanical impact or pressure, medications, and medical procedures and implants. Such conditions may also include occupational properties, job duties, and recreational substances. Such conditions may also include medically adverse events such as exposure to toxins, poisons, microorganisms, viruses, and other agents, as well as physical impact, lacerations, contusions, punctures, and concussion.

Such conditions may also include social factors such as Adverse Childhood Experiences (ACE), as well as stress, trauma, abuse, poverty and other economic conditions, food insecurity and hunger, imprisonment, interpersonal conflict, violence, and other experiences. Such conditions may also include the presence or absence of parents, children, siblings, and other family members and acquaintances, including the type, quality, and duration of such relationships. Such conditions may also include education and professional experiences and attainment, religious services and instruction, and social associations and interactions. Such conditions may also include sociomic risk factors, as well as body modification including tattoos, implants, piercings, and mortification.

The term "contemporaneous pharmacogenomics substance exposures" as used herein may refer to a subtype of environmental elements which are unidirectional, contemporaneous, pharmacokinetic or pharmacodynamic, drug-environment interactions. Such interactions may be considered clinically significant, e.g. if there is a documented interaction that shows the environmental agent individually either induces or inhibits the activity of a specific enzyme associated with the metabolism of the drug by ≥20%, or alters the action of the drug by ≥20%, for exposure which is recent or ongoing at the time of the analysis. Such interactions may include forms of exposure ranging from food to herbal/vitamin supplements to voluntary and involuntary toxic exposures. The potential for such interactions may be evaluated on a numeric scale.

For simplicity, throughout this discussion, patients having data used as training data to generate the statistical model may be referred to herein as "training patients" and patients having data that is applied to the statistical model to predict pharmacological phenotypes may be referred to herein as "current patients." However, this is for ease of discussion only. Data from "current patients" may be added to the training data and the training data may be continuously or periodically updated to keep the statistical model up to date. Additionally, training patients may also have data applied to the statistical model to predict pharmacological phenotypes.

Additionally, throughout this discussion, current patients may be described as patients where it is unknown whether they have certain pharmacological phenotypes and training patients may be described as patients where the pharmacological phenotypes are known. More specifically, the pharmacological phenotypes for current patients are unknown and predicted using the relationship between the panomic and sociomic, physiomic and environmental data for the training patients and previously or currently determined pharmacological phenotypes for the training patients. Accordingly, training patients have known, previously or currently determined pharmacological phenotypes. Current patients have unknown pharmacological phenotypes. However, in some embodiments, training patients may have other unknown pharmacological phenotypes while having some known pharmacological phenotypes used to train the pharmacological phenotype prediction system. Additionally, current patients may have some known, previously or currently determined pharmacological phenotypes while having an unknown pharmacological phenotype that is being predicted by the pharmacological phenotype prediction system.

Generally speaking, techniques for identifying pharmacological phenotypes based on panomic, sociomic, physiomic and environmental characteristics may be implemented in one or several client devices, one or several network servers, or a system that includes a combination of these devices. However, for clarity, the examples below focus primarily on an embodiment in which a pharmacological phenotype assessment server obtains a set of training data. In some embodiments, the training data may be obtained from a client device. For example, a health care provider may obtain a biological sample for measuring a patient's panomics (e.g., from saliva, a cheek swab, sweat, a skin sample, a biopsy, a blood sample, urine, stool, sweat, lymph fluid, bone marrow, hair, odor, etc.) and provide laboratory results obtained by analyzing the biological sample to the pharmacological phenotype assessment server.

Figure 4A:
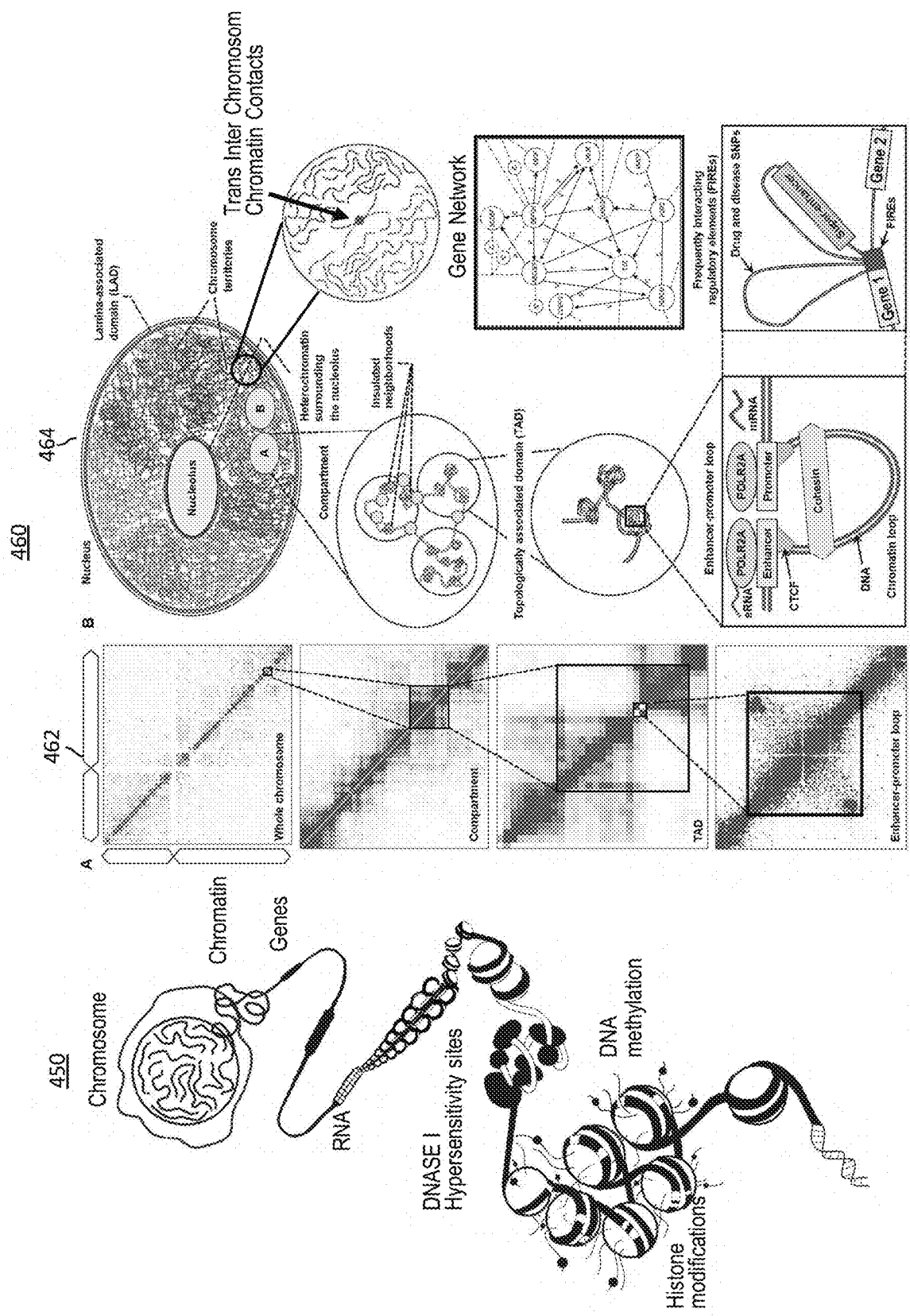
FIG. 4A depicts an exemplary representation of a bioinformatics analysis on permissive candidate variants associated with a particular pharmacological phenotype and a schematic diagram representing an exemplary spatial hierarchy of transcription in the human genome in accordance with the presently described embodiments.
Figure 4B:
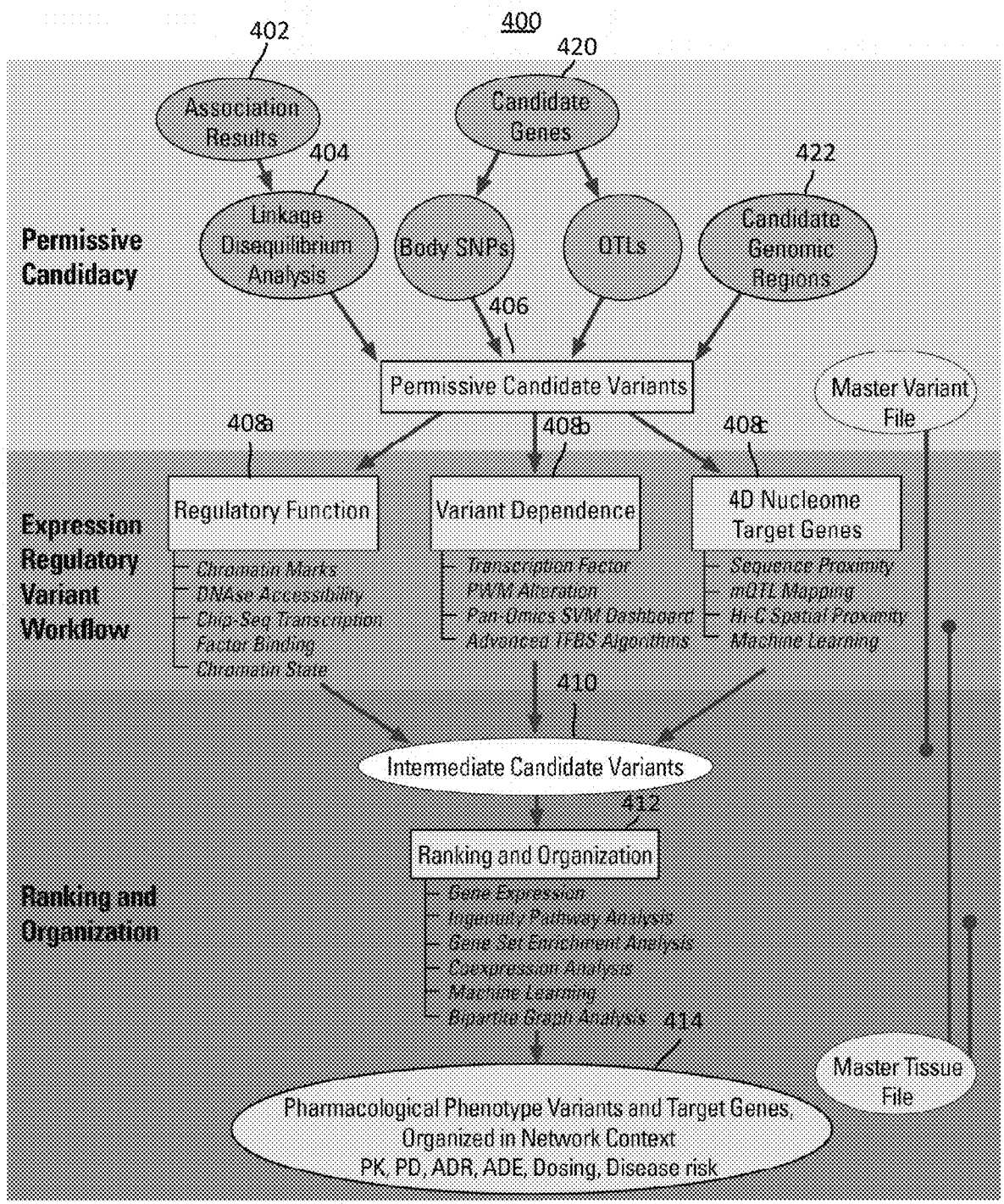
FIG. 4B is a block diagram representing an exemplary method for identifying panomic data that corresponds to a particular pharmacological phenotype using machine learning techniques in accordance with the presently described embodiments.
Figure 4C:
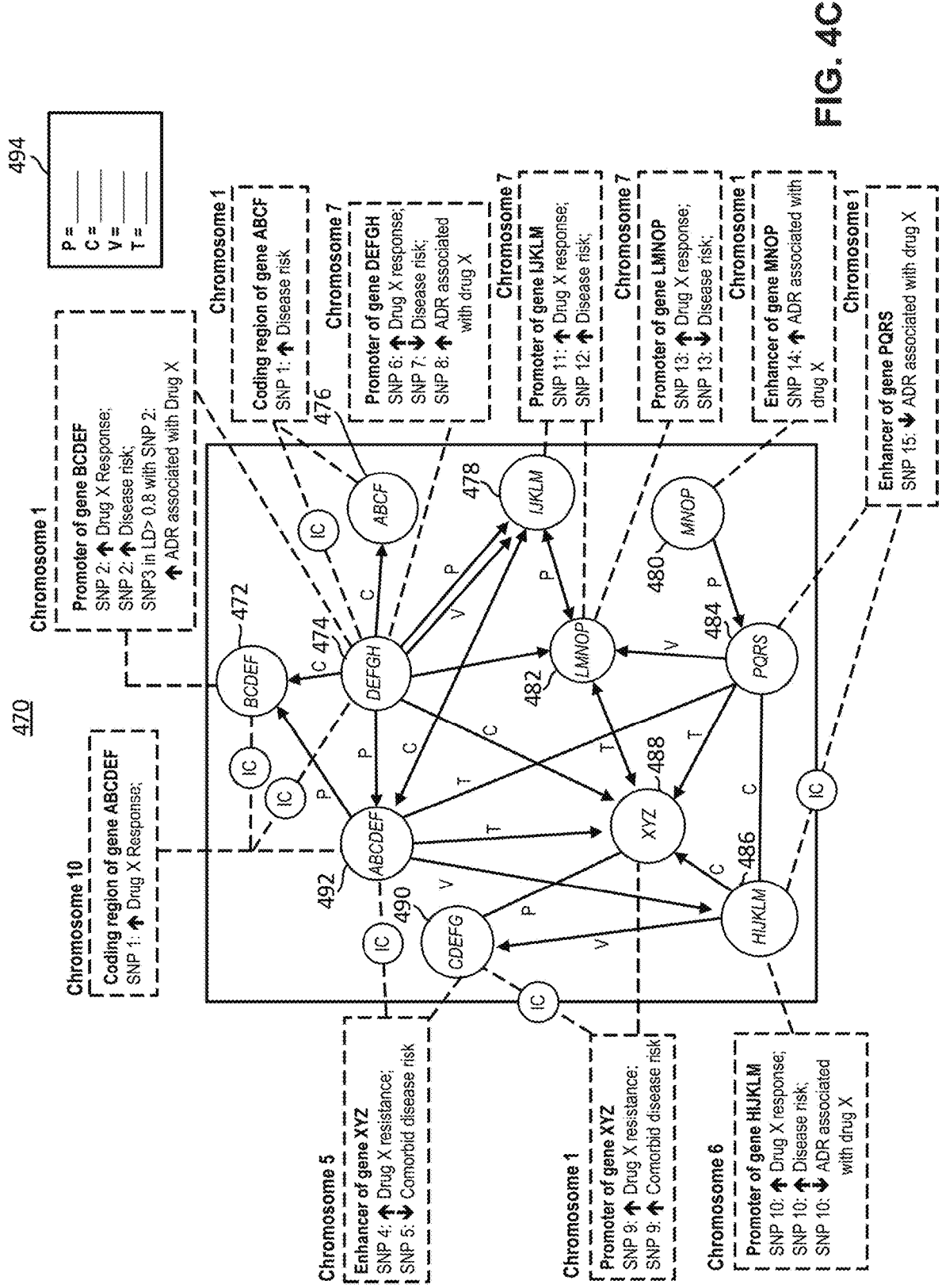
FIG. 4C depicts an exemplary gene regulatory network for a patient in accordance with the presently described embodiments.
Figure 5:
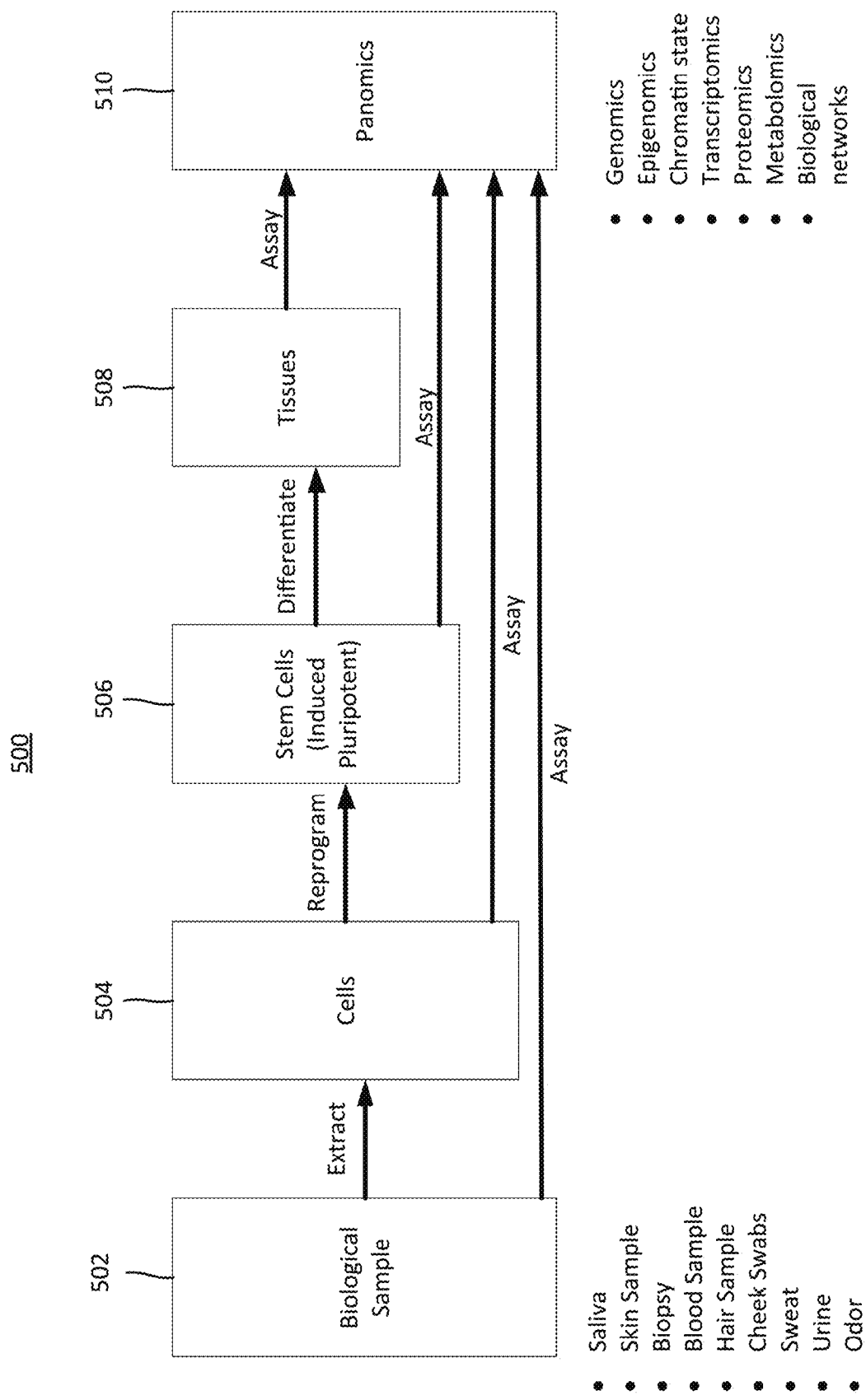
FIG. 5 is a block diagram representing an exemplary process for generating panomic data from patients' biological samples.

An example process 500 for generating panomic data from a patient's biological sample is illustrated in FIG. 5. The process may be performed by an assay laboratory or other suitable organization. At block 502, a patient's biological sample is obtained by a healthcare provider and sent to an assay laboratory for analysis. The biological sample may include the patient's saliva, sweat, skin, blood, urine, stool, sweat, lymph fluid, bone marrow, hair, cheek cells, odor, etc. Cells are then extracted from the biological sample at block 504 and reprogrammed into stem cells at block 506, such as induced pluripotent stem cells (iPSCs). Then at block 508, the iPSCs are differentiated into various tissues, such as neurons, cadiomyoctyes, etc., and assayed to obtain panomic data at block 510. The panomic data may include genomic data, epigenomic data, transcriptomic data, proteomic data, chromosomic data, metabolomic data, and/or biological networks. As described in more detail below with reference to FIGS. 4A-4C, SNPs, genes, and genomic regions may be identified as related to a particular pharmacological phenotype. When a patient's panomic, sociomic, physiomic and environmental data are analyzed with respect to a particular pharmacological phenotype or set of pharmacological phenotypes (e.g., pharmacological phenotypes indicative of a response to valproic acid), the iPSCs may be assayed for the identified SNPs, genes, and genomic regions related to the particular set of pharmacological phenotypes. More generally, the selection of which panomic data to assay may be based on panomic data identified as being related to the set of pharmacological phenotypes under examination for the patient.

More specifically, cells are reprogrammed into iPSCs through the introduction of transcription factors or "reprogramming factors" or other agents into a given cell type. For example, the Yamanaka factors including the transcription factors Oct4, Sox2, cMyc, and Klf4 may be used to reprogram cell into iPSCs. The iPSCs may then be differentiated into a variety of tissues, such as neurons, adipocytes, cardiomyocytes, pancreatic beta-cells, etc. After the iPSCs have been differentiated, the differentiated iPSCs may be assayed using various assaying techniques such as DNA methylation analysis, DNAse footprinting assay, filter binding assay, etc. to identify epigenomic information. In effect, the pharmacological phenotype prediction system performs a virtual biopsy and the differentiated iPSCs take on the phenotypic and epigenomic properties of their corresponding tissues at least to some extent.

In the embodiments described above, cells are extracted from the patient's biological sample, reprogrammed into stem cells, differentiated into various tissues, and assayed to obtain panomic data (assay on differentiated, reprogrammed cells). Alternatively, in some embodiments, the patient's biological sample is assayed without extracting cells (cell-free assay). In other embodiments, cells are extracted from the patient's biological sample and assayed without being reprogrammed or differentiated (assay on primary cells). In yet other embodiments, the cells are reprogrammed into iPSCs and assayed without being differentiated (assay on reprogrammed stem cells). For example, the iPSCs may be assayed without being differentiated to obtain stem cell omics. While these are merely a few example processes for generating panomic data from a patient's biological sample, assays may be performed at any suitable stage in the process and panomic data may be generated in any suitable manner.

The health care provider may also obtain physiological measures including vital signs, sleep circle, circadian rhythm, etc. Moreover, the health care provider may obtain data related to the pharmacometabolome, including metabolites which are the products of the metabolism, such as acetic acid, lactic acid, etc. and the pharmacometabolome metabolites of drugs. Metabolites may be identified through spectrometry or spectroscopy performed in a laboratory on the patient's biological sample for example, and the results may be provided as a metabolic profile for the patient to the health care provider. The metabolic profile may then be used to identify metabolic disease signatures, identify compounds that may alter drug response, identify metabolite variables and map the metabolite variables to known metabolic and biological pathways, etc.

In some embodiments, the pharmacological phenotype prediction system may make use of pharmacometabolomics data containing a systematic assessment of the presence or absence, and/or quantitative levels of a plurality of drugs and drug metabolites. Such information may be collected from whole blood, citrated blood, blood spots, other tissues and fluids, etc. The pharmacological phenotype prediction system may make use of one or more instances of pharmacometabolomic data preexisting within the EHR system or other databases, and/or data queried for current treatment or pharmacological phenotype prediction. The data may be collected both for prescribed drugs, unprescribed drugs, over the counter drugs, illegal drugs, etc. The concentrations of drugs and metabolites may be measured by technologies including mass spectroscopy and other forms of spectroscopy and spectrometry, and/or nuclear magnetic resonance, antibody and affinity tests, etc. Such information may be used in embodiments to detect drug abuse or off-label use, gauge compliance with prescribed drugs, detect other prescribed or other over the counter drugs used by patient or prescribed in other clinics, to gauge patient metabolizer status, and other purposes, etc., and to make treatment recommendations including prescribing, ceasing, and substituting drugs, as well as dosage and regimen changes, modes of administration, monitoring, testing, and diagnosis, specialist referrals, additional diagnoses, other treatments, etc.

In other embodiments, the physiological measures may be obtained from the patient's client computing device, fitness tracker, or quantified self-reporting/passive reporting methods. In another example, a health care provider may obtain a patient survey including questions regarding the patient's demographics, medical history, socioeconomic status, law enforcement history, sleep cycle, circadian rhythm, etc., and may provide the results of the patient survey to the pharmacological phenotype assessment server. The training data may be obtained from electronic medical records (EMR) located at an EMR server and/or from polypharmacy data located at a polypharmacy server that aggregates pharmacy data for patients from several pharmacies. In some embodiments, the training data may be obtained from a combination of sources including several servers (e.g., an EMR server, a polypharmacy server, etc.) and client devices of health care providers and patients. For example, the training data for a particular patient may be obtained by cross-referencing personal history data for the patient (e.g., the patient's occupations, places of residence, etc.) with broader longitudinal data on these features as in for example, the Human Exposome Project.

In addition to providing training data to the pharmacological phenotype assessment server that includes panomic data for training patients where their pharmacological phenotypes are known, the pharmacological phenotype assessment server also obtains training data related to consortium omics data on baseline omics levels, omics distributions, or any other suitable panomic data that may be used to train the pharmacological phenotype assessment server.

In any event, subsets of the training data may be associated with the training patient to which the subsets of the training data correspond. Additionally, the pharmacological phenotype assessment server may assign subsets of the training patients and corresponding training data into cohorts based on demographics, for example. Then the pharmacological phenotype assessment server may be trained using the training data to generate a statistical model for predicting pharmacological phenotypes for a patient. Various machine learning techniques may be used to train the pharmacological phenotype assessment server.

After the pharmacological phenotype assessment server has been trained, panomic data, sociomic data, physiomic data and environmental data, which may be collected at several points in time, may be received for a current patient where his/her pharmacological phenotypes are unknown. In some embodiments, the pharmacological phenotype assessment server may obtain indications of illnesses or disorders from which the current patient is suffering to identify an optimal drug to treat each illness. This may include stress-related disorders, such as post-traumatic stress disorder (PTSD), depression, suicidality, dysregulated circadian rhythm, substance abuse disorders, phobias, stress ulceration, acute stress disorder, stress-related disorders included in the Oxford Handbook of Psychiatry, etc. The illnesses or disorders from which the current patient is suffering may also include bipolar disorder, schizophrenia, autism spectrum disorders, and attention deficit hyperactivity disorder (ADHD). Moreover, this may include generalized anxiety disorder and anxious depression as well as non-psychiatric comorbid disorders, such as irritable bowel syndrome (IBS), irritable bowel disease (IBD), Crohn's disease, gastritis, gastric and duodenal ulcers, and gastroesophageal reflux disease (GERD). Furthermore, the illnesses or disorders from which the current patient is suffering may include diseases of cardiology, fibromyalgia, chronic fatigue syndrome, etc. The pharmacological phenotypes for these illnesses or disorders may include those associated with any of the current and future drugs and/or other methods used to treat the respective illnesses or disorders.

The panomic, sociomic, physiomic and environmental data may then be analyzed, for example, using the various machine learning techniques to predict one or several pharmacological phenotypes of the patient. Indications of the pharmacological phenotypes may be transmitted to a health care provider's client device for the health care provider to review and determine an appropriate course of treatment according to the pharmacological phenotypes. Pharmacological phenotypes may be predicted in clinical settings as well as in research settings for drug development and insurance applications. In a research setting, pharmacological phenotypes related to experimental drugs may be predicted for potential cohorts of patients in the research program. Patients may be selected for an experimental treatment according to their predicted pharmacological phenotypes related to an experimental drug.

Referring to FIG. 1A, an example pharmacological phenotype prediction system 100 predicts pharmacological phenotypes for a patient according to the patient's panomic, sociomic, physiomic and environmental data using various machine learning techniques (precision patient phenotypes). The pharmacological phenotype prediction system 100 may obtain training data for cohorts of training patients which may be analyzed to identify relationships between the panomic, sociomic, physiomic and environmental data and the pharmacological phenotypes included in the training data. The pharmacological phenotype prediction system 100 may then generate a statistical model for predicting pharmacological phenotypes based on the analysis. When a pharmacological phenotype for a patient is unknown (e.g., the patient has not yet been prescribed lithium for bipolar disorder and therefore the patient's response to lithium is unknown), the pharmacological phenotype prediction system 100 may obtain panomic, sociomic, physiomic and environmental data for the patient and apply the panomic, sociomic, physiomic and environmental data to the statistical model to predict the patient's pharmacological phenotypes. For example, the pharmacological phenotype prediction system 100 may predict a likelihood that the patient will have an adverse reaction to a particular drug, may predict the efficacy or appropriate dosage for the drug, etc. The pharmacological phenotype prediction system 100 may perform clinical decision support (CDSS) to predict precision patient phenotypes for patients in a clinical setting. Additionally, the pharmacological phenotype prediction system 100 may perform pharmaceutical research to develop companion diagnostic tests to identify patients who will respond well or poorly to a drug being developed or approved, and who will suffer less or no side effects. Moreover, the pharmacological phenotype prediction system 100 may be used in the context of experimental treatments to recommend an experimental drug and/or a dosage for a researcher to prescribe to the current patient in a clinical research context.

The pharmacological phenotype prediction system 100 includes a pharmacological phenotype assessment server 102 and a plurality of client devices 106-116 which may be communicatively connected through a network 130, as described below. In an embodiment, the pharmacological phenotype assessment server 102 and the client devices 106-116 may communicate via wireless signals 120 over a communication network 130, which can be any suitable local or wide area network(s) including a WiFi network, a Bluetooth network, a cellular network such as 3G, 4G, Long-Term Evolution (LTE), 5G, the Internet, etc. In some instances, the client devices 106-116 may communicate with the communication network 130 via an intervening wireless or wired device 118, which may be a wireless router, a wireless repeater, a base transceiver station of a mobile telephony provider, etc. The client devices 106-116 may include, by way of example, a tablet computer 106, a smart watch 107, a network-enabled cell phone 108, a wearable computing device such as Google Glass™ or a Fitbit® 109, a personal digital assistant (PDA) 110, a mobile device smart-phone 112 also referred to herein as a "mobile device," a laptop computer 114, a desktop computer 116, wearable biosensors, a portable media player (not shown), a phablet, any device configured for wired or wireless RF (Radio Frequency) communication, etc. Moreover, any other suitable client device that records panomic data, clinical data, demographic data, polypharmacy data, sociomic data, physiomic data or other environmental data for patients may also communicate with the pharmacological phenotype assessment server 102.

In some embodiments, the patient may enter data into the desktop computer 116 for example, such as answers in response to a patient survey including questions regarding the patient's demographics, medical history, socioeconomic status, law enforcement history, sleep cycle, circadian rhythm, etc. In other embodiments, the health care provider may enter the data.

Each of the client devices 106-116 may interact with the pharmacological phenotype assessment server 102 to transmit the panomic data, clinical data, demographic data, polypharmacy data, sociomic data, physiomic data or other environmental data for a patient. In some embodiments, sociomic, physiomic and environmental data may be collected periodically (e.g., every month, every three months, every six months, etc.) to identify changes to the patient's sociological status and environment over time (e.g., from unemployed to employed, single to married, etc.). Also in some embodiments, at least some of the patient's sociomic, physiomic and environmental data may be recorded by a health care provider via the health care provider's client device 106-116 or may be self-reported via the patient's client device 106-116.

Each client device 106-116 may also interact with the pharmacological phenotype assessment server 102 to receive one or several indications of predicted pharmacological phenotypes for a current patient. The indications may include a recommendation of a drug to prescribe to the current patient for which the current patient has the highest predicted response (e.g., the highest combination of efficacy and minimum adverse drug reactions and severity of the reactions). The indications may also include risks of various illnesses for the current patient such as a probability of suffering from an illnesses, a categorical risk (e.g., low, medium, or high risk), etc. Additionally, the indications may include an indication of a likelihood of substance abuse such as a numerical likelihood or a categorical likelihood (e.g., low, medium, or high likelihood).

In an example implementation, the pharmacological phenotype assessment server 102 may be a cloud based server, an application server, a web server, etc., and includes a memory 150, one or more processors (CPU) 142 such as a microprocessor coupled to the memory 150, a network interface unit 144, and an I/O module 148 which may be a keyboard or a touchscreen, for example.

The pharmacological phenotype assessment server 102 may also be communicatively connected to a consortium-omics/environmental/physiomics/demographics/pharmacy information database 154. The consortium-omics/environmental/physiomics/demographics/pharmacy information database 154 may store the training data including panomic data, whole genome based ethnicity data, clinical data, demographic data, polypharmacy data, sociomic data, physiomic data or other environmental data for training patients and the statistical model for determining pharmacological phenotypes. The consortium-omics/environmental/physiomics/demographics/pharmacy information database 154 may also include consortium and academic omics databases as well as pharmacy databases including (e.g.) RxNorm, drug-drug interactions such as FDA Black Box labels, drug-gene interactions, and others. In some embodiments, to determine pharmacological phenotypes, the pharmacological phenotype assessment server 102 may retrieve patient information for each training patient from the consortium-omics/environmental/physiomics/demographics/pharmacy information database 154.

The memory 150 may be tangible, non-transitory memory and may include any types of suitable memory modules, including random access memory (RAM), read only memory (ROM), flash memory, other types of persistent memory, etc. The memory 150 may store, for example instructions executable of the processors 142 for an operating system (OS) 152 which may be any type of suitable operating system such as modern smartphone operating systems, for example. The memory 150 may also store, for example instructions executable on the processors 142 for a machine learning engine 146 which may include a training module 160 and a phenotype assessment module 162. The pharmacological phenotype assessment server 102 is described in more detail below with reference to FIG. 1B. In some embodiments, the machine learning engine 146 may be a part of one or more of the client devices 106-116, the pharmacological phenotype assessment server 102, or a combination of the pharmacological phenotype assessment server 102 and the client devices 106-116.

In any event, the machine learning engine 146 may receive electronic data from the client devices 106-116. For example, the machine learning engine 146 may obtain a set of training data by receiving panomic data, clinical data, demographic data, polypharmacy data, sociomic data, physiomic data or other environmental data, etc. Additionally, the machine learning engine 146 may obtain a set of training data by receiving phenomic data related to pharmacological phenotypes for the training patients, such as the chronic diseases the training patients suffer from, responses to drugs previously prescribed to the training patients, whether each of the training patients suffers from substance abuse problems, etc.

As a result, the training module 160 may classify the panomic data, sociomic data, physiomic data and environmental data into specific pharmacological phenotypes, such as substance abuse, a particular type of chronic disease, an adverse drug reaction to a particular drug, an efficacy level for a particular drug, etc. The training module 160 may then analyze the classified panomic data, sociomic data, physiomic data and environmental data to generate a statistical model for each pharmacological phenotype. For example, a first statistical model may be generated for determining a likelihood that a current patient will experience substance abuse problems, a second statistical model may be generated for determining a risk of suffering from one type of illness, a third statistical model may be generated for determining a risk of suffering from another type of illness, a fourth statistical model may be generated for determining a likelihood of a negative response to a particular drug, etc. In some embodiments, each statistical model may be combined in any suitable manner to generate an overall statistical model for predicting each of the pharmacological phenotypes. In any event, the set of training data may be analyzed using various machine learning techniques, including, but not limited to regression algorithms (e.g., ordinary least squares regression, linear regression, logistic regression, stepwise regression, multivariate adaptive regression splines, locally estimated scatterplot smoothing, etc.), instance-based algorithms (e.g., k-nearest neighbors, learning vector quantization, self-organizing map, locally weighted learning, etc.), regularization algorithms (e.g., Ridge regression, least absolute shrinkage and selection operator, elastic net, least-angle regression, etc.), decision tree algorithms (e.g., classification and regression tree, iterative dichotomizer 3, C4.5, C5, chi-squared automatic interaction detection, decision stump, M5, conditional decision trees, etc.), clustering algorithms (e.g., k-means, k-medians, expectation maximization, hierarchical clustering, spectral clustering, mean-shift, density-based spatial clustering of applications with noise, ordering points to identify the clustering structure, etc.), association rule learning algorithms (e.g., apriori algorithm, Eclat algorithm, etc.), Bayesian algorithms (e.g., naïve Bayes, Gaussian naïve Bayes, multinomial naïve Bayes, averaged one-dependence estimators, Bayesian belief network, Bayesian network, etc.), artificial neural networks (e.g., perceptron, Hopfield network, radial basis function network, etc.), deep learning algorithms (e.g., multilayer perceptron, deep Boltzmann machine, deep belief network, convolutional neural network, stacked autoencoder, generative adversarial network, etc.), dimensionality reduction algorithms (e.g., principal component analysis, principal component regression, partial least squares regression, Sammon mapping, multidimensional scaling, projection pursuit, linear discriminant analysis, mixture discriminant analysis, quadratic discriminant analysis, flexible discriminant analysis, factor analysis, independent component analysis, non-negative matrix factorization, t-distributed stochastic neighbor embedding, etc.), ensemble algorithms (e.g., boosting, bootstrapped aggregation, AdaBoost, stacked generalization, gradient boosting machines, gradient boosted regression trees, random decision forests, etc.), reinforcement learning (e.g., temporal difference learning, Q-learning, learning automata, State-Action-Reward-State-Action, etc.), support vector machines, mixture models, evolutionary algorithms, probabilistic graphical models, etc.

In a testing phase, the training module 160 may compare test panomic data, sociomic data, physiomic data and environmental data for a test patient to the statistical model to determine a likelihood that the test patient has a particular pharmacological phenotype.

If the training module 160 makes the correct determination more frequently than a predetermined threshold amount, the statistical model may be provided to a phenotype assessment module 162. On the other hand, if the training module 160 does not make the correct determination more frequently than the predetermined threshold amount, the training module 160 may continue to obtain training data for further training.

The phenotype assessment module 162 may obtain the statistical model as well as a set of panomic data, sociomic, physiomic and environmental data for a current patient, which may be collected over a period of time (e.g., one month, three months, six months, one year, etc.). For example, a current patient's biological sample (e.g., a blood sample, saliva, a biopsy, bone marrow, hair, etc.) may be analyzed in a laboratory to obtain genomic data, epigenomic data, transcriptomic data, proteomic data, chromosomic data, and/or metabolomic data for the current patient. The panomic data may then be provided to the phenotype assessment module 162. Additionally, clinical data for the patient may be provided from an EMR server or a client device 106-116 of a health care provider. Polypharmacy data may be provided from a polypharmacy server or from several pharmacy servers and demographic data, sociomic data, physiomic data and other environmental data may be provided from a client device 106-116 of the health care provider or client device 106-116 of the current patient.

The panomic, sociomic, physiomic and environmental data may then be applied to the statistical model generated by the training module 160. Based on the analysis, the phenotype assessment module 162 may determine likelihoods or other semi-quantitative and quantitative measures indicating that the current patient has certain pharmacological phenotypes, such as a likelihood of substance abuse, likelihoods of various illnesses, overall ratings of predicted responses to various drugs, etc. The phenotype assessment module 162 may cause the likelihoods to be displayed on a user interface for a health care provider to review. Each likelihood may be represented as a probability (e.g., 0.6), a percentage (e.g., 80 percent), a category from a set of categories (e.g., "High," "Medium," or "Low"), and/or in any other suitable manner.

The pharmacological phenotype assessment server 102 may communicate with the client devices 106-116 via the network 130. The digital network 130 may be a proprietary network, a secure public Internet, a virtual private network and/or some other type of network, such as dedicated access lines, plain ordinary telephone lines, satellite links, combinations of these, etc. Where the digital network 130 comprises the Internet, data communication may take place over the digital network 130 via an Internet communication protocol.

Figure 1B:
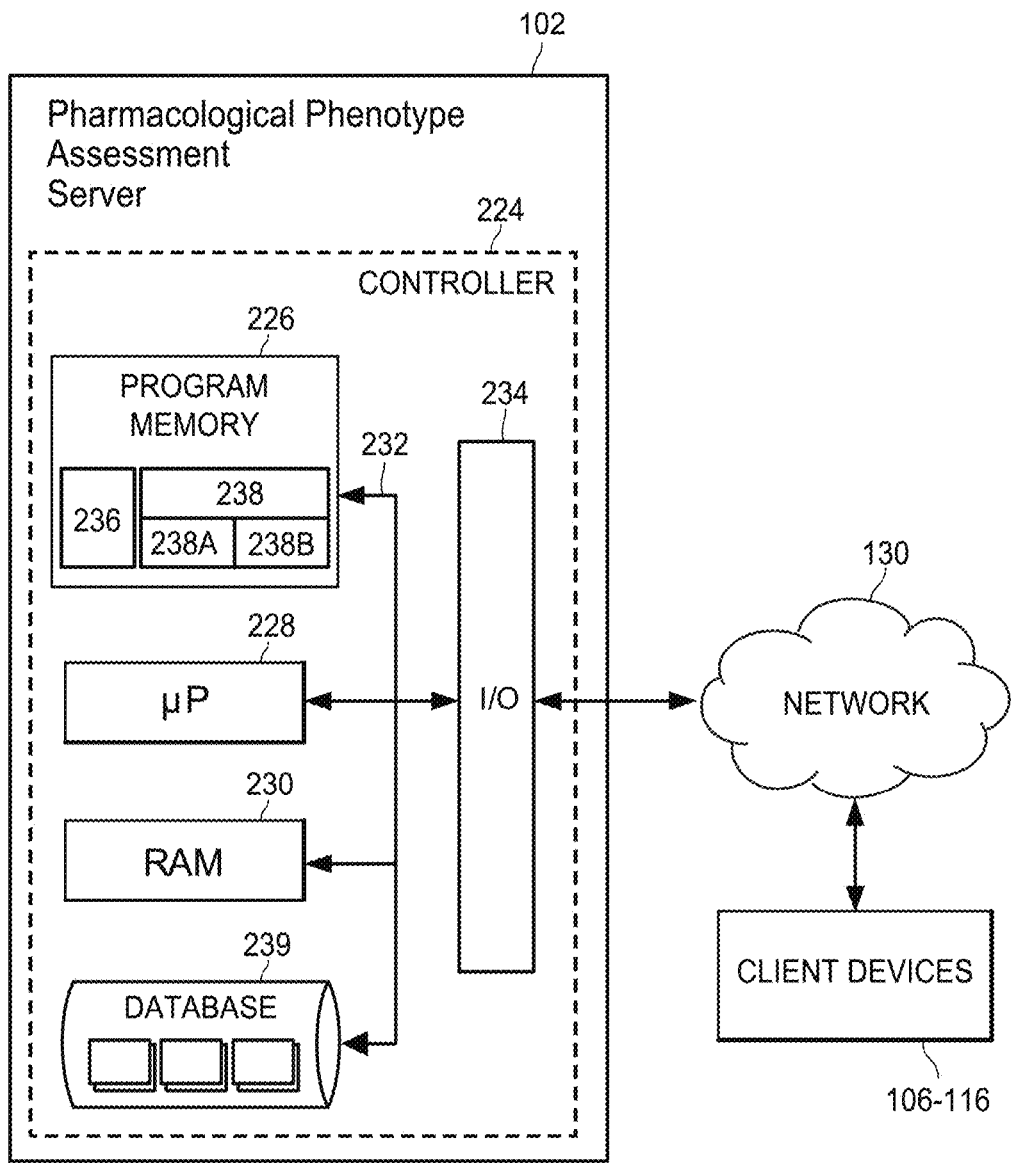
FIG. 1B is a block diagram of an exemplary pharmacological phenotype assessment server that can operate in the system of FIG. 1A in accordance with the presently described embodiments.

Turning now to FIG. 1B, the pharmacological phenotype assessment server 102 may include a controller 224. The controller 224 may include a program memory 226, a microcontroller or a microprocessor (MP) 228, a random-access memory (RAM) 230, and/or an input/output (I/O) circuit 234, all of which may be interconnected via an address/data bus 232. In some embodiments, the controller 224 may also include, or otherwise be communicatively connected to, a database 239 or other data storage mechanism (e.g., one or more hard disk drives, optical storage drives, solid state storage devices, etc.). The database 239 may include data such as patient information, training data, risk analysis templates, web page templates and/or web pages, and other data necessary to interact with users through the network 130. The database 239 may include similar data as the consortium-omics/environmental/physiomics/demographics/pharmacy information database 154 described above with reference to FIG. 1A and/or the data sources 325a-d (e.g., biomedical training sets 325a, a pharmacology database 325b, environmental data 325c, and data segmented by granularity 325d) described below with reference to FIG. 3.

It should be appreciated that although FIG. 1B depicts only one microprocessor 228, the controller 224 may include multiple microprocessors 228. Similarly, the memory of the controller 224 may include multiple RAMs 230 and/or multiple program memories 226. Although FIG. 1B depicts the I/O circuit 234 as a single block, the I/O circuit 234 may include a number of different types of I/O circuits. The controller 224 may implement the RAM(s) 230 and/or the program memories 226 as semiconductor memories, magnetically readable memories, and/or optically readable memories, for example.

As shown in FIG. 1B, the program memory 226 and/or the RAM 230 may store various applications for execution by the microprocessor 228. For example, a user-interface application 236 may provide a user interface to the pharmacological phenotype assessment server 102, which user interface may, for example, allow a system administrator to configure, troubleshoot, or test various aspects of the server's operation. A server application 238 may operate to receive a set of panomic data, sociomic data, physiomic data and environmental data for a current patient, determine likelihoods or other semi-quantitative and quantitative measures indicating that the current patient has pharmacological phenotypes, and transmit indications of the likelihood to a health care provider's client device 106-116. The server application 238 may be a single module 238 or a plurality of modules 238A, 238B such as the training module 160 and the phenotype assessment module 162.

While the server application 238 is depicted in FIG. 1B as including two modules, 238A and 238B, the server application 238 may include any number of modules accomplishing tasks related to implementation of the pharmacological phenotype assessment server 102. Moreover, it will be appreciated that although only one pharmacological phenotype assessment server 102 is depicted in FIG. 1B, multiple pharmacological phenotype assessment servers 102 may be provided for the purpose of distributing server load, serving different web pages, etc. These multiple pharmacological phenotype assessment servers 102 may include a web server, an entity-specific server (e.g. an Apple® server, etc.), a server that is disposed in a retail or proprietary network, etc.

Figure 1C:
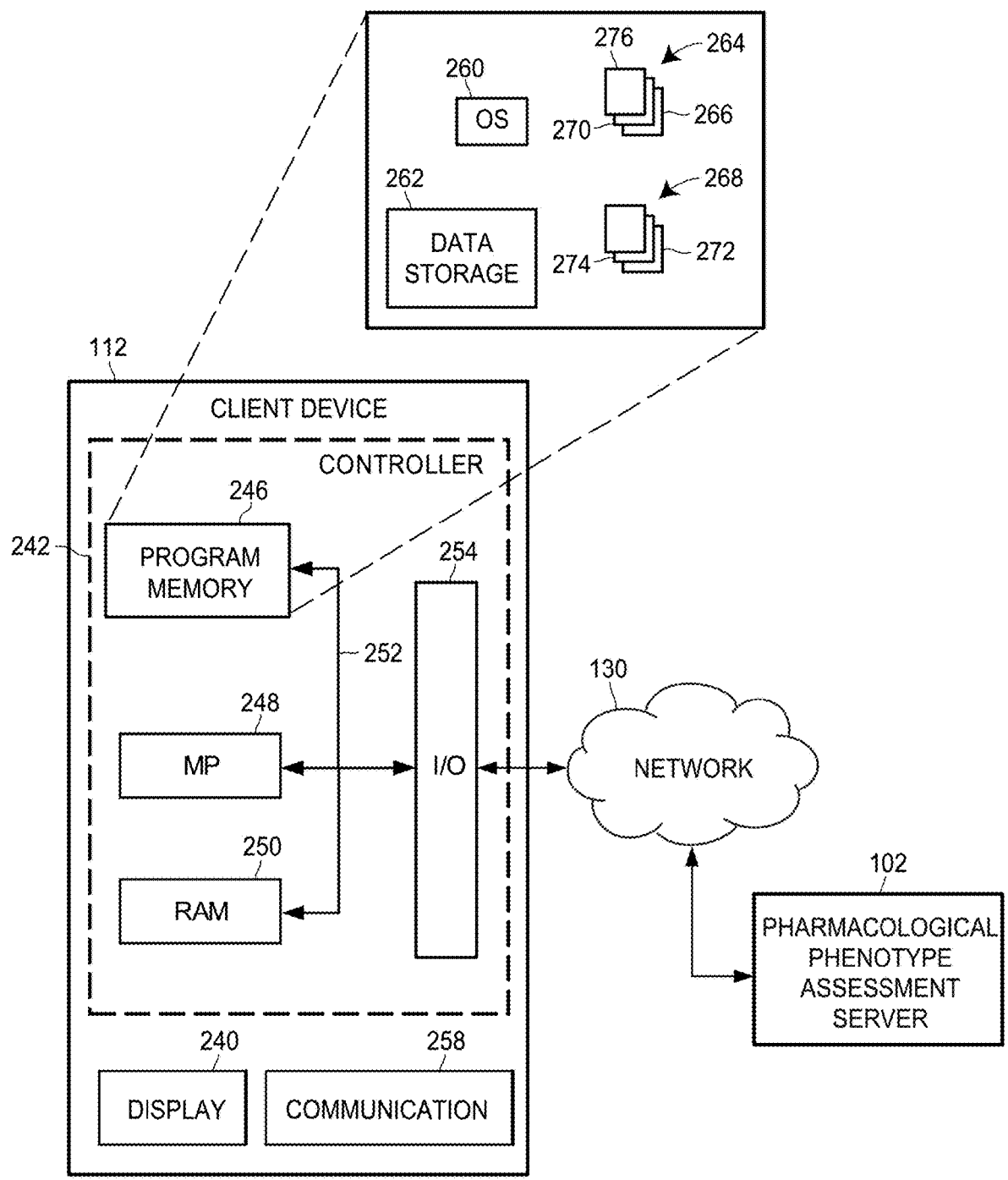
FIG. 1C is a block diagram of an exemplary client device that can operate in the system of FIG. 1A in accordance with the presently described embodiments.

Referring now to FIG. 1C, the laptop computer 114 (or any of the client devices 106-116) may include a display 240, a communication unit 258, a user-input device (not shown), and, like the pharmacological phenotype assessment server 102, a controller 242. Similar to the controller 224, the controller 242 may include a program memory 246, a microcontroller or a microprocessor (MP) 248, a random-access memory (RAM) 250, and/or an input/output (I/O) circuit 254, all of which may be interconnected via an address/data bus 252. The program memory 246 may include an operating system 260, a data storage 262, a plurality of software applications 264, and/or a plurality of software routines 268. The operating system 260, for example, may include Microsoft Windows®, OS X®, Linux®, Unix®, etc. The data storage 262 may include data such as patient information, application data for the plurality of applications 264, routine data for the plurality of routines 268, and/or other data necessary to interact with the pharmacological phenotype assessment server 102 through the digital network 130. In some embodiments, the controller 242 may also include, or otherwise be communicatively connected to, other data storage mechanisms (e.g., one or more hard disk drives, optical storage drives, solid state storage devices, etc.) that reside within the laptop computer 114.

The communication unit 258 may communicate with the pharmacological phenotype assessment server 102 via any suitable wireless communication protocol network, such as a wireless telephony network (e.g., GSM, CDMA, LTE, etc.), a Wi-Fi network (802.11 standards), a WiMAX network, a Bluetooth network, etc. The user-input device (not shown) may include a "soft" keyboard that is displayed on the display 240 of the laptop computer 114, an external hardware keyboard communicating via a wired or a wireless connection (e.g., a Bluetooth keyboard), an external mouse, a microphone for receiving voice input or any other suitable user-input device. As discussed with reference to the controller 224, it should be appreciated that although FIG. 1C depicts only one microprocessor 248, the controller 242 may include multiple microprocessors 248. Similarly, the memory of the controller 242 may include multiple RAMs 250 and/or multiple program memories 246. Although the FIG. 1C depicts the I/O circuit 254 as a single block, the I/O circuit 254 may include a number of different types of I/O circuits. The controller 242 may implement the RAM(s) 250 and/or the program memories 246 as semiconductor memories, magnetically readable memories, and/or optically readable memories, for example.

The one or more processors 248 may be adapted and configured to execute any one or more of the plurality of software applications 264 and/or any one or more of the plurality of software routines 268 residing in the program memory 246, in addition to other software applications. One of the plurality of applications 264 may be a client application 266 that may be implemented as a series of machine-readable instructions for performing the various tasks associated with receiving information at, displaying information on, and/or transmitting information from the laptop computer 114.

One of the plurality of applications 264 may be a native application and/or web browser 270, such as Apple's Safari®, Google Chrome™, Microsoft Internet Explorer®, and Mozilla Firefox® that may be implemented as a series of machine-readable instructions for receiving, interpreting, and/or displaying web page information from the pharmacological phenotype assessment server 102 while also receiving inputs from a user such as a health care provider.

Another application of the plurality of applications may include an embedded web browser 276 that may be implemented as a series of machine-readable instructions for receiving, interpreting, and/or displaying web page information from the pharmacological phenotype assessment server 102.

One of the plurality of routines may include a risk analysis display routine 272 which obtains likelihoods that the current patient has certain pharmacological phenotypes and displays indications of the likelihoods and/or recommendations for treating the current patient on the display 240. Another routine in the plurality of routines may include a data entry routine 274 which obtains sociomic, physiomic and environmental data for a current patient from the health care provider and transmits the received sociomic, physiomic and environmental data along with previously stored sociomic, physiomic and environmental data for the current patient (e.g., environmental data collected at a previous visit) to the pharmacological phenotype assessment server 102.

Preferably, a user may launch the client application 266 from a client device, such as one of the client devices 106-116 to communicate with the pharmacological phenotype assessment server 102 to implement the pharmacological phenotype prediction system 100. Additionally, the user may also launch or instantiate any other suitable user interface application (e.g., the native application or web browser 270, or any other one of the plurality of software applications 264) to access the pharmacological phenotype assessment server 102 to realize the pharmacological phenotype prediction system 100.

As mentioned above, the pharmacological phenotype assessment server 102 as shown in FIG. 1A, may include a memory 150 which may store instructions executable on the processors 142 for a machine learning engine 146. The machine learning engine 146 may include a training module 160 and a phenotype assessment module 162.

Figure 2:
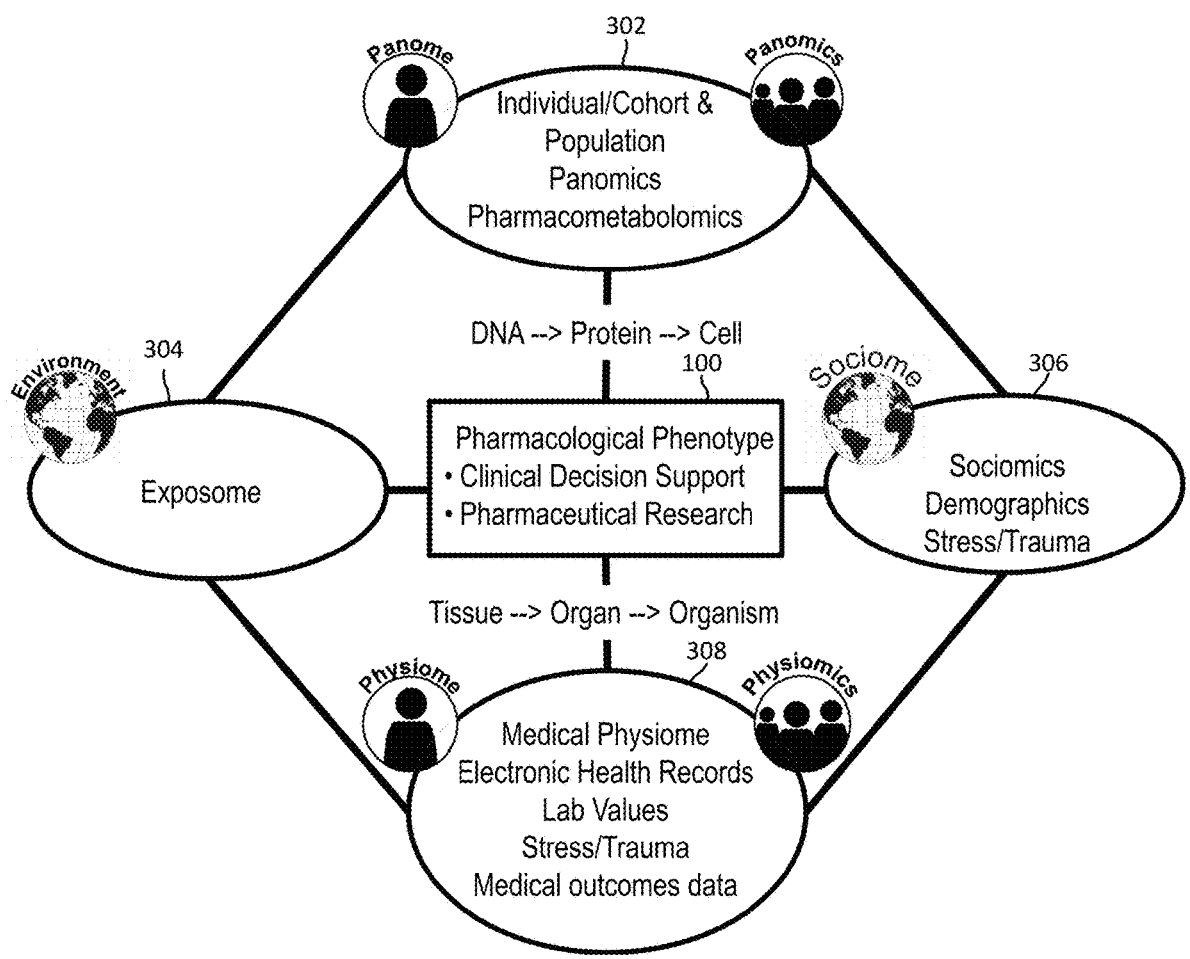
FIG. 2 depicts example panomic, sociological, and environmental data that may be provided to the pharmacological phenotype prediction system in accordance with the presently described embodiments.

FIG. 2 illustrates panomic, sociomic, physiomic and environmental data that may be provided to the pharmacological phenotype prediction system 100 which in turn predicts pharmacological phenotypes in a clinical or research setting. The panomic, sociomic, physiomic and environmental data is divided into four categories: individual/cohort and population panomics and pharmacometabolomics 302, exposome 304, sociomics demographics, and stress/trauma 306, and medical physiomics, structured or unstructured electronic health records (EHRs), laboratory values, stress and abuse factors and trauma, and medical outcomes data 308. However, this is merely for ease of illustration only. Exposome 304, sociomics demographics, and stress/trauma 306, and medical physiomics, structured or unstructured EHRs, laboratory values, stress and abuse factors and trauma, and medical outcomes data 308 may be included as part of the sociomic, physiomic and environmental data and individual/cohort and population panomics and pharmacometabolomics 302 be included as part of the panomic data.

Additionally, the individual/cohort and population panomics and pharmacometabolomics 302, exposome 304, sociomics demographics, and stress/trauma 306, and medical physiomics, structured or unstructured EHRs, laboratory values, stress and abuse factors and trauma, and medical outcomes data 308 may be categorized and/or organized in any other suitable manner.

In any event, individual/cohort and population panomics and pharmacometabolomics 302 may include genomics, epigenomics, chromatin state, transcriptomics, proteomics, metabolomics, biological networks and systems models, etc., each of which may be extracted from or at least related to the genome. Individual/cohort and population panomics and pharmacometabolomics 302 may also include a chemical mapping of discrete molecular entities within a tissue to various pharmacological phenotypes. The discrete molecular entities may be metabolites which are the products of the metabolism, such as acetic acid, lactic acid, etc. and the pharmacometabolome metabolites of drugs.

Exposome 304 may include information indicative of a patient's environment, such as the location of the patient's residence, the type of residence, the size of the residence, the quality of the residence, the work environment for the patient including the location of the patient's work place, the distance from the patient's residence to the work place, how the patient is treated at the work place and/or at the residence, etc. Exposome 304 may also include any other environmental exposures experienced by a patient including climate factors, lifestyle factors (e.g., tobacco, alcohol), diet, physical activity, contaminants, radiation, infections, education, etc.

Sociomics, demographics, and stress/trauma 306 may include demographic data such as gender, ancestry, age, income, marital status, education level, language, etc. Sociomics, demographics, and stress/trauma 306 may also include other household data, cultural conditions, circadian data, age-related health, isolation or cognitive circumstances, economics and community living conditions, etc. Furthermore, sociomics, demographics, and stress/trauma 306 may include trauma, domestic violence, law enforcement history or any other stress or abuse factors. In some embodiments, stress and abuse factors during childhood may be quantified by an Adverse Childhood Experiences (ACE) score that measures different types of abuse, neglect, and other measures of a difficult childhood. This may include physical, emotional, and sexual abuse, physical and emotional neglect, mental illness within the home, domestic violence within the home, divorce, substance abuse within the home, an incarcerated relative, etc.

Furthermore, medical physiomics, structured or unstructured EHRs, laboratory values, stress and abuse factors and trauma, and medical outcomes data 308 may include trauma, domestic violence, law enforcement history or any other stress or abuse factors. In some embodiments, stress and abuse factors during childhood may be quantified by an Adverse Childhood Experiences (ACE) score that measures different types of abuse, neglect, and other measures of a difficult childhood. This may include physical, emotional, and sexual abuse, physical and emotional neglect, mental illness within the home, domestic violence within the home, divorce, substance abuse within the home, an incarcerated relative, etc. Medical physiomics, structured or unstructured EHRs, laboratory values, stress and abuse factors and trauma, and medical outcomes data 308 may also include clinical data, polypharmacy data, and physiological features such as functions of the human body that are associated with genes and proteins. Further, medical outcomes data may include pharmacological phenotypes for a particular patient or patient cohort. Additionally, medical outcomes data may include information indicative of the efficacy of a drug or treatment, adverse drug events or adverse drug response, a stable condition, lack of response, improved clinical response, etc.

Individual/cohort and population panomics and pharmacometabolomics 302, exposome 304, sociomics demographics, and stress/trauma 306, and medical physiomics, structured or unstructured EHRs, laboratory values, stress and abuse factors and trauma, and medical outcomes data 308 for cohorts of training patients may be provided as training data to the pharmacological phenotype prediction system 100 to generate the statistical model for predicting pharmacological phenotypes. Additionally, individual panomics and pharmacometabolomics 302, exposome 304, sociomics demographics, and stress/trauma 306, and medical physiomics, structured or unstructured EHRs, laboratory values, stress and abuse factors and trauma, and medical outcomes data 308 or some portion thereof may be obtained from a current patient to be applied to the statistical model to predict the current patient's pharmacological phenotypes or precision patient phenotypes.

Figure 3:
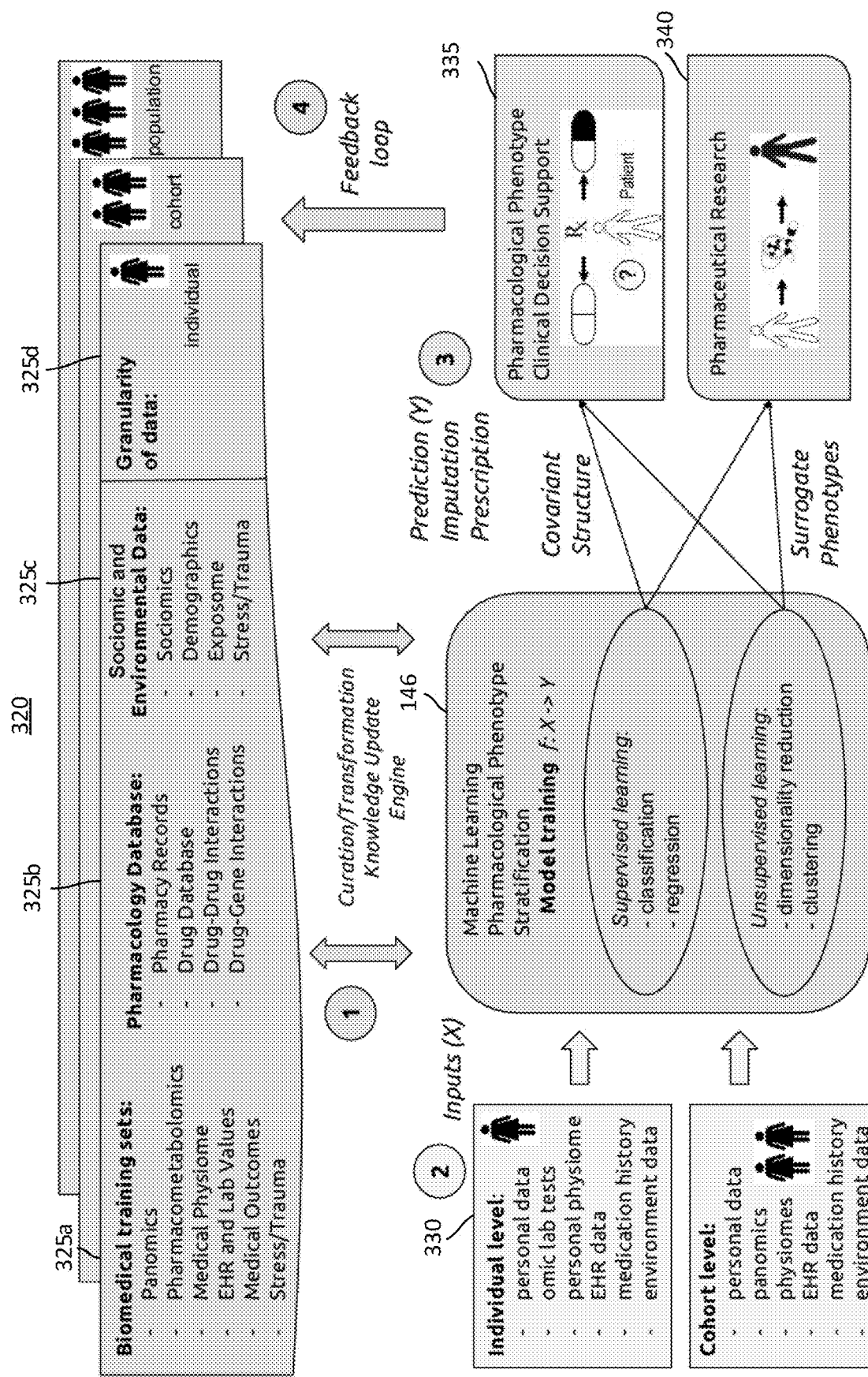
FIG. 3 depicts a detailed view of the process performed by the pharmacological phenotype prediction system in accordance with the presently described embodiments.

FIG. 3 illustrates a detailed view 320 of the process performed by the pharmacological phenotype prediction system 100. As shown in FIG. 2, the pharmacological phenotype prediction system 100 obtains individual/cohort and population panomics and pharmacometabolomics 302, exposome 304, sociomics demographics, and stress/trauma 306, and medical physiomics, structured or unstructured EHRs, laboratory values, stress and abuse factors and trauma, and medical outcomes data 308 as training data from cohorts of training patients to train the machine learning engine 146. In some embodiments, individual/cohort and population panomics and pharmacometabolomics 302 and their respective correlations with pharmacological phenotypes may be obtained from GWAS, candidate gene association studies, and/or other machine learning methods as described in more detail below. The training data may also be obtained from several data sources 325a-d including biomedical training sets 325a, a pharmacology database 325b, environmental data 325c, and data segmented by granularity 325d.

The biomedical training sets 325a include panomics, pharmacometabolomics, medical physiomics, EHRs, lab values, medical outcomes, and stress and abuse factors and trauma similar to the panomics and pharmacometabolomics 302 and medical physiomics, structured or unstructured EHRs, laboratory values, stress and abuse factors and trauma, and medical outcomes data 308 as described above with reference to FIG. 2. The pharmacology database 325b includes pharmacy records, drug databases, drug-drug interactions, drug-gene interactions, etc. Furthermore, the sociomic and environmental data 325c includes sociomics, demographics, and exposome similar to the exposome 304, sociomics demographics, and stress/trauma 306 as described above with reference to FIG. 2. The data segmented by granularity 325d may identify any of the data from the biomedical training sets 325a, pharmacology database 325b, and environmental data 325c as corresponding to an individual patient, a patient cohort, or a population of patients.

Then the machine learning engine 146 may utilize the panomic, sociomic, physiomic and environmental, and phenomic data for the cohorts or populations of training patients to generate a statistical model for predicting pharmacological phenotypes using machine learning techniques. In some embodiments, the machine learning engine 146 may analyze relationships between panomic data and pharmacological phenotypes to identify the single nucleotide polymorphisms (SNPs), genes, and genomic regions that are most highly correlated with a particular pharmacological phenotype. This is described in more detail below with reference to FIGS. 4B and 4D.

Additionally, the machine learning engine 146 may classify a cohort or population of the training patients having at least some of or any suitable combination of the identified SNPs, genes, and genomic regions as either having or not having the particular pharmacological phenotype based on the phenomic data for each training patient in the cohort or population. The machine learning engine 146 may further analyze the sociomic, physiomic and environmental data for the cohort or population of training patients corresponding to each classification to generate the statistical model. For example, the machine learning engine 146 may perform statistical measures on the sociomic, physiomic and environmental data for each classification to distinguish between the sociomic, physiomic and environmental data for the subset of training patients having the particular pharmacological phenotype and the subset of training patients not having the particular pharmacological phenotype. The machine learning engine 146 may be trained using supervised learning algorithms, such as classification and regression. The machine learning engine 146 may also be trained using unsupervised learning algorithms, such as dimensionality reduction and clustering.

In any event, the machine learning engine 146 may receive inputs 330 including panomic, sociomic, physiomic and environmental data from a current patient or cohort of current patients where it is unknown whether the current patient or cohort of current patients has/have the particular pharmacological phenotype. The inputs may include any of the individual panomics and pharmacometabolomics 302, exposome 304, sociomics demographics, and stress/trauma 306, and medical physiomics, structured or unstructured EHRs, laboratory values, stress and abuse factors and trauma, and medical outcomes data 308 mentioned above. For example, for an individual current patient, the inputs may include personal data, omics laboratory tests, personal physiomics, EHR data, medication history, and environmental data. For a cohort of current patients, the inputs may include personal data, cohort panomics, physiomics, EHR data, medication history and environmental data.

The panomic, sociomic, physiomic and environmental data for the current patient or cohort of current patients may be applied to the statistical model included in the machine learning engine 146 to predict a pharmacological phenotype for the current patient or cohort of current patients. For example, the machine learning engine 146 may predict a likelihood of a negative response to warfarin. Additionally or alternatively, the machine learning engine 146 may generate a response score indicative of the efficacy of warfarin on treating the current patient's thrombosis discounted for adverse effects of the warfarin on the current patient.

The likelihood, response score, or other semi-quantitative or quantitative measure may be analyzed by a pharmacological phenotype clinical decision support engine 335 within the pharmacological phenotype prediction system 100 to recommend a drug and/or a dosage for the health care provider to prescribe to the current patient. In some embodiments, response scores for each of the drugs available for use against a particular medical indication may be ranked and the pharmacological phenotype clinical decision support engine 335 may recommend the highest-ranked drug for the health care provider to prescribe to the current patient. Dosages for a particular drug may be also be ranked. In another example, when the likelihood of a negative response to one drug option is above a threshold score for the current patient, the pharmacogenomics clinical decision support engine 335 may recommend a different drug for the particular medical indication. Additionally, the pharmacological phenotype clinical decision support engine 335 may compare the recommended drug to the current patient's polypharmacy data included in the environmental data and/or medical records. If the current patient is taking a drug that is contraindicated with the recommended drug, the pharmacological phenotype clinical decision support engine 335 may recommend a drug having the next highest response score or another drug that does not have a likelihood of a negative response above a threshold likelihood. In other embodiments when the pharmacological phenotype is a likelihood of substance abuse, the pharmacogenomics clinical decision support engine 335 may recommend early intervention or when the pharmacological phenotype is a disease risk, the pharmacological phenotype clinical decision support engine 335 may recommend a screening and/or course of treatment to proactively address the issue. In other embodiments wherein the pharmacological phenotypes are other than described above, the pharmacological phenotype clinical decision support engine 335 may recommend other medical treatments, informative assays, or other courses of action.

Likelihoods, response scores, or other semi-quantitative or quantitative measures for pharmacological phenotypes may also be used in pharmaceutical research 340 in a variety of capacities. For example, researchers developing a drug may use such methods to develop companion diagnostic tests to identify patients who will respond well or poorly to a drug being developed or approved, and who will suffer less or no side effects. Additionally, researchers screening or comparing multiple molecular entities for use as putative drugs, and in possession of comparative data on molecular experiments using these drugs, may perform prospective evaluations of likely effects and adverse events for populations using these methods, as a means of deciding which entities to develop or prioritize in the development process. Additionally, these methods may be used in the context of experimental treatments to recommend an experimental drug and/or a dosage for a researcher to prescribe to the current patient in a clinical research context. Finally, these methods may be used in the explicit construction or model generation of pharmacogenomics tests to be carried out outside of an integrated CDSS environment.

The predicted pharmacological phenotype and/or recommendation provided by the pharmacological phenotype clinical decision support engine 335 or pharmaceutical research tool 340 may be provided to the data sources 325*a-d* in a feedback loop. The panomic, sociomic, physiomic and environmental, and phenomic data for the current patient is then used as training data for further training the machine learning engine 146 for subsequent use with other current patients. In this manner, the machine learning engine 146 may constantly update the statistical model to reflect at least a near real-time representation of the sociomic, physiomic environmental and panomic data.

FIG. 4A depicts an exemplary representation of the biological context and interaction of a number of different panomics modalities in the 4D nucleome, and an example of a bioinformatics analysis on panomic data in this context. The representation 450 depicts chromosomes located in chromatin-bound territories in the nucleus. Euchromatin is characterized by DNase 1 hypersensitivity and specific combination of histone marks that define active genomic regulatory elements, such as promoters H3K4me3 and H3K27ac, and enhancers H3K4me1 and H3K27ac. An enhancer can either increase or decrease transcription in its target genes, which may be sequence proximal, and/or spatially localized (via, e.g., Hi-C or ChIA-PET data, or Genome Architecture Mapping, or Combinatorial chromatin capture) and/or functionally connected (via, e.g., molecular QTL connection) to the enhancer, either singly or in combination. Heterochromatin is localized to the interior of chromosome territories and the periphery of the nucleus, near the nuclear lamin and the nucleolus, and is characterized by its own pattern of repressive chromatin marks and DNA bound proteins, as well as spatial compaction and linker histones. Recent research demonstrates that, in the brain, the DNA sequence CAC is a common site of methylation, in contrast to other tissues where CpG is most often methylated. Additionally, in the brain, 5-hydroxymethylcytosine (5hmC), a reactive species carrying a distinct element of epigenomic information, is relatively common. In contrast, in the periphery, methylcytosine (hmC) is common.

FIG. 4A also depicts a schematic diagram representing an exemplary spatial hierarchy 460 of transcriptional organization as first determined by chromatin conformation capture methods. The spatial hierarchy 460 includes a Hi-C mapping 462 that shows a multiscale hierarchy of transcriptional regulation. In this representation, the normalized frequencies of spatial interactions between portions of the genome (on the X axis) and other portions of the genome (on the Y axis) are represented with gradations of color to produce a two dimensional map of chromatin organization.

This map may be generated with "bins" representing fixed lengths of DNA sequences, or bins representing cutsite increments or collections thereof, or functional elements such as genes, chromatin state segments, loop domains, chromatin domains, TADs, etc. Contacts may be discerned with thresholding in a variety of normalization modes for distances, overall contact propensity, and other elements. For example, in the case of bins which are not fixed in sequence length, and for which therefore the squared genome area described by a pair of bins may be of variable size and shape, normalization methods may be devised to substitute for traditional methods which rely on fixed bins. The density of contacts as a function of distance may be fitted to an integrable function, which may be integrated over the rectangular area of a bin pair to produce an expected value of contacts mapped to this squared genome region. This expected value may be compared to the raw or normalized read counts mapping to this squared genome region with, e.g., statistical tests such as the Poisson distribution p-value, to which, e.g., Benjamini false discovery rates may be applied, to generate a collection of enriched and depleted chromatin contacts in a distance, adjusted manner, on a local or genome-wide basis. This may be carried out for the purposes of a variety of analyses, including the detection of target genes of genomic variants, as well as genome wide analysis of contacts.

The spatial hierarchy 460 also includes a visualization 464 of nuclear and sub-nuclear transcriptional topology shown in the Hi-C mapping 462. As shown in the visualization 464, chromosomes fill in much of the available volume of the nucleoplasm as territories (CTs), and contain circumscribed A and B compartments that consist of euchromatin and heterochromatin respectively. Active genes tend to be located on the periphery of CTs, and inter-chromosomal looping between CTs provides the basis for a subset of enhancer-promoter and promoter-promoter spatial interactions in trans. The A and B chromatin compartments of CTs contain topologically associated domains (TADs) within an average length in linear sequence of approximately 1 Mb. TADs may first be characterized using chromatin conformation capture methods such as Hi-C, where initial scaling is consistent with a fractal globule model, whereas high resolution study of enhancer-promoter loops within TADs, the organization of TAD boundary proteins including CCCTC-binding protein (CTCF) and cohesin (RAD21) and direct imaging support a loop extrusion model of TAD organization. Features of transcriptional units, including frequently interacting regulatory elements (FIREs), include an example located within an intron of the GRIN2A gene located on chromosome 16.

The epigenome tracks and/or bioinformatics analyses as described in FIG. 4A may be used by the machine learning methods to identify associations between genes, SNPs, and genomic regions and pharmacological phenotypes. For example, the epigenome track and/or bioinformatics analyses may be used to generate a gene regulatory network as shown in FIG. 4C. As mentioned above, the training module 160 may generate a statistical model for each pharmacological phenotype. FIG. 4B is a block diagram representing an exemplary method 400 for identifying panomic data that corresponds to a particular pharmacological phenotype using machine learning techniques. The method 400 may be executed on the pharmacological phenotype assessment server 102. In some embodiments, the method 400 may be implemented in a set of instructions stored on a non-transitory computer-readable memory and executable on one or more processors on the pharmacological phenotype assessment server 102. For example, the method 400 may be performed by the training module 160 within the machine learning engine 146 of FIG. 1A.

At block 402, for each of several noncoding or coding SNPs, genes, and genomic regions in the genome, a statistical test is performed (e.g., via GWAS or candidate gene association studies) to determine a relationship between the SNP and a particular pharmacological phenotype which may be a drug response, adverse drug response, an adverse drug event, a dosage, disease risk, etc. (e.g., a response to ketamine for patients suffering from depression). When the statistical test shows a significant relationship between an SNP and the particular pharmacological phenotype (e.g., having a p-value less than a threshold probability using the null hypothesis), the SNP is determined to be correlated with the particular pharmacological phenotype. In some embodiments, the SNPs may be identified based on the bioinformatics analysis as shown in FIG. 4A.

Then at block 404, a linkage disequilibrium analysis is performed on the SNPs correlated with the particular pharmacological phenotype to identify which SNPs are independent from each other. For example, when a set of SNPs are all correlated with the same pharmacological phenotype and are in tight linkage disequilibrium (e.g., LD>0.9), the set of SNPs may be linked such that it is unclear which of the SNPs in the set are the SNPs causing the correlation with the pharmacological phenotype. The linkage disequilibrium analysis may be performed to identify each of the SNPs that may be the cause of the correlation with the pharmacological phenotype (effector SNPs). More specifically, the linkage disequilibrium analysis may be performed by comparing the SNPs (original SNPs) to a database of SNPs (e.g., from the 1000 Genome Project) to find the SNPs linked to the original SNPs. In some embodiments, the ethnic population of the GWAS or candidate gene association study may be identified and SNPs along with linkage disequilibrium coefficients may be retrieved from the database of SNPs that correspond to the identified ethnic group. Then the pharmacological phenotype assessment server 102 may generate a set of permissive candidate variants (block 406) for all of the SNPs in tight linkage disequilibrium with the original SNPs correlated with the particular pharmacological phenotype from the GWAS or other candidate association studies.

Additionally, the set of permissive candidate variants (block 406) may include body SNPs of genes of known or suspected relevance with regard to a pharmacological phenotype under investigation (block 420), molecular QTLs which target the bodies of genes, and SNPs resident in genomic regions or networks of known or suspected relevance with regard to a pharmacological phenotype under investigation (block 422). In any event, the permissive candidate variants (block 406) may undergo a bioinformatics analysis to filter the permissive candidate variants into a subset of intermediate candidate variants (block 410) and then the subset of intermediate candidate variants may be ranked (e.g., via a scoring system) (block 412). The highest-ranking SNPs, genes, and genomic regions of known or suspected relevance with regard to a pharmacological phenotype under investigation within the subset of intermediate candidate variants (e.g., ranked above a threshold ranking or having a score above a threshold score) may then be identified as the SNPs, genes, and genomic regions putatively causally related to the particular pharmacological phenotype (block 414). For example, the SNPs, genes, and genomic regions may be associated with drug response, adverse drug response, adverse drug events, disease risk, dosage, comorbidity, substance abuse, drug-gene interactions, drug-drug interactions, polypharmacy interactions, etc.

More specifically, to filter out a portion of the permissive candidate variants to generate the subset of intermediate candidate variants (block 410), genomic regions around the permissive candidate variants are evaluated for regulatory function (block 408*a*), to determine whether their sequence contexts (e.g., alleles) influence the regulatory function (variant dependence) (block 408*b*), and to determine their target genes (block 408*c*).

To assess whether a permissive candidate variant is functional, a bioinformatics analysis may be used to determine whether a permissive candidate variant is located in open chromatin, as indicated by DNase I hypersensivity. An exemplary representation 450 of this bioinformatics analysis is depicted in FIG. 4A.

Variant dependence may be determined using various machine learning techniques such as support vector machines (SVM). For example, an SVM may be used with the permissive candidate variants to create a hyperplane for classifying k-mers, gapped k-mers, or other local sequence features in DNA sequences. The SVM may be used to measure the propensity of particular alleles of an SNP to generate a change in status of nearby portions of the genome. This may indicate the level of importance for an SNP on a particular epigenome track (omics modality) in the tissue or cell line that was used to train the SVM. Additionally or alternatively, variant dependence may be determined by identifying SNPs that alter transcription factor binding using a position weight matrix (PWM) or other algorithm for this purpose.

Target genes for permissive candidate variants may also be determined using various bioinformatics and machine learning techniques. The target genes may be identified using a quantitative trait locus (QTL) mapping to identify associations between permissive candidate variants and the expression of genes and/or omics statuses of genetic loci. Biological methods and data sets, and software analysis mapping systems for cis-eQTL, trans-eQTL, dsQTL, esQTL, hQTL, haQTL, eQTL, meQTL, pQTL, rQTL, etc. may be utilized. Permissive candidate variants may regulate the expression of genes on the same chromosome (cis-regulatory elements) or may regulate the expression genes on a different chromosome (trans-regulatory elements). However, the mapping systems may have spare samplings and false relationships. Accordingly, addition corrections are performed using machine learning techniques to fill in the sparse data.

To determine whether a functional permissive candidate variant maintains regulatory control over a nearby gene, the bioinformatics analysis may determine whether the permissive candidate variant is hypomethylated, whether the permissive candidate variant is associated with histone marks indicative of a transcription start site, and/or whether the permissive candidate variant impacts enhance RNA, promoter RNA, or other RNA.

Methods for determining long range interactions between permissive candidate variants and the genes that they regulate may include Hi-C chromatin conformation capture, ChIA-PET, chromatin immunoprecipitation sequencing (ChIP-seq), and QTL analysis. Such methods may also be used to determine target genes for permissive candidate variants. The information may be merged with QTL data and additional contacts may be detected or simulated using either the increase in information density with matrix densification methods, or other various machine learning techniques.

In any event, each permissive candidate variant may be scored and/or ranked according to its regulatory function (block 408*a*), variant dependence (block 408*b*), and target genes (block 408*c*) for a particular pharmacological phenotype. The permissive candidate variants that are scored above a threshold score and/or ranking above a threshold ranking, or other scoring or ranking criteria, may be included in the subset of intermediate candidate variants (block 410).

Then the subset of intermediate candidate variants (block 410) are scored and/or ranked with respect to each other using machine learning techniques. For example, the subset of intermediate candidate variants may be subject to a bipartite graph analysis, where the intermediate candidate variants are represented by nodes in the graph and relationships between two intermediate candidate variants are represented by edges. The intermediate candidate variants may be divided into disjoint sets where none of the members of a disjoint set have a relationship with each other. In some embodiments, the relative strength of a particular relationship between two intermediate candidate variants may be assigned a particular weight. Each intermediate candidate variant may then be scored according to the number of relationships the intermediate candidate variant has with other intermediate candidate variants from the other disjoint set. In some embodiment, each intermediate candidate variant is scored according to the aggregate weights assigned to each relationship the intermediate candidate variant has with other intermediate candidate variants.

In any event, the highest-ranking SNPs, genes, and genomic regions within the subset of intermediate candidate variants (e.g., ranked above a threshold ranking or having a score above a threshold score) may then be identified as the SNPs, genes, and genomic regions correlated with the particular pharmacological phenotype (block 414). The identified SNPs, genes, and genomic regions for the particular pharmacological phenotype may then be assayed for a current patient when predicting whether the current patient has the particular pharmacological phenotype.

When the methods 400 and 800 are executed using the server 102, and in other embodiments, data of a sensitive, proprietary, or valuable nature may be protected by the use of encryption and/or secure execution technologies, and/or the use of remote computing devices which have been subjected to additional security precautions. Such data may include patient data subject to HIPAA or other confidentiality and regulatory provisions, data subject to patient or client privilege, proprietary data of a business entity, or other such data. Such data may be encrypted for transmission and decrypted for analysis, and analyzed in an anonymized or encrypted form by the use of mathematical transforms such as hashes, elliptic curves, or other measures. In such an analysis, use may be made of Trusted Execution Technologies, Trusted Platform Modules, and other similar and analogous technologies. Use may be made of representations of the data which omit or obscure personal health information (PHI), and in particular such use may be made in the preparation and distribution of reports and diagnostic information to health care practitioners.

FIG. 4C illustrates an example gene regulatory network 470 or genomic region that includes genes and SNPs indicative of pharmacological phenotypes. The example gene regulatory network 470 may be identified using the method 400 as described above with reference to FIG. 4B and/or may be identified from a GWAS or candidate gene association studies. The gene regulatory network 470 may be within the central nervous system or any other suitable system within the human body.

In any event, the gene regulatory network 470 includes the genes BCDEF (ref. no. 472), DEFGH (ref. no. 474), ABCF (ref. no. 476), IJKLM (ref. no. 478), MNOP (ref. no. 480), LMNOP (ref. no. 482), PQRS (ref. no. 484), HIJKLM (ref. no. 486), XYZ (ref. no. 488), CDEFG (ref. no. 490), and ABCDEF (ref. no. 492).

The gene regulatory network 470 includes several noncoding SNPs that are located within introns, promoters and intergenic regions, including those associated with transcription that are significantly associated with drug X response in a particular cohort of patients. For example, SNP2 found in the BCDEF gene 472 of Chromosome 1 is indicative of a drug X response and disease risk. In another example, SNP3 which has a tight linkage disequilibrium (e.g., LD>0.8) with SNP 2 is also found in the BCDEF gene 472 of Chromosome 1 and is indicative of an adverse drug response associated with drug X. The gene regulatory network 470 also includes inter-chromosomal interactions that provide the basis for a subset of enhancer-promoter and promoter-promoter spatial interactions in trans. For example, SNP 15 found within an enhancer region of gene PQRS (ref. no. 484) within Chromosome 1 that interacts with gene HIJKLM (ref. no. 486) within Chromosome 6 is indicative of an adverse drug response associated with drug X. In some scenarios, one or more variants, genes, or enhancers in the gene regulatory network 470 may be located on a sex chromosome.

Interconnected genes within the gene regulatory network 470 are depicted in FIG. 4C using a single or double arrow (e.g., gene IJKLM (ref. no. 478) and gene LMNOP (ref. no. 482)). Each connection may include a numerical or categorical coefficient (e.g., P, C, V, T) which may be further described in a legend 494. In some embodiments, the numerical or categorical coefficient is indicative of the relationship between the interconnected genes (e.g., activation, translocation, expression, inhibition, etc.).

The example gene regulatory network 470 is merely one example of panomic data which may be obtained from GWAS, candidate gene association studies, and/or training patients to train the pharmacological phenotype prediction system 100. Additional gene regulatory networks may be obtained along with additional or alternative genomic data, epigenomic data, transcriptomic data, proteomic data, chromosomic data, or metabolomic data.

Figure 4D:
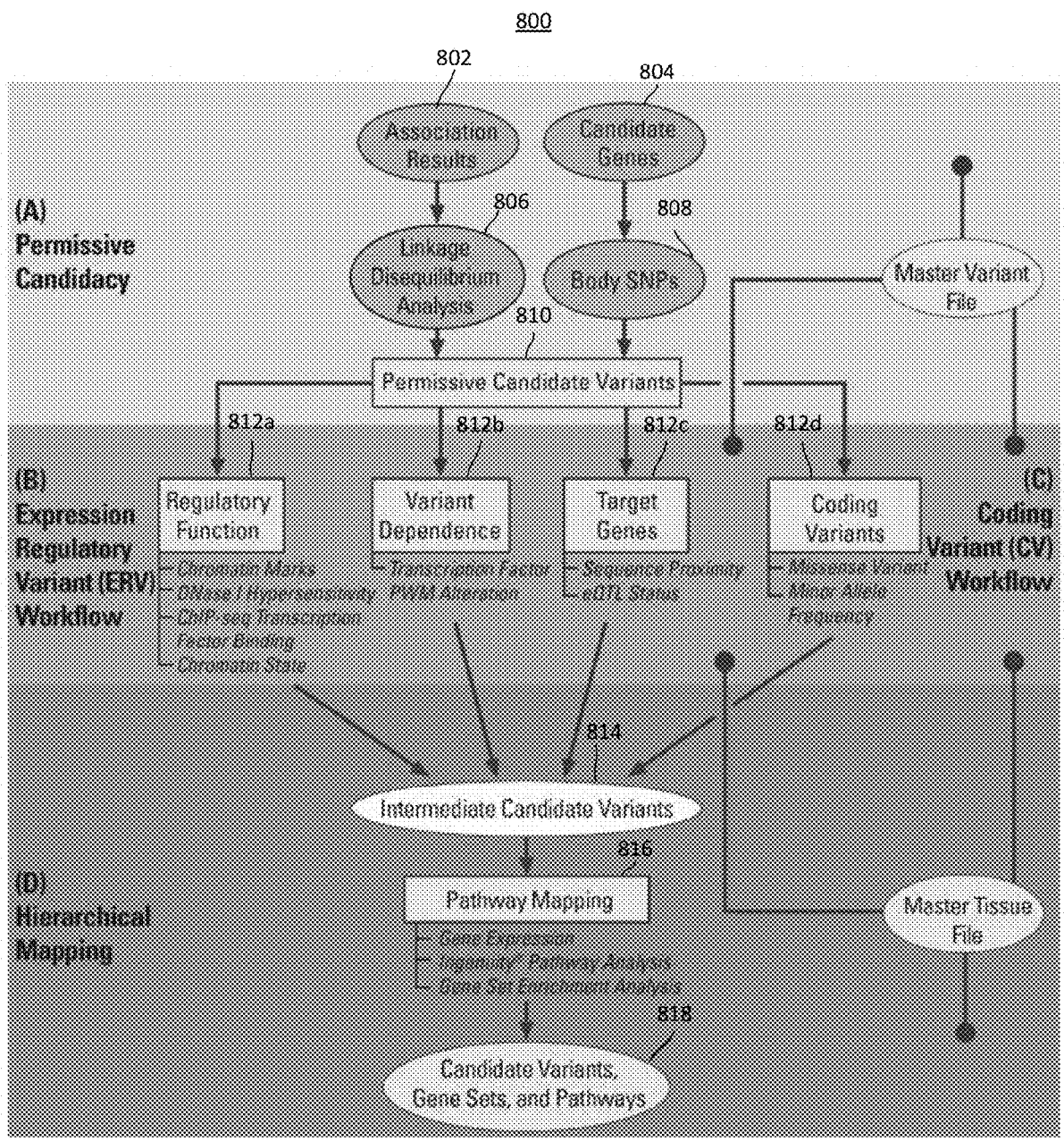
FIG. 4D is a block diagram representing another exemplary method for identifying panomic data that corresponds to a particular pharmacological phenotype using machine learning techniques in accordance with the presently described embodiments.

In addition to the method 400 described with reference to FIG. 4B, FIG. 4D illustrates another exemplary method 800 for identifying panomic data that corresponds to a particular pharmacological phenotype using machine learning techniques. The method 800 may be executed on the pharmacological phenotype assessment server 102. In some embodiments, the method 800 may be implemented in a set of instructions stored on a non-transitory computer-readable memory and executable on one or more processors on the pharmacological phenotype assessment server 102. For example, the method 800 may be performed by the training module 160 within the machine learning engine 146 of FIG. 1A.

In the method 800, permissive candidate variants (block 810) are identified in a similar manner as in the method 400 of FIG. 4B described above. More specifically, at blocks 802 and 804, for each of several noncoding or coding SNPs, genes, and genomic regions in the genome, a statistical test is performed (e.g., via GWAS or candidate gene association studies) to determine a relationship between the SNP and a particular pharmacological phenotype which may be a drug response, adverse drug response, an adverse drug event, a dosage, disease risk, etc. (e.g., a response to warfarin). When the statistical test shows a significant relationship between an SNP and the particular pharmacological phenotype (e.g., having a p-value less than a threshold probability using the null hypothesis), the SNP is determined to be correlated with the particular pharmacological phenotype. Then at block 806, a linkage disequilibrium analysis is performed on the SNPs correlated with the particular pharmacological phenotype, with other SNPs, to identify which SNPs are in linkage disequilibrium with the correlated SNPs. The linkage disequilibrium analysis may be performed by comparing the SNPs (original SNPs) to a database of SNPs (e.g., from the 1000 Genome Project) to find the SNPs linked to the original SNPs. In some embodiments, the ethnic population of the population used in the GWAS or candidate gene association study may be identified and data on a matched population may be used to find SNPs with significant linkage disequilibrium coefficients in the database of SNPs for the identified ethnic group. Body SNPs of genes of known or suspected relevance with regard to a pharmacological phenotype under investigation may also be identified (block 808).

Then the permissive candidate variants (block 810) may undergo a bioinformatics analysis to filter the permissive candidate variants into a subset of intermediate candidate variants (block 814). The method 400 of FIG. 4B filters permissive candidate variants based on their status as putative expression regulatory variants (e.g., according to regulatory function, the dependence of that regulatory function on the variant allele, and the presence of identifiable target gene relationships). In the method 800, permissive candidate variants are filtered based on expression regulatory variants (blocks 812a-812c) or coding variants (block 812d) to generate the subset of intermediate candidate variants (814). To filter based on coding variants, the method 800 determines whether the permissive candidate variants are non-synonymous coding variants with a significant minor allele frequency (e.g., a minor allele frequency of at least 0.01).

More specifically, each permissive candidate variant may be scored and/or ranked based on its expression regulatory variants (e.g., according to its regulatory function (block 812a), variant dependence (block 812b), and target genes (block 812c) for a particular pharmacological phenotype). The permissive candidate variants that are scored above a threshold expression regulatory variant score and/or ranking above a threshold expression regulatory variant ranking, or other scoring or ranking criteria, may be included in the subset of intermediate candidate variants (block 814). Additionally, each permissive candidate variant may be scored and/or ranked based on its coding variants (e.g., according to whether it is a non-synonymous coding variant with a significant minor allele frequency for a particular pharmacological phenotype). The permissive candidate variants that are scored above a threshold coding variant score and/or ranking above a threshold coding variant ranking, or other scoring or ranking criteria, may also be included in the subset of intermediate candidate variants (block 814).

Then at block 816, the intermediate candidate variants are associated with target genes, and those expressed in relevant tissues (e.g., based on genotype-tissue expression (GTEx) data) are subjected to pathway analysis, such as pathway mapping and gene set enrichment using Ingenuity® Pathway Analysis. Gene sets associated with significant and related pathways are identified, and the regulatory and coding variants influencing them are identified as candidate variants (block 818).

An example application of the method in FIG. 4D to a set of warfarin phenotypes is described with reference to FIG. 4E. Warfarin is an anticoagulant used for prevention and treatment of venous thromboembolism in cardiac disease and other contexts involving the need for coagulation control. Dose requirements vary as much as 10-fold among patients and despite the recent availability of other anticoagulants, warfarin is still commonly prescribed. Therefore, the methods described above may be utilized to predict a patient's response to warfarin and determine whether to administer warfarin or another anticoagulant to the patient as well as the dosage to administer.

Figure 4E:
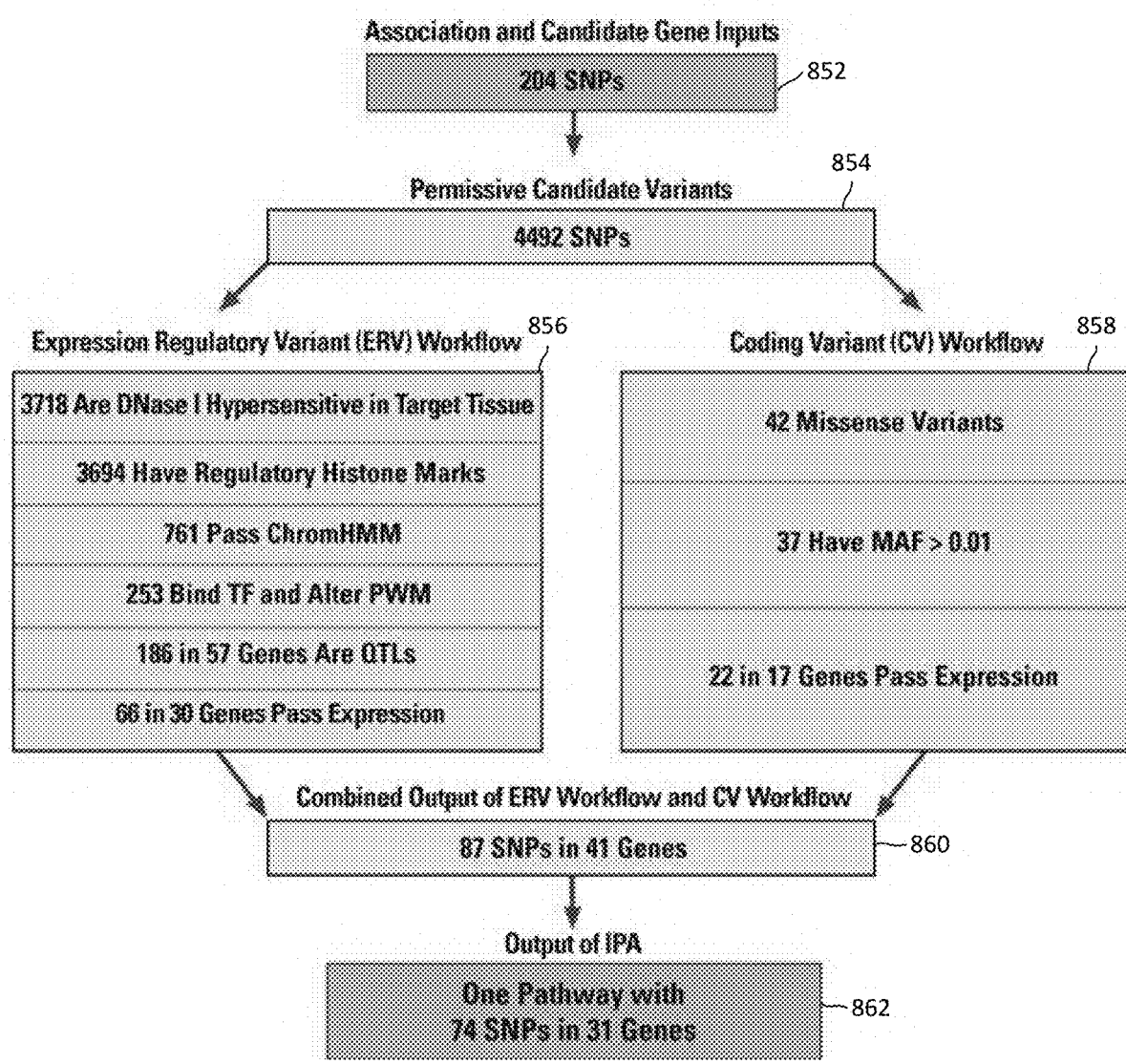
FIG. 4E is a block diagram representing the single nucleotide polymorphisms (SNPs) identified at each stage of the method described in FIG. 4D when identifying panomic data that corresponds to warfarin phenotypes.

FIG. 4E illustrates a block diagram 850 representing the single nucleotide polymorphisms (SNPs) identified at each stage of the method 800 described in FIG. 4D for identifying panomic data that corresponds to warfarin phenotypes.

To identify the association and candidate genes for the set of warfarin phenotypes, 23 GWAS are used on warfarin response and other pharmacological phenotypes of warfarin, venous thromboembolism risk, and baseline anticoagulant protein levels in healthy patients. Input data is used from populations all over the world, including European, East Asian, South Asian, African, and American cohorts. In this example, the warfarin phenotypes include several phenotype classes, such as warfarin response, ADE, and disease/background. The warfarin response class includes the warfarin phenotype: warfarin maintenance dose. The ADE class includes the warfarin phenotypes: hemostatic factors and hematological phenotypes, hemorrhaging end-stage coagulation, and thrombin generation potential phenotype. The disease/background class includes the warfarin phenotypes: venous thromboembolism, thromboembolism, thrombus, thrombosis, clotting, bleeding, C4b binding protein levels, activated partial thromboplastin time, anticoagulant levels, factor XI, prothrombin time, platelet thrombus formation. Based on these 23 GWAS as well as 23 additional variants, a total of 204 SNPs are identified as association and candidate gene inputs (block 852).

A linkage disequilibrium analysis is then performed on the 204 SNPs and body SNPs of the 204 SNPs are also identified for a total of 4492 SNPs identified as permissive candidate variants (block 854). Then, the expression regulatory variant workflow is applied to the 4492 SNPs yielding a total of 186 SNPs in 57 genes (block 856). The gene expression test of block 814 as shown in FIG. 4D, is applied to the 186 SNPs resulting in a total of 66 SNPs in 30 genes. Furthermore, the coding variant workflow is also applied to the 4492 SNPs yielding a total of 37 SNPs having a minor allele frequency of at least 0.01 (block 858). The gene expression test of block 814 as shown in FIG. 4D, is also applied to the 37 SNPs resulting in a total of 22 SNPs in 17 genes. Accordingly, the combined output of the expression regulatory variant workflow and the coding variant workflow is 87 SNPs in 41 genes (block 860). Finally, the 87 SNPs are subjected to pathway analysis to identify a single pathway with 74 SNPs in 31 genes (block 862).

Figure 4F:
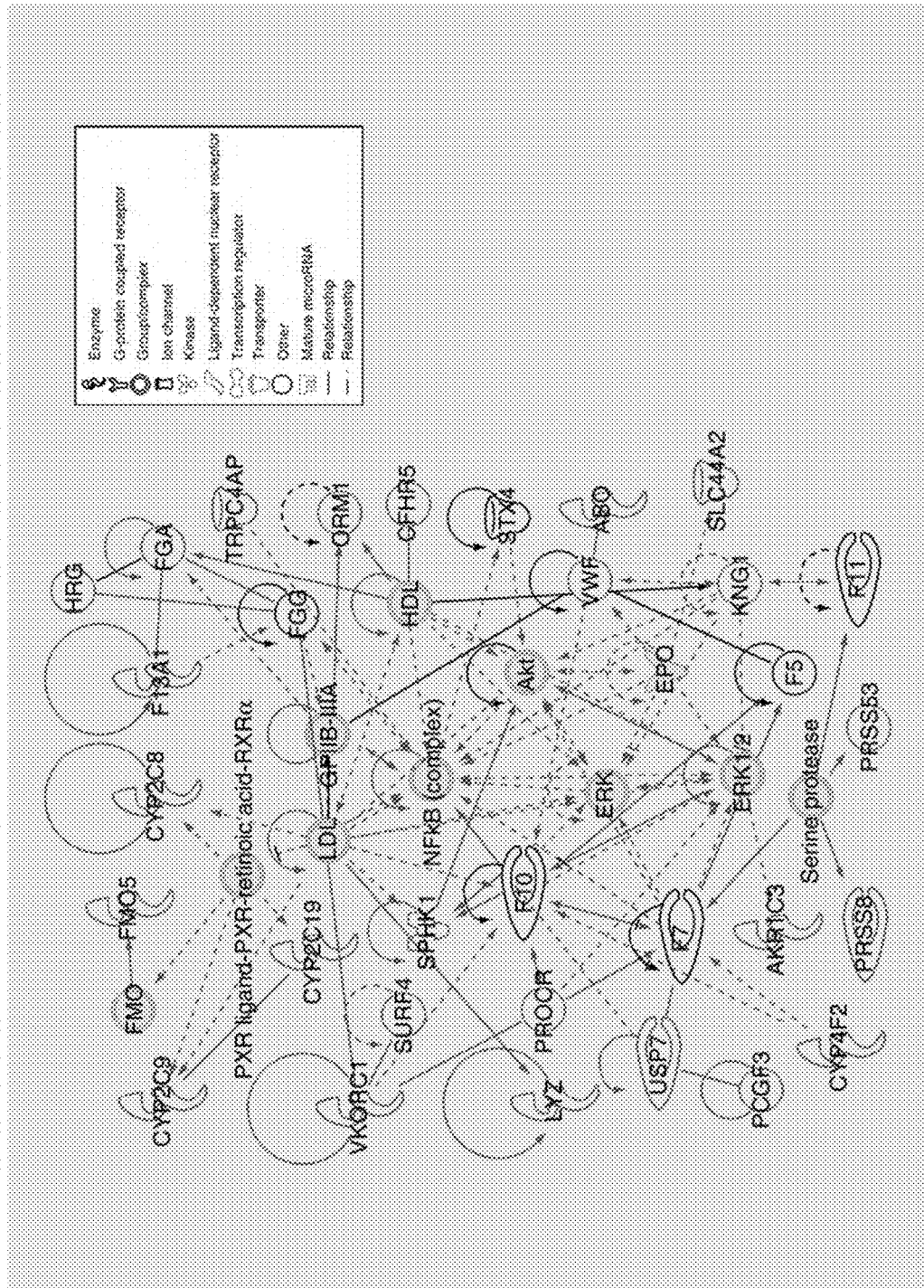
FIG. 4F depicts an exemplary warfarin response pathway in accordance with the present described embodiments.

This pathway may be referred to as the warfarin response pathway and includes genes expressed in the liver, small intestine, and vasculature. FIG. 4F illustrates an example warfarin response pathway 870 that includes genes and SNPs indicative of warfarin phenotypes. The example warfarin response pathway 870 may be identified using the method 800 as described above with reference to FIG. 4D. In any event, the warfarin response pathway includes the genes: aldo-keto reductase family 1 member C3 (AKR1C3), cytochrome P450 family 2 subfamily C member 19 (CYP2C19), cytochrome P450 family 2 subfamily C member 8 (CYP2C8), cytochrome P450 family 2 subfamily C member 9 (CYP2C9), cytochrome P450 family 4 subfamily F member 2 (CYP4F2), coagulation factor V (F5), coagulation factor VII (F7), coagulation factor X (F10), coagulation factor XI (F11), fibrinogen gamma chain (FGG), orosomucoid 1 (ORM1), serine protease 53 (PRSS53), vitamin K epoxide reductase complex subunit 1 (VKORC1), syntaxin 4 (STX4), coagulation factor XIII A chain (F13A1), protein C receptor (PROCR), von Willebrand factor (VWF), complement factor H related 5 (CFHR5), fibrinogen alpha chain (FGA), flavin containing monoxygenase 5 (FMO5), histidine rich glycoprotein (HRG), kininogen 1 (KNG1), surfeit 4 (SURF4), alpha 1-3-N-acetylgalactosaminyltransferase and alpha 1-3-galactosyltransferase (ABO), lysozyme (LYZ), polycomb group ring finger 3 (PCGF3), serine protease 8 (PRSS8), transient receptor potential cation channel subfamily C member 4 associated pattern (TRPC4AP), solute carrier family 44 member 2 (SLC44A2), sphingosine kinase 1 (SPHK1), and ubiquitin specific peptidase 7 (USP7).

The 74 SNPs (not shown) included in the 31 genes are: rs12775913 (regulatory SNP), rs346803 (regulatory SNP), rs346797 (regulatory SNP), rs762635 (regulatory SNP), and rs76896860 (regulatory SNP) included in the AKR1C3 gene (expressed in the liver); rs3758581 (coding SNP) included in the CYP2C19 gene (expressed in the liver); rs10509681 (coding SNP) and rs11572080 (coding SNP) included in the CYP2C8 gene (expressed in the liver); rs1057910 (coding SNP), rs1799853 (coding SNP), and rs7900194 (coding SNP) included in the CYP2C9 gene (expressed in the liver); rs2108622 (coding SNP) included in the CYP4F2 gene (expressed in the liver); rs6009 (regulatory SNP), rs11441998 (regulatory SNP), rs2026045 (regulatory SNP), rs34580812 (regulatory SNP), rs749767 (regulatory SNP), rs9378928 (regulatory SNP), and rs7937890 (regulatory SNP) included in the F5 gene (expressed in the liver); rs7552487 (regulatory SNP), rs6681619 (regulatory SNP), rs8102532 (regulatory SNP), rs491098 (coding SNP), and rs6046 (coding SNP) included in the F7 gene (expressed in the liver); rs11150596 (regulatory SNP) and rs11150596 (regulatory SNP) included in the F10 gene (expressed in the liver); rs2165743 (regulatory SNP) and rs11252944 (regulatory SNP) included in the F11 gene (expressed in the liver); rs8050894 (regulatory SNP) included in the FGG gene (expressed in the liver); rs10982156 (regulatory SNP) included in the ORM1 gene; rs7199949 (coding SNP) included in the PRSS53 gene (expressed in the liver);

rs2884737 (regulatory SNP), rs9934438 (regulatory SNP), rs897984 (regulatory SNP), and rs17708472 (regulatory SNP) included in the VKORC1 gene (expressed in the liver); rs35675346 (regulatory SNP) and rs33988698 (regulatory SNP) included in the STX4 gene (expressed in the small intestine); rs5985 (coding SNP) included in the F13A1 gene (expressed in the vasculature); rs867186 (coding SNP) included in the PROCR gene (expressed in the vasculature); rs75648520 (regulatory SNP), rs55734215 (regulatory SNP), rs12244584 (regulatory SNP), and rs1063856 (coding SNP) included in the VWF gene (expressed in the vasculature); rs674302 (regulatory SNP) included in the CFHR5 gene (expressed in the liver); rs12928852 (regulatory SNP) and rs6050 (coding SNP) included in the FGA gene (expressed in the liver); rs8060857 (regulatory SNP) and rs7475662 (regulatory SNP) included in the FMO5 gene (expressed in the liver); rs9898 (coding SNP) included in the HRG gene (expressed in the liver); rs710446 (coding SNP) included in the KNG1 gene (expressed in the liver); rs11577661 (regulatory SNP) included in the SURF4 gene (expressed in the liver); rs11427024 (regulatory SNP), rs6684766 (regulatory SNP), rs2303222 (regulatory SNP), rs1088838 (regulatory SNP), rs13130318 (regulatory SNP), and rs12951513 (regulatory SNP) included in the ABO gene (expressed in the small intestine); rs8118005 (regulatory SNP) included in the LYZ gene (expressed in the small intestine); rs76649221 (regulatory SNP), rs9332511 (regulatory SNP), and rs6588133 (regulatory SNP) included in the PCGF3 gene (expressed in the small intestine); rs11281612 (regulatory SNP) included in the PRSS8 gene (expressed in the small intestine); rs11589005 (regulatory SNP), rs8062719 (regulatory SNP), rs889555 (regulatory SNP), rs36101491 (regulatory SNP), rs7426380 (regulatory SNP), rs6579208 (regulatory SNP), rs77420750 (regulatory SNP), and rs73905041 (coding SNP) included in the TRPC4AP gene (expressed in the small intestine); rs3211770 (regulatory SNP), rs3211770 (regulatory SNP), rs3087969 (coding SNP), and rs2288904 (coding SNP) included in the SLC44A2 gene (expressed in the vasculature); rs683790 (regulatory SNP) and rs346803 (coding SNP) included in the SPHK1 gene (expressed in the vasculature); and rs201033241 (coding SNP) included in the USP7 gene (expressed in the vasculature).

In addition to warfarin, the methods described in FIGS. 4B and 4D may also be applied to a set of lithium phenotypes as well as any other pharmacological phenotypes. By applying the methods described in FIGS. 4B and 4D to lithium phenotypes, a lithium response pathway is identified with 78 SNPs in 12 genes. The lithium response pathway includes the genes: ankyrin 3 (ANK3), aryl hydrocarbon receptor nuclear translocator like (ARNTL), calcium voltage-gated channel auxiliary subunit gamma 2 (CACNG2), calcium voltage-gated channel subunit alpha1 C (CACNA1C), cyclin dependent kinase inhibitor 1A (CDKN1A), cAMP responsive element binding protein 1 (CREB1), glutamate inotropic receptor AMPA type subunit 1 (GRIA2), glycogen synthase kinase 3 beta (GSK3B), nuclear receptor subfamily 1, group D, member 1 (NR1D1), solute carrier family 1 member 2 (SLC1A2), 5-hydroxytryptamine receptor 1A (HTR1A), and TRAF2 and NCK interacting kinase (TNIK). The 78 SNPs included in the 12 genes are: rs2185502, rs10821792, rs1938540, rs3808943, rs61847646, rs75314561, rs61846516, rs10994397, rs10994318, rs61847579, rs12412727, rs10994308, rs4948418, rs4948412, rs4948413, rs4948416, rs10821745, rs10994336, rs10994360, rs9633532, rs1938526, rs10994322, and rs10994321 included in the ANK3 gene; rs10766075, rs7938308, rs10832017, rs4603287, rs7934154, rs12361893, rs4414197, rs4757140, rs4757141, rs61882122, rs11022755, rs11022754, rs1481892, rs1481891, rs4353253, rs4756764, rs2403662, rs4237700, rs10832018, rs12290622, rs7928655, rs34148132, rs4146388, rs4146387, rs7949336, rs4757139, rs7107287, and rs1351525 included in the ARNTL gene; rs2284017 and rs2284016 included in the CACNG2 gene; rs2007044 and rs1016388 included in the CACNA1C gene; rs3176336, rs3176333, rs3176334, rs3176320, rs4135240, rs2395655, and rs733590 included in the CDKN1A gene; rs10932201 included in the CREB1 gene; rs78957301 included in the GRIA2 gene; rs334558 included in the GSK3B gene; rs2314339 included in the NR1D1 gene; rs3794088, rs3794087, rs4354668, rs12418812, rs1923294, rs5791047, rs111885243, rs752949, and rs16927292 included in the SLC1A2 gene; rs6449693 and rs878567 included in the HTR1A gene; and rs7372276 included in the TNIK gene.

Figure 4G:
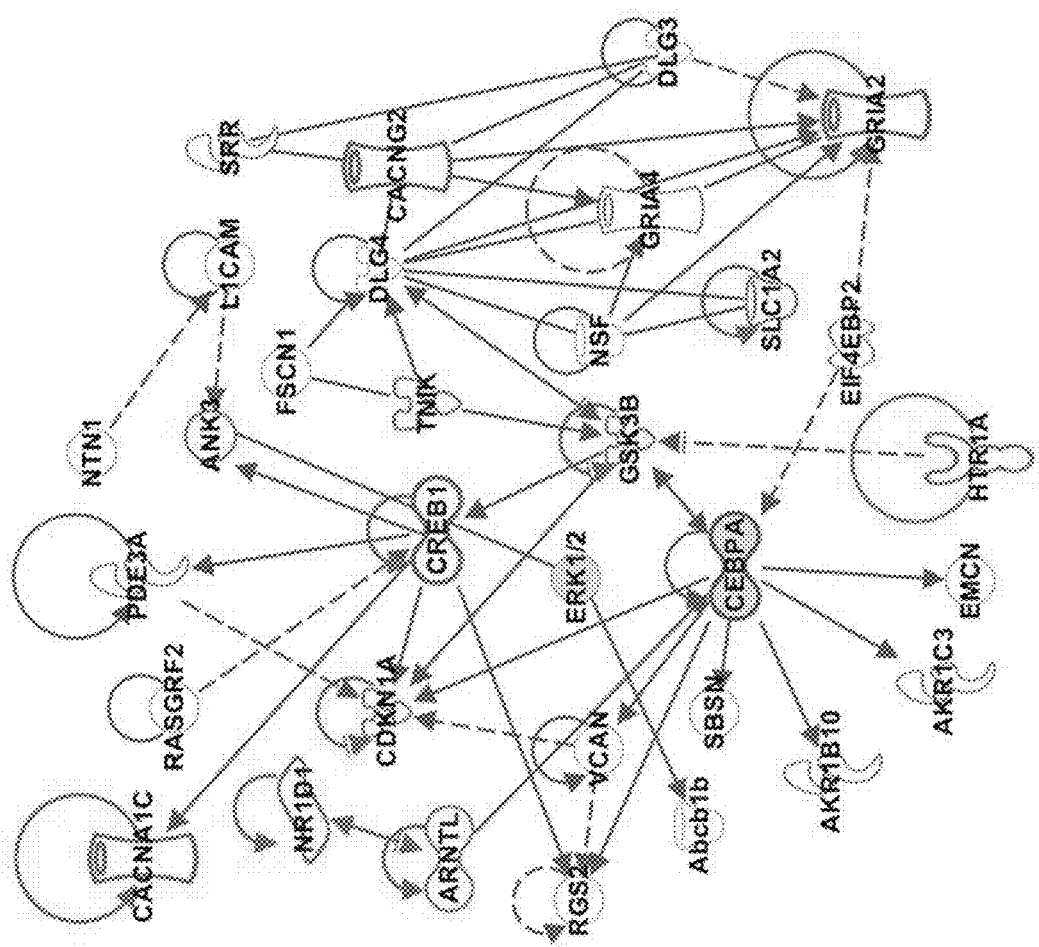
FIG. 4G depicts an exemplary lithium response pathway in accordance with the present described embodiments.

The lithium response pathway 890 described above is depicted in FIG. 4G. Lithium is a psychiatric drug used to treat mental illnesses/disorders. The methods described above may be utilized to predict a patient's response to lithium and determine whether to administer lithium or another psychiatric drug to the patient as well as the dosage to administer. In any event, the example lithium response pathway 890 may be identified by using the methods 400, 800 described in FIGS. 4B and 4D. Each of the genes in the lithium response pathway 890 is expressed in a portion of the brain including the frontal lobe, insula, temporal cortex, cingulate cortex, amygdala, hippocampus, anterior caudate, thalamus, motor cortex, fusiform cortex, substantia nigra, cerebellum, and hypothalamus.

In some embodiments, the pharmacological phenotype prediction system 100 may test for the presence of the identified SNPs, genes, and genomic regions in a current patient to determine whether the current patient has the particular pharmacological phenotype. For example, identified SNPs, genes, and genomic regions may be indicative of a negative response to valproic acid for treating TBI. When a current patient has a TBI, the current patient's biological sample may be provided and analyzed for the presence of the identified SNPs, genes, and genomic regions for example, using the process 500 for generating panomic data as described above with respect to FIG. 5. When the current patient has at least some of the identified SNPs, genes, and genomic regions indicative of a negative response to valproic acid, the current patient is not administered valproic acid. In other embodiments, identified SNPs, genes, and genomic regions are scored, combined, and/or weighted in any suitable manner for determining which combinations are indicative of a negative response to valproic acid. Then the scoring or weighting system is applied to the SNPs, genes, and genomic regions in the current patient's biological sample to determine whether the current patient has a combination indicative of a negative response to valproic acid.

In any event, the pharmacological phenotype prediction system 100 may provide the identified SNPs, genes, and genomic regions indicative of a particular pharmacological phenotype as panomic data for the pharmacological phenotype. The machine learning engine 146 may obtain the panomic data with sociomic, physiomic and environmental data for training patients having at least some of the identified SNPs, genes, and genomic regions as well phenomic data for the training patients. In this manner, the machine learning engine 146 may classify the training patients having the identified SNPs, genes, and genomic regions indicative of the particular pharmacological phenotype (e.g., a negative response to ketamine for treating depression) as having the particular pharmacological phenotype or not having the pharmacological phenotype. Then the sociomic, physiomic and environmental data may be used to differentiate training patients having the identified SNPs, genes, and genomic regions who do have the particular pharmacological phenotype from training patients having the identified SNPs, genes, and genomic regions who do not have the particular pharmacological phenotype.

For example, when the machine learning technique is decision trees, a decision tree may be generated that includes several nodes each representing a test on a current patient's data. The nodes may be connected by branches each representing the outcome of a test or other measurement or observable/recordable status (e.g., a "Yes" branch and a "No" branch), where the branches may be weighted and a leaf node may indicate the presence of a pharmacological phenotype in the current patient. In other embodiments, the leaf node indicates a likelihood of the pharmacological phenotype as determined by aggregating or combining the weighted branches for example, or the leaf node may indicate a score that may be compared to a threshold to determine whether the current patient has the pharmacological phenotype. In any event, the decision tree may be generated such that nodes near the top of the tree represent tests on the current patient's panomic data, for example as indicated by the identified SNPs, genes, and genomic regions. When the current patient has a suitable combination of the identified SNPs, genes, and genomic regions indicative of the particular pharmacological phenotype (e.g., a negative response to ketamine for treating depression), the decision tree branches to several nodes that represent tests on the current patient's sociomic, physiomic and environmental data.

In another example, when the machine learning technique is SVM, for each training patient the pharmacological phenotype assessment server 102 obtains sociomic, physiomic and environmental data, the training patient's identified SNPs, genes, and genomic regions indicative of the particular pharmacological phenotype, and an indication of whether or not the training patient has the particular pharmacological phenotype (e.g., a negative response to ketamine for treating depression) as a training vector. A SVM obtains each of the training vectors and creates a statistical model for determining whether or not a current patient has a particular pharmacological phenotype by generating a hyperplane that separates a first subset of the training vectors corresponding to training patients who have the pharmacological phenotype and a second subset of the training vectors corresponding to training patients who do not have the pharmacological phenotype.

Environmental, physiomic and sociomic data may be obtained for a training patient or cohort of training patients having the identified SNPs, genes, and genomic regions indicative of the particular pharmacological phenotype. More specifically, the training module 160 may obtain, for example from the client device 106-116 and/or one or several servers (e.g., an EMR server, a polypharmacy server, etc.), a set of training data that may include panomic data and sociomic, physiomic and environmental data for several training patients where the pharmacological phenotypes to the training patients are known (e.g., previously or currently determined) and also provided in the training data. Environmental, physiomic and sociomic data may include clinical data, demographic data, polypharmacy data, socioeconomic data, education data, substance abuse data, diet and exercise data, law enforcement data, circadian data, household data, or any other suitable data indicative of a patient's sociological circumstances or environmental conditions.

In an exemplary scenario, panomic, phenomic, sociomic, physiomic and environmental data for a training patient is collected over a first time period (e.g., one year). While the patient may be a training patient, results of the pharmacological phenotype prediction system 100 may also be determined based on the patient's panomic, phenomic, sociomic, physiomic and environmental data. As mentioned above, a training patient having training data used to train the pharmacological phenotype prediction system 100 may also become a current patient for predicting the training patient's unknown pharmacological phenotypes. In this example, the panomic, phenomic, sociomic, physiomic and environmental data may be collected from January-December of Year 1. While the panomic, phenomic, sociomic, physiomic and environmental data may be for a single training patient, panomic, phenomic, sociomic, physiomic and environmental data may be collected for a cohort of training patients. For example, the panomic, phenomic, sociomic, physiomic and environmental data may be collected for a cohort of training patients each having the identified SNPs, genes, and genomic regions indicative of a negative response to drug X for treating illness Y.

The panomic, phenomic, sociomic, physiomic and environmental data may include individual/cohort and population panomics and pharmacometabolomics 302, exposome 304, sociomics, demographics, and stress/trauma 306, and medical physiomics, EHRs, laboratory values, stress and abuse factors and trauma, and medical outcomes data 308 as shown in FIG. 2. However, these are merely a few examples of panomic, phenomic, sociomic, physiomic and environmental data which may be obtained from training patients to train the pharmacological phenotype assessment server 102. Additional sociomic, physiomic and environmental data such as circadian data indicative of the training patient's sleep and other recurring lifestyle temporal patterns may also be included.

The panomics and pharmacometabolomics data may be the result of a pharmacogenomics assay of the training patient's biological sample. The exposome data in Year 1 may include the training patient's employment status and place of residence in August of Year 1.

The medical physiomics, EHRs, laboratory values, stress and abuse factors and trauma, and medical outcomes data may indicate the training patient's law enforcement experiences from January-December of Year 1.

The medical physiomics, EHRs, laboratory values, stress and abuse factors and trauma, and medical outcomes data may also include polypharmacy data including the drugs prescribed to the training patient and when they are prescribed. For example, the training patient is prescribed drug A to treat illness 1, drug B to treat illness 2, and drug C to treat illness 3 in March of Year 1, and drug D to treat illness 4 in August of Year 1. The training patient is also tapered off drug C in August of Year 1. Additionally, the medical physiomics, EHRs, laboratory values, stress and abuse factors and trauma, and medical outcomes data may include phenomic data indicative of the training patient's pharmacological phenotypes such as illnesses that the training patient is diagnosed with. For example, in January of Year 1 the training patient is diagnosed with illnesses 1-3.

Moreover, the data may include additional phenomic data such as information describing the efficacy and/or adverse effects of the drugs. For example, the training patient may experience side effects of drug C and accordingly the training patient may be tapered off drug C after experiencing these side effects. The training patient may also experience a positive response to taking drug C which may be indicative of the efficacy of the drug for the training patient.

The sociomics and demographics data may indicate the status of the training patient's household. For example, the sociomics and demographics data may indicate the training patient's marital status and number of children in January of Year 1. The sociomics and demographics data may also indicate the amount of income for the training patient from January-December of Year 1. The sociomics and demographics data may also indicate available information on family members who are or were affected and unaffected by the relevant diseases and comorbidities, as well as their treatment responses and other pharmacological phenotypes.

In this exemplary scenario, the panomic, phenomic, sociomic, physiomic and environmental data may also include data from the training patient collected from January-December of Year 2. In Year 2, the panomics and pharmacometabolomics data includes proteomics and transcriptomics for the training patient obtained in March and the results of a pharmacogenomics assay obtained in August.

The panomics and pharmacometabolomics data in Year 2 may include the results of an inpatient metabolic panel on the training patient in March of Year 2 indicating the presence of toxic metabolites of drug B. The panomics and pharmacometabolomics data may also include the results of another inpatient metabolic panel on the training patient in August of Year 2 indicating normal blood levels of drug E.

The medical physiomics, EHRs, laboratory values, stress and abuse factors and trauma, and medical outcomes data in Year 2 indicates the results of various mental health, substance abuse, and stress and trauma questionnaires administered to the training patient.

The medical physiomics, EHRs, laboratory values, stress and abuse factors and trauma, and medical outcomes data in Year 2 also indicates that the training patient experiences a negative response to drug C in February and subsequently discontinues taking drug C. The training patient is instead prescribed drug F in March of Year 2 and drug E in August. The training patient then experiences a positive response to taking drugs E and F which may be indicative of the efficacy of the drugs for the training patient.

Also, in response to detecting the presence of toxic metabolites of drug B as indicated by the training patient's panomics and pharmacometabolomics data, the training patient discontinues taking drug B in March of Year 2. The medical physiomics, EHRs, laboratory values, stress and abuse factors and trauma, and medical outcomes data further indicates that the training patient's illness 1 diagnosis becomes controlled in April of Year 2 and the drug A dosage is reduced. The sociomics and demographics data in Year 2 also indicates the amount of income for the training patient from January-December of Year 2.

The information included in the panomic, phenomic, sociomic, physiomic and environmental data for Years 1 and 2 may be used to train the pharmacological phenotype assessment server 102 to generate the statistical model. Similar information may be collected for several training patients (e.g., tens, hundreds, thousands) including cohorts or populations of training patients in conjunction with panomic data to generate the statistical model. In the generation of such a statistical model, important features may be identified, and a model generated which uses this restricted set of information, in order to allow current patient phenotypes to be predicted with a limited set of information.

For example, as mentioned above, the panomic, phenomic, sociomic, physiomic and environmental data may be obtained for a cohort of training patients each having the identified SNPs, genes, and genomic regions indicative of a negative response to drug X for treating illness Y. The training module 160 may classify a first subset of the panomic, phenomic, sociomic, physiomic and environmental data (e.g., identified SNPs, genes, and genomic regions for the cohort of training patients indicative of a negative response to drug X for treating illness Y) as corresponding to training patients who have a negative response to drug X and may classify a second subset of the panomic, phenomic, sociomic, physiomic and environmental data as corresponding to training patients who do not have a negative response to drug X. In some embodiments, the training module 160 may perform statistical measures on the subsets of panomic, phenomic, sociomic, physiomic and environmental data for each classification (training patients who have a negative response to drug X and training patients who do not have a negative response to drug X). For example, the training module 160 may determine an average income for training patients corresponding to each classification, an average ACE score, etc.

Then the training module 160 may generate a statistical model (e.g., a decision tree, neural network, hyperplane, linear or nonlinear regression coefficients, etc.) for predicting whether a current patient will have a negative response to drug X for treating illness Y based on the statistical measures for each classification. For example, the statistical model may be a decision tree having several nodes connected by branches where each node represents a test on panomic data related to the identified SNPs, genes, and genomic regions indicative of a negative response to drug X for treating illness Y. The branches may include weights or scores for different SNPs, genes, and genomic regions and when a current patient has a combined weight or score that exceeds a threshold, this may indicate that the current patient has a combination of SNPs, genes, and genomic regions that are indicative of a negative response to drug X.

The decision tree may further include several nodes connected by branches where each node represents a test on sociomic, physiomic and environmental data. A first node may test whether a current patient's income >$20,000 a year which is connected by a "Yes" branch to a second node that tests whether the current patient's ACE score>5, which is connected by a "Yes" branch to a third node that tests whether the current patient has experienced domestic violence, which is connected by a "No" branch to a leaf node that predicts whether the current patient will have a negative response to drug X. The leaf branch may indicate a likelihood that the current patient will have a negative response to drug X that may be determined based on the outcomes of each test at the respective nodes and/or weights assigned to the corresponding branches. In some embodiments, the leaf branch may indicate a response score to drug X that may also be determined based on the outcomes of each test at the respective nodes and/or weights assigned to the corresponding branches. The response score may be indicative of the efficacy of the drug on treating the corresponding illness discounted for adverse effects of the drug on the patient.

As described in this exemplary scenario, the panomic, sociomic, physiomic and environmental data may be combined for each of several training patients along with indications of pharmacological phenotypes for the training patients (e.g., illnesses that the training patient is diagnosed with, responses to drugs, substance abuse problems) to generate the statistical model for predicting pharmacological phenotypes for current patients. In some embodiments, the panomic, sociomic, physiomic and environmental data for the training patients may be combined with panomic and/or genomic data from previous studies such as GWAS to identify relationships between genes, transcription factors, proteins, metabolites, chromatin states, environment, and pharmacological phenotypes for patients.

In any event, the panomic, sociomic, physiomic and environmental data for each training patient are combined to generate the statistical model. In some embodiments, the panomic, sociomic, physiomic and environmental data for a training patient may be classified as corresponding to a training patient diagnosed with a particular illness (or not diagnosed with the particular illness), classified as corresponding to a training patient suffering from substance abuse problems (or not suffering from substance abuse problems), classified as corresponding to a training patient having a particular response to a drug, or classified in any other suitable manner. In some scenarios, panomic, sociomic, physiomic and environmental data for the same training patient may be segmented into multiple pharmacological phenotypes at different periods of time. For example, a training patient's panomic data may be altered over time as the sociomic, physiomic and environmental data changes for the training patient and at a first time period the training patient may suffer from one mental illness while at a second time period the training patient suffers from another mental illness.

Also in some embodiments, the panomic, sociomic, physiomic and environmental data for training patients may be classified according to demographics. For example, panomic, sociomic, physiomic and environmental data for training patients of European ancestry may be assigned to one cohort while panomic, sociomic, physiomic and environmental data for training patients of Chinese ancestry may be assigned to another cohort. In another example, panomic, sociomic, physiomic and environmental data for training patients between the ages of 25 and 35 may be assigned to one cohort while panomic, sociomic, physiomic and environmental data for training patients between the ages of 35 and 45 may be assigned to another cohort.

In such embodiments, the training module 160 may generate different statistical models for each pharmacological phenotype and/or for each cohort (e.g., separated based on demographics). For example, a first statistical model may be generated for determining a likelihood that a current patient will experience substance abuse problems, a second statistical model may be generated for determining a risk of one type of illness, a third statistical model may be generated for determining a risk of another type of illness, a fourth statistical model may be generated for determining a likelihood of a negative response to a particular drug, etc. In other embodiments, the training module 160 may generate a single statistical model for determining a likelihood that a current patient has any of the pharmacological phenotypes, or may generate any number of statistical models for determining a likelihood that a current patient has any number of the pharmacological phenotypes.

Once the panomic, sociomic, physiomic and environmental data are classified into subsets corresponding to various cohorts and/or pharmacological phenotypes, the panomic, sociomic, physiomic and environmental data for a particular pharmacological phenotype may be analyzed to generate the statistical model. The statistical model may be generated using neural networks, deep learning, decision trees, support vector machines, or any of the machine learning methods mentioned above. For example, the panomic, sociomic, physiomic and environmental data for training patients of European ancestry may be analyzed to determine that there is a high correlation between training patients having the SNP 2 found in the XYZ gene, unemployment, a violent criminal record, and suffering from schizophrenia. Accordingly, patients of European ancestry having the SNP 2 found in the XYZ gene, unemployment, and a violent criminal record may be at a high risk of schizophrenia.

When the machine learning technique is neural networks or deep learning, the training module 160 may generate a graph having input nodes, intermediate or "hidden" nodes, edges, and output nodes. The nodes may represent a test or function performed on panomic, sociomic, physiomic or environmental data and the edges may represent connections between nodes. In some embodiments, the output nodes may include indications of pharmacological phenotypes or likelihoods of pharmacological phenotypes. In some embodiments, the edges may be weighted according to a strength of the test or function for the preceding node in determining the pharmacological phenotypes.

Accordingly, the type of panomic, sociomic, physiomic or environmental data for preceding nodes having higher weights may be more important to the pharmacological phenotype determination than the type of panomic, sociomic, physiomic or environmental data for preceding nodes having lower weights. By identifying the most important panomic, sociomic, physiomic or environmental data, the training module 160 may eliminate panomic, sociomic, physiomic or environmental data from the statistical model that is the least important and may be misleading and/or random noise. Additionally, the most important panomic data for a pharmacological phenotype (as determined by ranking, weighting, or scoring the panomic data above a threshold) may be used to enable selection of the types of panomic data to assay for a patient's biological sample.

For example, a neural network may include four inputs nodes representing panomic, sociomic, physiomic and environmental data that are each connected to several hidden nodes. The hidden nodes are then connected to an output node that indicates a likelihood that a current patient will suffer from bipolar disorder. The connections may have assigned weights and the hidden nodes may include tests or functions performed on the panomic, sociomic, physiomic and environmental data. In some embodiments, the tests or functions may be distributions as determined by the training data or previous studies such as GWAS. For example, patients having a particular SNP and in the $98^{th}$ percentile of an income distribution may be at lower likelihood for illness Y than patients having the same SNP and in the $10^{th}$ percentile of the income distribution.

In some embodiments, the hidden nodes may be connected to several output nodes each indicating a likelihood that a current patient will suffer from a different illness, a likelihood that a current patient will have substance abuse problems, and/or a likelihood or response score for a current patient with respect to a particular drug. In this example, the four input nodes may include the patient's ancestry, the patient's current income and/or changes in the patient's income over the previous year, the presence of the SNP 13 in the patient's LMNOP gene, and poor sleep patterns for the patient.

In some embodiments, each of the four input nodes may assign a numerical value to the patient's panomic, sociomic, physiomic or environmental data and tests or functions may be applied to the numerical values at the hidden nodes. Then the results of the tests or functions may be weighted and/or aggregated to determine a response score to lithium for example. The response score may be indicative of the efficacy of the drug on treating the corresponding illness discounted for adverse effects of the drug on the patient. In this example, the response score for lithium may be high (e.g., 80 out of 100) indicating that patient will respond positively when taking lithium to treat bipolar disorder. Accordingly, a health care provider may prescribe lithium to treat the patient's bipolar disorder. In some embodiments, the response score for lithium to treat bipolar disorder may be compared to the response score for other prescriptions drugs to treat bipolar disorder. Then the drugs may be ranked according to their respective response scores and the highest-ranking drug may be recommended for the health care provider to prescribe to the patient. However, this is merely one example of the inputs and resulting output of the statistical model for determining phenotypes. In other examples, any number of input nodes may include several types of panomic data, sociomic data and environmental data for a patient. Additionally, any number of output nodes may determine likelihoods or risks of suffering from different illnesses, a likelihood of substance abuse problems, likelihoods of comorbidities, etc.

As additional training data is collected, the weights, nodes, and/or connections may be adjusted. In this manner, the statistical model is constantly or periodically updated to reflect at least a near real-time representation of the sociomic, physiomic, environmental and panomic data.

In some embodiments, the machine learning techniques may be used to identify cohorts or demographic markers for classifying patients as having or not having a particular pharmacological phenotype. As in the example above, the tests or functions included in the hidden nodes may be developed by performing statistical measures on the sociomic, physiomic and environmental data for first and second subsets of the training patients having and not having a particular pharmacological phenotype, respectively. The statistical measures may be used to identify the most significant variables included in the training patients' sociomic, physiomic and environmental data for distinguishing between training patients who have the pharmacological phenotype and training patients who do not have the pharmacological phenotype. In this manner, the tests or functions included in the hidden nodes are not necessarily known a priori.

After the statistical model is generated using machine learning techniques as described above (e.g., neural networks, deep learning, decision trees, support vector machines, etc.), the training module 160 may test the statistical model using test panomic, sociomic, physiomic and environmental data from a test patient along with the pharmacological phenotypes of the test patient. The test patient may be a patient where his/her pharmacological phenotypes are known. However, for purposes of testing, the training module 160 may determine the likelihood that the test patient has various pharmacological phenotypes by comparing the test patient's test panomic, sociomic, physiomic and environmental data to the statistical model generating using machine learning techniques.

For example, the training module 160 may traverse nodes from the neural network using the test panomic, sociomic, physiomic and environmental data for the test patient. When the training module 160 reaches an outcome node indicative of a likelihood or response score for a particular pharmacological phenotype, the likelihood or response score may be compared to the known test patient pharmacological phenotype.

In some embodiments, if the likelihood that the test patient has a particular pharmacological phenotype (e.g., illness Y) is above 0.5 and the known test patient pharmacological phenotype is that she did suffer from illness Y, the determination may be deemed correct. In another example, if the response score is the highest for a drug that the test patient had a strong response to without harmful side effects, the determination may be deemed correct. In other embodiments, the likelihood may have to be above 0.7 when the known test patient pharmacological phenotype is that she has a particular pharmacological phenotype, or some other predetermined threshold for the determined likelihood to be deemed correct.

Moreover, in some embodiments, when the training module 160 is correct more than a predetermined threshold amount of the time, the statistical model may be presented to the phenotype assessment module 162. On the other hand, if the training module 160 is not correct more than the threshold amount, the training module 160 may continue obtaining sets of training data for further training.

Once the statistical model has been adequately tested to verify its accuracy, the phenotype assessment module 162 may obtain the statistical model. Based on the statistical model, the phenotype assessment module 162 may determine the likelihood a current patient has various pharmacological phenotypes. The phenotype assessment module 162 may obtain panomic, sociomic, physiomic and environmental data for a current patient where it is unknown whether the current patient has certain pharmacological phenotypes. The sociomic, physiomic and environmental data may be collected at several points in time and may be similar to the sociomic and environmental data collected for a training patient as described in the exemplary scenario mentioned above.

More specifically, the sociomic, physiomic and environmental data may include clinical data such as the medical history of the current patient including illnesses the current patient has been diagnosed with, results of laboratory tests, and procedures performed on the patient, a family history for the current patient, etc. The sociomic, physiomic and environmental data may also include polypharmacy data such as each of the drugs prescribed to the current patient over a particular time period, the duration of each prescription, the number of refills, whether the current patient has been refilling each drug on time, etc. Additionally, the sociomic, physiomic and environmental data may include demographic data such as the ancestry or ethnicity of the current patient, the age of the current patient, the weight of the current patient, the gender of the current patient, the place of residence for the current patient, etc. Furthermore, the sociomic, physiomic and environmental data may include socioeconomic data for the current patient such as the amount of income for the current patient and/or sources of the income, education data (e.g., high school diploma, GED, college graduate, master's degree, etc.), and diet and exercise data indicating how often the current patient exercises, the current patient's eating habits, an amount of weight gain or weight loss over a particular time period, etc. Still further, the sociomic, physiomic and environmental data may include household data such as the current patient's marital status, number of children, and family members currently living with the current patient, law enforcement data indicating a criminal record of the current patient and whether the current patient has been the victim of abuse or other crimes, substance abuse data indicating whether the current patient suffers or has suffered from substance abuse problems, and circadian data indicating sleep patterns for the current patient.

In addition to sociomic, physiomic and environmental data, the phenotype assessment module 162 may obtain panomic data for the current patient. The panomic data may be similar to the panomic data as shown in FIG. 4C. More specifically, the panomic data may include genomic data indicative of genetic traits, epigenomic data indicative of gene expression, transcriptomic data indicative of DNA transcription, proteomic data indicative of proteins expressed by a genome, choromosomic data indicative of chromatin states in a genome, and/or metabolomic data indicative of metabolites in a genome.

Then the phenotype assessment module 162 may apply the panomic, sociomic, physiomic and environmental data for the current patient to the statistical model to determine likelihoods that the current patient has various pharmacological phenotypes. When several statistical models are generated, the phenotype assessment module 162 may apply the panomic, sociomic, physiomic and environmental data for the current patient to each of the statistical models to determine likelihoods that the current patient will suffer from illness Y, will have substance abuse problems, and will experience comorbidity for example.

In some embodiments, the health care provider may provide a request for a particular type of pharmacological phenotype, such as the current patient's predicted response to a particular drug or for an optimal drug to treat a particular illness. Accordingly, the phenotype assessment module 162 may apply the statistical model or a portion of the statistical model that is generated to respond to the health care provider's request. Then the health care provider may receive an indication of the optimal drug and dosage for treating the particular illness from the pharmacological phenotype assessment server 102.

In other embodiments, the pharmacological phenotype assessment server 102 may evaluate the panomic, sociomic, physiomic and environmental data by applying the current patient's panomic, sociomic, physiomic and environmental data to the statistical model to determine likelihoods or response scores for each of several pharmacological phenotypes. The pharmacological phenotype assessment server 102 may then generate a risk analysis display for the current patient's health care provider to review.

The risk analysis display may include indications of patient biographical information such as the patient's name, date of birth, address, etc. The risk analysis display may also include indications of each of the likelihoods or other semi-quantitative and quantitative measures of various pharmacological phenotypes which may be represented as a probability (e.g., 0.6), a percentage (e.g., 80 percent), a category from a set of categories (e.g., "High risk," "Medium risk," or "Low risk"), or in any other suitable manner. Additionally, the risk analysis display may include indications of response scores to drugs which may be numerical (e.g., 75 out of 100), categorical (e.g., "Strong response," "Poor response," etc.), or represented in any other suitable manner. Additionally, each of the likelihoods or response scores may be displayed with a description of the corresponding pharmacological phenotype (e.g., "High risk of illness Y"). Such risk factors and levels may be stored and processed in a quantitative or semi-quantitative form in the context of the internal workings of the statistical model, but may be translated into qualitative terms for output to care providers and patients.

In some embodiments, the pharmacological phenotype assessment server 102 may compare a likelihood of a pharmacological phenotype to a likelihood threshold (e.g., 0.5) and may include the pharmacological phenotype in the risk analysis display when the likelihood of the pharmacological phenotype exceeds the likelihood threshold. For example, only illnesses that are high risk for the current patient may be included in the risk analysis display. In another example, the risk analysis display may include an indication that the current patient is likely to suffer from substance abuse problems when the likelihood of substance abuse problems for the current patient exceeds a likelihood threshold. In this manner, the health care provider may recommend or provide early intervention to the current patient. Also in some embodiments, response scores for each of the drugs corresponding to a particular illness may be ranked (e.g., from highest to lowest). The drugs and corresponding response scores may be provided in a ranked order on the risk analysis display. In other embodiments, only the highest-ranked drug for a particular illness may be included in the risk analysis display.

In addition to displaying the highest-ranked drug or drugs (and/or other therapies) for a particular illness as a recommendation to the health care provider to prescribe to the patient, the risk analysis display may include a recommended dosage of the drug for the current patient. The risk analysis display may also include any sociomic, physiomic, environmental or demographic information that may lead to a modification of the current patient's response to the drug (e.g., a change in diet, exercise, exposure, etc.). Moreover, the risk analysis display may include recommendations to alter the existing therapies of the current patient by changing dosage, changing drugs, or eliminating a course of therapy the current patient is taking according to his/her polypharmacy data, or other methods. For example, when the recommended drug may render one or several of the drugs redundant in the current patient's polypharmacy data, the risk analysis display may include a recommendation to stop taking those drugs.

In some embodiments, if the patient is taking a drug that is contraindicated with the highest-ranked drug, the pharmacological phenotype assessment server 102 may recommend a drug having a lower response score (or other drug-specific attributes) but a higher compatibility with existing therapies (or other polypharmacy attributes). For example, the pharmacological phenotype assessment server 102 may obtain polypharmacy data for the current patient and compare the drugs within the polypharmacy data to the recommended drug to check for contraindications. The highest-ranked drug that does not have a contraindication with any of the drugs prescribed to the current patient may be included in the risk analysis display.

Pharmacological phenotypes may be predicted in research settings for drug development and insurance applications in addition to clinical settings. In a research setting, pharmacological phenotypes related to novel, experimental, or repurposed drugs may be predicted for potential cohorts of patients in the research program. Patients may be selected for an experimental treatment according to their predicted pharmacological phenotypes related to an experimental drug.

Furthermore, when the current patient's pharmacological phenotype becomes known (e.g., the current patient has certain pharmacological phenotypes after a threshold amount of time, such as one year), the panomic, sociomic, physiomic and environmental, and phenomic data for the current patient may be added to the training data and the statistical model may be updated accordingly.

Figure 6:
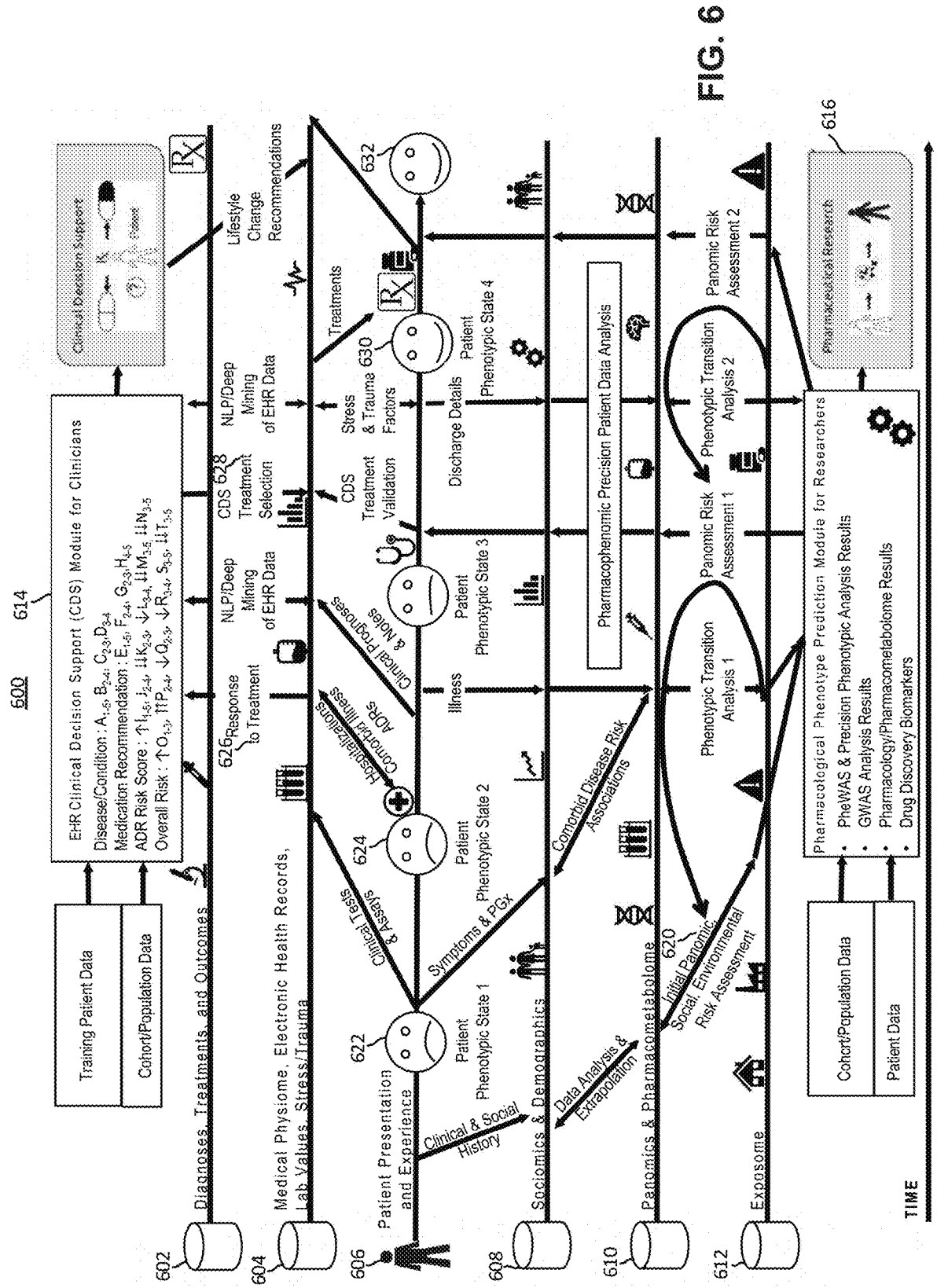
FIG. 6 depicts an example timeline for a patient including example panomic, phenomic, sociomic, physiomic and environmental data collected over time along with pharmacological phenotypes for the patient as determined by the pharmacological phenotype prediction system in accordance with the presently described embodiments.

FIG. 6 illustrates an example timeline 600 for a current patient, where the current patient's panomic, sociomic, physiomic and environmental, and phenomic data are collected over time. The pharmacological phenotype prediction system 100 may then analyze the current patient's collected data according to the statistical model to predict pharmacological phenotypes for the current patient. More specifically, in the example timeline 600 the current patient's diagnoses, treatments, and outcomes 602 are collected. The current patients' medical physiomics, EHRs, laboratory values, stress and abuse factors and trauma 604 are also collected as well as sociomics and demographics 608, panomics and pharmacometabolomics 610, and exposome data 612 for the current patient. Furthermore, the current patient's phenomic data 606 (which may be indicative of the current patient's medical outcomes 602) is also collected.

As mentioned above, the pharmacological phenotype prediction system 100 may include a clinical decision support module for clinicians 614 and a clinical decision support module for researchers 616 in a clinical treatment and/or pharmaceutical or other biomedical research setting.

In the clinical decision support module for clinicians 614, a statistical model is generated in a similar manner as described above based on training data from individual training patients or cohorts/populations of training patients. The current patient's panomic, sociomic, physiomic and environmental, and phenomic data (e.g., diagnoses, treatments, and outcomes 602, medical physiomics, EHRs, laboratory values, stress and abuse factors and trauma 604, phenomic data 606, sociomics and demographics 608, panomics and pharmacometabolomics 610, and exposome data 612) is applied to the statistical model to predict pharmacological phenotypes for the current patient. The pharmacological phenotypes may include a disease risk or condition, a medication recommendation, an adverse drug response score, an overall drug response score, etc. However, these are merely a few examples of pharmacological phenotypes. Additional or alternative pharmacological phenotypes are described throughout.

In the clinical decision support module for researchers 616, a statistical model is generated in a similar manner as described above based on training data from individual patients or cohorts/populations of patients. The patient's panomic, sociomic, physiomic and environmental, and phenomic data is applied to the statistical model to identify GWAS analysis results that describe relationships between cohorts of training patients and particular pharmacological phenotypes, pharmacology/pharmacometabolomic results, precision phenotypic analysis results, biomarkers, etc.

At a first point in time within the timeline 600, panomic, sociomic, physiomic and environmental data is collected from the current patient. The patient's phenotypic state is negative 622 at this time. The current patient then begins to experience symptoms of an illness and is later hospitalized resulting in a further negative phenotypic state 624 at a second point in time. All of this information including the patient's response to treatment 626 as a result of the hospitalization is provided to the clinical decision support module for clinicians 614. The clinical decision support module for clinicians 614 then identifies pharmacological phenotypes for the current patient based on the panomic, sociomic, physiomic and environmental data and provides a treatment selection 628 having the highest predicted response for the current patient, for example. Accordingly, the current patient's phenotypic state transitions from negative 622, 624 to positive 630 and remains positive 632 at a later point in time.

Figure 7:
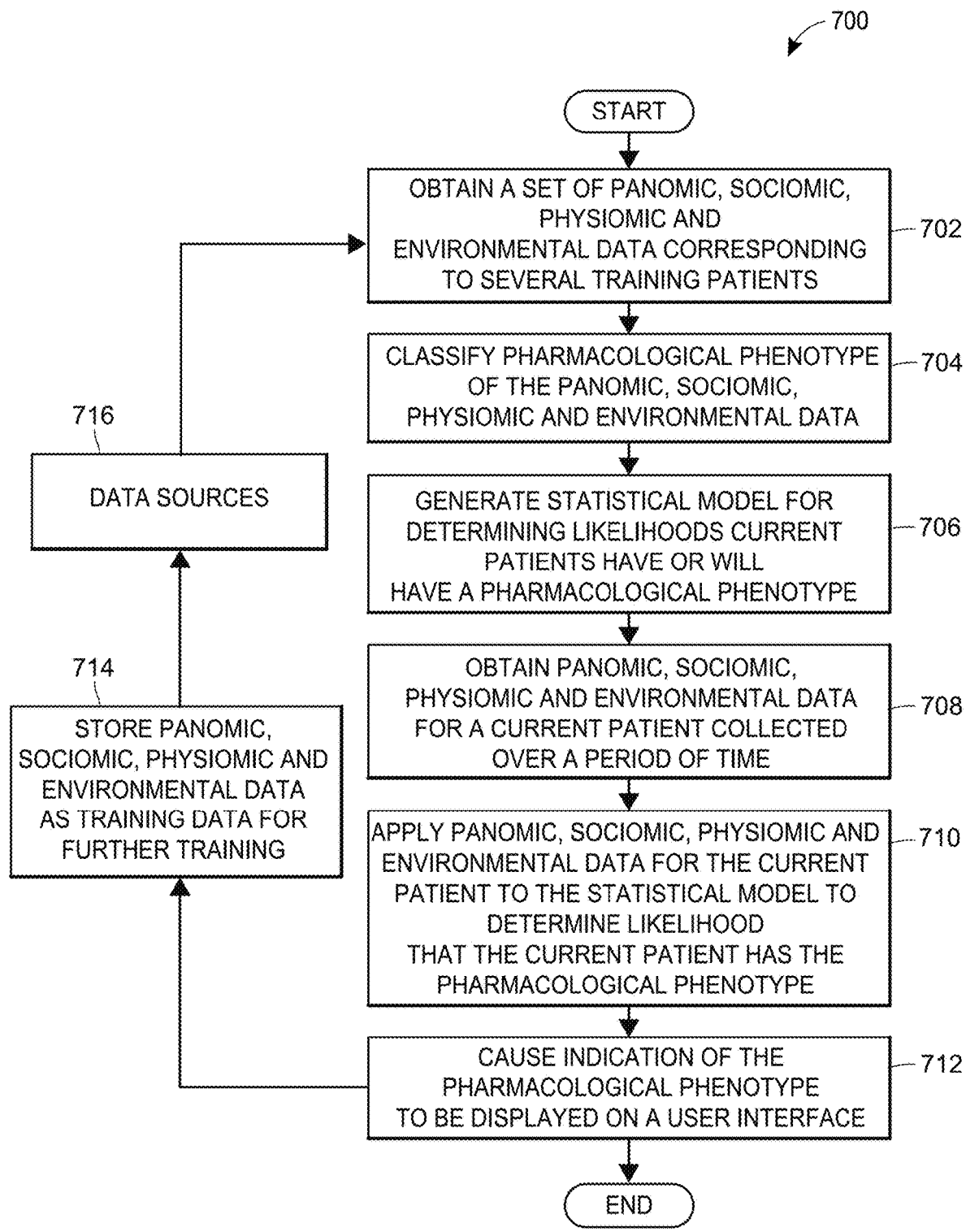
FIG. 7 illustrates a flow diagram representing an exemplary method for identifying pharmacological phenotypes using machine learning techniques in accordance with the presently described embodiments.

FIG. 7 depicts a flow diagram representing an exemplary method 700 for identifying pharmacological phenotypes using machine learning techniques. The method 700 may be executed on the pharmacological phenotype assessment server 102. In some embodiments, the method 700 may be implemented in a set of instructions stored on a non-transitory computer-readable memory and executable on one or more processors on the pharmacological phenotype assessment server 102. For example, the method 700 may be performed by the training module 160 and the phenotype assessment module 162 within the machine learning engine 146 of FIG. 1A.

At block 702, the training module 160 may obtain a set of training data including panomic, sociomic, physiomic and environmental data for training patients where it is known whether the training patients has pharmacological phenotypes (e.g., having currently or previously determined pharmacological phenotypes). Environmental, physiomic and sociomic data may include clinical data, demographic data, polypharmacy data, socioeconomic data, education data, substance abuse data, diet and exercise data, law enforcement data, circadian data, household data, or any other suitable data indicative of a patient's environment. Panomic data may include genomic data indicative of genetic traits, epigenomic data indicative of gene expression, transcriptomic data indicative of DNA transcription, proteomic data indicative of proteins expressed by a genome, choromosomic data indicative of chromatin states in a genome, and/or metabolomic data indicative of metabolites in a genome. As mentioned above, the panomic, sociomic, physiomic and environmental data for training patients may be obtained at several points in time (e.g., over a three year time span).

The sociomic, physiomic and environmental data may be obtained from electronic medical records (EMR) located at an EMR server and/or from polypharmacy data located at a polypharmacy server that aggregates pharmacy data for patients from several pharmacies. Additionally, the sociomic, physiomic and environmental data may be obtained from a training patient's health care provider or self-reported from the training patient. In some embodiments, the training data may be obtained from a combination of sources including several servers (e.g., an EMR server, a polypharmacy server, etc.) and client devices 106-116 of health care providers and patients.

The panomic data may be obtained from client devices 106-116 of health care providers. For example, a health care provider may obtain a biological sample for measuring a patient's panomics (e.g., from saliva, a biopsy, a blood sample, bone marrow, hair, sweat, odor, etc.) and provide laboratory results obtained by analyzing the biological sample to the pharmacological phenotype assessment server 102. In other embodiments, the panomic data may be obtained directly from the laboratory that analyzes the biological sample. In yet other embodiments, the panomic data may be obtained from GWAS or candidate gene association studies that describe a relationship between a cohort of training patients and a particular pharmacological phenotype.

The training module 160 may also obtain phenomic data related to pharmacological phenotypes for the training patients, such as the chronic diseases the training patients suffer from, pharmacological responses to drugs previously prescribed to the training patients, whether each of the training patients suffers from substance abuse problems, etc.

The training module 160 may then classify the panomic, sociomic, physiomic and environmental data according to the pharmacological phenotypes of the training patients associated with the panomic, sociomic, physiomic and environmental data (block 704). The pharmacological phenotypes may include illnesses that at least some of the training patients are diagnosed with, substance abuse problems, pharmacological responses to various drugs, comorbidities, etc. In some scenarios, panomic, sociomic, physiomic and environmental data for the same training patient may be segmented into multiple pharmacological phenotypes at different periods of time. For example, a training patient's panomic data may be altered over time as the environmental data changes for the training patient and at a first time period the training patient may suffer from one mental illness while at a second time period the training patient suffers from another mental or comorbid illness.

Also in some embodiments, the panomic, sociomic, physiomic and environmental data for training patients may be classified according to demographics. For example, panomic, sociomic, physiomic and environmental data for training patients of European ancestry may be assigned to one cohort while panomic, sociomic, physiomic and environmental data for training patients of Chinese ancestry may be assigned to another cohort. In another example, panomic, sociomic, physiomic and environmental data for training patients between the ages of 25 and 35 may be assigned to one cohort while panomic, sociomic, physiomic and environmental data for training patients between the ages of 35 and 45 may be assigned to another cohort.

The panomic, sociomic, physiomic and environmental data for the training patients and their respective pharmacological phenotypes may then be analyzed using various machine learning techniques to generate a statistical model for determining likelihoods or other semi-quantitative and quantitative measures indicating that current patients have various pharmacological phenotypes (block 706). The statistical model may also be used to determine response scores, dosages, or any other suitable indicator of predicted responses that a current patient will have to various drugs.

For example, as described above with reference to FIG. 4B, statistical tests from GWAS or candidate gene association studies indicating a relationship between a cohort of training patients and a particular pharmacological phenotype are analyzed using various machine learning techniques to score and/or rank the variants identified in the studies and/or variants having tight linkage with the identified variants. The highest-ranking variants may be identified as SNPs, genes, and genomic regions correlated or strongly associated with the particular pharmacological phenotype.

For example, for warfarin phenotypes, a warfarin response pathway (as shown in FIG. 4F) may be identified that includes 74 SNPs in 31 genes expressed in the liver, small intestine, and vasculature. The warfarin response pathway includes the genes: AKR1C3 (expressed in the liver), CYP2C19 (expressed in the liver), CYP2C8 (expressed in the liver), CYP2C9 (expressed in the liver), CYP4F2 (expressed in the liver), F5 (expressed in the liver), F7 (expressed in the liver), F10 (expressed in the liver), F11 (expressed in the liver), FGG (expressed in the liver), ORM1 (expressed in the liver), PRSS53 (expressed in the liver), VKORC1 (expressed in the liver), STX4 (expressed in the small intestine), F13A1 (expressed in the vasculature), PROCR (expressed in the vasculature), VWF (expressed in the vasculature), CFHR5 (expressed in the liver), FGA (expressed in the liver), FMO5 (expressed in the liver), HRG (expressed in the liver), KNG1 (expressed in the liver), SURF4 (expressed in the liver), ABO (expressed in the small intestine), LYZ (expressed in the small intestine), PCGF3 (expressed in the small intestine), PRSS8 (expressed in the small intestine), TRPC4AP (expressed in the small intestine), SLC44A2 (expressed in the vasculature), SPHK1 (expressed in the vasculature), and USP7 (expressed in the vasculature). The 74 SNPs included in the 31 genes are: rs12775913 (regulatory SNP), rs346803 (regulatory SNP), rs346797 (regulatory SNP), rs762635 (regulatory SNP), and rs76896860 (regulatory SNP) included in the AKR1C3 gene; rs3758581 (coding SNP) included in the CYP2C19 gene; rs10509681 (coding SNP) and rs11572080 (coding SNP) included in the CYP2C8 gene; rs1057910 (coding SNP), rs1799853 (coding SNP), and rs7900194 (coding SNP) included in the CYP2C9 gene; rs2108622 (coding SNP) included in the CYP4F2 gene; rs6009 (regulatory SNP), rs11441998 (regulatory SNP), rs2026045 (regulatory SNP), rs34580812 (regulatory SNP), rs749767 (regulatory SNP), rs9378928 (regulatory SNP), and rs7937890 (regulatory SNP) included in the F5 gene; rs7552487 (regulatory SNP), rs6681619 (regulatory SNP), rs8102532 (regulatory SNP), rs491098 (coding SNP), and rs6046 (coding SNP) included in the F7 gene; rs11150596 (regulatory SNP) and rs11150596 (regulatory SNP) included in the F10 gene; rs2165743 (regulatory SNP) and rs11252944 (regulatory SNP) included in the F11 gene; rs8050894 (regulatory SNP) included in the FGG gene; rs10982156 (regulatory SNP) included in the ORM1 gene; rs7199949 (coding SNP) included in the PRSS53 gene; rs2884737 (regulatory SNP), rs9934438 (regulatory SNP), rs897984 (regulatory SNP), and rs17708472 (regulatory SNP) included in the VKORC1 gene; rs35675346 (regulatory SNP) and rs33988698 (regulatory SNP) included in the STX4 gene; rs5985 (coding SNP) included in the F13A1 gene; rs867186 (coding SNP) included in the PROCR gene; rs75648520 (regulatory SNP), rs55734215 (regulatory SNP), rs12244584 (regulatory SNP), and rs1063856 (coding SNP) included in the VWF gene; rs674302 (regulatory SNP) included in the CFHR5 gene; rs12928852 (regulatory SNP) and rs6050 (coding SNP) included in the FGA gene; rs8060857 (regulatory SNP) and rs7475662 (regulatory SNP) included in the FMO5 gene; rs9898 (coding SNP) included in the HRG gene; rs710446 (coding SNP) included in the KNG1 gene; rs11577661 (regulatory SNP) included in the SURF4 gene; rs11427024 (regulatory SNP), rs6684766 (regulatory SNP), rs2303222 (regulatory SNP), rs1088838 (regulatory SNP), rs13130318 (regulatory SNP), and rs12951513 (regulatory SNP) included in the ABO gene; rs8118005 (regulatory SNP) included in the LYZ gene; rs76649221 (regulatory SNP), rs9332511 (regulatory SNP), and rs6588133 (regulatory SNP) included in the PCGF3 gene; rs11281612 (regulatory SNP) included in the PRSS8 gene; rs11589005 (regulatory SNP), rs8062719 (regulatory SNP), rs889555 (regulatory SNP), rs36101491 (regulatory SNP), rs7426380 (regulatory SNP), rs6579208 (regulatory SNP), rs77420750 (regulatory SNP), and rs73905041 (coding SNP) included in the TRPC4AP gene; rs3211770 (regulatory SNP), rs3211770 (regulatory SNP), rs3087969 (coding SNP), and rs2288904 (coding SNP) included in the SLC44A2 gene; rs683790 (regulatory SNP) and rs346803 (coding SNP) included in the SPHK1 gene; and rs201033241 (coding SNP) included in the USP7 gene.

In another example, for lithium phenotypes, a lithium response pathway may be identified that includes 78 SNPs in 12 genes expressed in the brain.

Environmental data, sociomic data, physiomic data and phenomic data may be obtained for training patients having a suitable combination of the SNPs, genes, and genomic regions to differentiate training patients having the identified SNPs, genes, and genomic regions who do have the particular pharmacological phenotype from training patients having the identified SNPs, genes, and genomic regions who do not have the particular pharmacological phenotype.

Machine learning techniques including but not limited to regression algorithms (e.g., ordinary least squares regression, linear regression, logistic regression, stepwise regression, multivariate adaptive regression splines, locally estimated scatterplot smoothing, etc.), instance-based algorithms (e.g., k-nearest neighbors, learning vector quantization, self-organizing map, locally weighted learning, etc.), regularization algorithms (e.g., Ridge regression, least absolute shrinkage and selection operator, elastic net, least-angle regression, etc.), decision tree algorithms (e.g., classification and regression tree, iterative dichotomizer 3, C4.5, C5, chi-squared automatic interaction detection, decision stump, M5, conditional decision trees, etc.), clustering algorithms (e.g., k-means, k-medians, expectation maximization, hierarchical clustering, spectral clustering, mean-shift, density-based spatial clustering of applications with noise, ordering points to identify the clustering structure, etc.), association rule learning algorithms (e.g., apriori algorithm, Eclat algorithm, etc.), Bayesian algorithms (e.g., naïve Bayes, Gaussian naïve Bayes, multinomial naïve Bayes, averaged one-dependence estimators, Bayesian belief network, Bayesian network, etc.), artificial neural networks (e.g., perceptron, Hopfield network, radial basis function network, etc.), deep learning algorithms (e.g., multilayer perceptron, deep Boltzmann machine, deep belief network, convolutional neural network, stacked autoencoder, generative adversarial network, etc.), dimensionality reduction algorithms (e.g., principal component analysis, principal component regression, partial least squares regression, Sammon mapping, multidimensional scaling, projection pursuit, linear discriminant analysis, mixture discriminant analysis, quadratic discriminant analysis, flexible discriminant analysis, factor analysis, independent component analysis, non-negative matrix factorization, t-distributed stochastic neighbor embedding, etc.), ensemble algorithms (e.g., boosting, bootstrapped aggregation, AdaBoost, stacked generalization, gradient boosting machines, gradient boosted regression trees, random decision forests, etc.), reinforcement learning (e.g., temporal difference learning, Q-learning, learning automata, State-Action-Reward-State-Action, etc.), support vector machines, mixture models, evolutionary algorithms, probabilistic graphical models, etc. may be used to generate the statistical model for predicting a pharmacological phenotype. For example, the statistical model may be generated based on the identified SNPs, genes, and genomic regions in addition to statistical measures performed on the sociomic, physiomic and environmental data, such as an average income for training patients corresponding to each classification, or sociomic data, such as an average ACE score, etc.

Moreover, the training module 160 may generate several statistical models for several pharmacological phenotypes. For example, a first statistical model may be generated for determining a likelihood that a current patient will experience substance abuse problems, a second statistical model may be generated for determining a risk of suffering from one type of illness, a third statistical model may be generated for determining a risk of suffering from another type of illness, a fourth statistical model may be generated for determining a likelihood of a negative response to a particular drug, etc. In any event, each statistical model may be a graphical model, a decision tree, a probability distribution, or any other suitable model for determining likelihoods that a current patient has certain pharmacological phenotypes or response scores for drugs based on the training data.

At block 708, panomic, sociomic, physiomic and environmental data for a current patient may be obtained. The panomic data may be obtained using a similar process as the process 500 described above with reference to FIG. 5. For example, a patient's biological sample may be obtained by a healthcare provider and sent to an assay laboratory for analysis. Cells are then extracted from the biological sample and reprogrammed into stem cells, such as iPSCs. Then the iPSCs are differentiated into various tissues, such as neurons, cadiomyoctyes, etc., and assayed to obtain panomic data. The panomic data may include genomic data, epigenomic data, transcriptomic data, proteomic data, chromosomic data, metabolomic data, and/or biological networks. In particular, the panomic data may include a quantitative assessment of the patient's current medications by a metabolomics measurement of patient samples.

The sociomic, physiomic and environmental data may be collected at several points in time, for example as in the exposome, sociomics and demographics, and medical physiomics, EHRs, laboratory values, stress and abuse factors and trauma, and medical outcomes data as described above. For example, the sociomic, physiomic and environmental data for the current patient may indicate that the current patient was single and then married in Year 1 and divorced in Year 2. The sociomic, physiomic and environmental data may also indicate that the current patient was employed in Year 1 and then lost his/her job in Year 2. Moreover, the sociomic, physiomic and environmental data may indicate that the current patient was a victim of domestic abuse in Year 1. The longitudinal data may be compared to similar experiences for training patients over similar time periods as indicated in the statistical model.

Then at block 710, the panomic, sociomic, physiomic and environmental data for the current patient may be applied to the statistical model to determine pharmacological phenotypes for the current patient. The pharmacological phenotypes may include likelihoods the current patient has various illnesses or response scores indicative of the current patient's predicted response to various drugs and recommended dosages for the drugs. For example, if the statistical model is a neural network, the phenotype assessment module 162 may traverse the nodes of the neural network using the panomic, sociomic, physiomic and environmental data for the current patient to arrive at various output nodes to determine likelihoods or response scores. If several statistical models are generated, the phenotype assessment module 162 may apply the panomic, sociomic, physiomic and environmental data to each of the statistical models to determine for example, a likelihood or risk of suffering from bipolar disorder, a likelihood or risk of suffering from schizophrenia, a likelihood of having substance abuse problems, a response score for taking lithium to treat bipolar disorder, etc.

For example, the panomic data for the current patient may be analyzed to identify SNPs and genes in the current patient's panomic data that are the same as any of the 74 SNPs or 31 genes in the warfarin response pathway that are correlated with warfarin phenotypes to determine whether the current patient has any of the warfarin phenotypes. Additionally, sociomic, physiomic and environmental data for the current patient may also be applied to a warfarin statistical model to determine warfarin phenotypes for the current patient. The warfarin statistical model may be generated based on the identified 74 SNPs, 31 genes, and warfarin response pathway in addition to statistical measures performed on sociomic, physiomic and environmental data.

In another example, the panomic data for the current patient may be analyzed to identify SNPs and genes in the current patient's panomic data that are the same as any of the 78 SNPs or 12 genes in the lithium response pathway that are correlated with lithium phenotypes to determine whether the current patient has any of the lithium phenotypes. Additionally, sociomic, physiomic and environmental data for the current patient may also be applied to a lithium statistical model to determine lithium phenotypes for the current patient. The lithium statistical model may be generated based on the identified 78 SNPs, 12 genes, and lithium response pathway in addition to statistical measures performed on sociomic, physiomic and environmental data.

At block 712, the phenotype assessment module 162 may cause one or more indications of the pharmacological phenotypes for the current patient to be displayed on a user interface of the health care provider's client device. For example, the phenotype assessment module 162 may generate a risk analysis display that includes indications of each of the likelihoods or other semi-quantitative and quantitative measures of various pharmacological phenotypes which may be represented as a probability (e.g., 0.6), a percentage (e.g., 80 percent), a category from a set of categories (e.g., "High risk," "Medium risk," or "Low risk"), or in any other suitable manner. Additionally, the risk analysis display may include indications of response scores to drugs which may be numerical (e.g., 75 out of 100), categorical (e.g., "Strong response," "Poor response," etc.), or represented in any other suitable manner. Each of the likelihoods or response scores may be displayed with a description of the corresponding pharmacological phenotype (e.g., "High risk of illness Y"). In this manner, the current patient's health care provider may view the indications of pharmacological phenotypes for the current patient and develop an appropriate treatment plan or course of treatment. For example, the health care provider may prescribe a drug to treat a particular illness having the highest response score of the drugs that treat the particular illness.

In some embodiments, the pharmacological phenotype assessment server 102 may compare a likelihood of a pharmacological phenotype to a likelihood threshold (e.g., 0.5) and may include the pharmacological phenotype in the risk analysis display when the likelihood of the pharmacological phenotype exceeds the likelihood threshold. For example, only illnesses that are high risk for the current patient may be included in the risk analysis display. In another example, the risk analysis display may include an indication that the current patient is likely to suffer from substance abuse problems when the likelihood of substance abuse problems for the current patient exceeds a likelihood threshold. In this manner, the health care provider may recommend or provide early intervention to the current patient. Also in some embodiments, response scores for each of the drugs corresponding to a particular illness may be ranked (e.g., from highest to lowest). The drugs and corresponding response scores may be provided in a ranked order on the risk analysis display. In other embodiments, only the highest-ranked drug for a particular illness may be included in the risk analysis display.

In addition to displaying the highest-ranked drug for a particular illness as a recommendation to the health care provider to prescribe to the patient, the risk analysis display may include a recommended dosage of the drug for the current patient. The risk analysis display may also include any sociomic, physiomic, environmental or demographic information that may lead to a modification of the current patient's response to the drug (e.g., a change in diet, exercise, exposure, etc.). Moreover, the risk analysis display may include recommendations to increase or reduce the amount of drugs the current patient is taking according to his/her polypharmacy data. For example, when the recommended drug may render one or several of the drugs redundant in the current patient's polypharmacy data, the risk analysis display may include a recommendation to stop taking those drugs. Such recommendations may involve one or more drugs, combinations thereof, or other therapeutic measures.

In some embodiments, if the patient is taking a drug that is contraindicated with the highest-ranked drug, the pharmacological phenotype assessment server 102 may recommend a drug having the next highest response score. For example, the pharmacological phenotype assessment server 102 may obtain polypharmacy data for the current patient and compare the drugs within the polypharmacy data to the recommended drug to check for contraindications. The highest-ranked drug that does not have a contraindication with any of the drugs prescribed to the current patient may be included in the risk analysis display.

As in the example above related to warfarin, panomic data for the current patient may be compared with the 74 SNPs or 31 genes in the warfarin response pathway that are correlated with warfarin phenotypes to determine whether the current patient has any of the warfarin phenotypes. The pharmacological phenotype assessment server 102 or the health care provider may then determine whether warfarin or another anticoagulant should be administered to the current patient based on the comparison. A recommended dosage for warfarin may also be determined. For example, the current patient may have an SNP or gene in the warfarin response pathway correlated with a negative response to warfarin. Accordingly, the pharmacological phenotype assessment server 102 may recommend another anticoagulant to administer to the current patient. In another example, the current patient may have an SNP or gene in the warfarin response pathway correlated with a warfarin dose phenotype. Accordingly, the pharmacological phenotype assessment server 102 may provide a recommended dosage for administering warfarin to the current patient based on the warfarin dose phenotype. In yet another example, the current patient may have an SNP or gene in the warfarin response pathway correlated with a disease risk, where warfarin can proactively prevent clotting, coagulation, or thrombosis. In any event, the health care provider may administer warfarin to the current patient at the recommended dosage or may administer another anticoagulant.

As in the example above related to lithium, panomic data for the current patient may be compared with the 78 SNPs or 12 genes in the lithium response pathway that are correlated with lithium phenotypes to determine whether the current patient has any of the lithium phenotypes. The pharmacological phenotype assessment server 102 or the health care provider may then determine whether lithium or another psychiatric drug should be administered to the current patient based on the comparison. A recommended dosage for lithium may also be determined. For example, the current patient may have an SNP or gene in the lithium response pathway correlated with a negative response to lithium. Accordingly, the pharmacological phenotype assessment server 102 may recommend another psychiatric drug to administer to the current patient. In another example, the current patient may have an SNP or gene in the lithium response pathway correlated with a lithium dose phenotype.

Accordingly, the pharmacological phenotype assessment server 102 may provide a recommended dosage for administering lithium to the current patient based on the lithium dose phenotype. In any event, the health care provider may administer lithium to the current patient at the recommended dosage or may administer another psychiatric drug.

Pharmacological phenotypes may be predicted in research settings for drug development and insurance applications in addition to clinical settings. In a research setting, pharmacological phenotypes related to experimental drugs may be predicted for potential cohorts of patients in the research program. Patients may be selected for an experimental treatment according to their predicted pharmacological phenotypes related to an experimental drug.

Furthermore, when the current patient's pharmacological phenotype becomes known (e.g., the current patient has the pharmacological phenotypes after a threshold amount of time, such as one year), the panomic, sociomic, physiomic and environmental, and phenomic data for the current patient may be added to the training data (block 714), and the statistical model may be updated accordingly. In some embodiments, the panomic, sociomic, physiomic and environmental, and phenomic data is stored in several data sources 716, such as the data sources 325a-d as described in FIG. 3. The training module 160 may then retrieve data from the data sources 716 to further train the model.

Throughout this specification, plural instances may implement components, operations, or structures described as a single instance. Although individual operations of one or more methods are illustrated and described as separate operations, one or more of the individual operations may be performed concurrently, and nothing requires that the operations be performed in the order illustrated. Structures and functionality presented as separate components in example configurations may be implemented as a combined structure or component. Similarly, structures and functionality presented as a single component may be implemented as separate components. These and other variations, modifications, additions, and improvements fall within the scope of the subject matter herein.

Additionally, certain embodiments are described herein as including logic or a number of routines, subroutines, applications, or instructions. These may constitute either software (e.g., code embodied on a machine-readable medium or in a transmission signal) or hardware. In hardware, the routines, etc., are tangible units capable of performing certain operations and may be configured or arranged in a certain manner. In example embodiments, one or more computer systems (e.g., a standalone, client or server computer system) or one or more hardware modules of a computer system (e.g., a processor or a group of processors) may be configured by software (e.g., an application or application portion) as a hardware module that operates to perform certain operations as described herein.

In various embodiments, a hardware module may be implemented mechanically or electronically. For example, a hardware module may comprise dedicated circuitry or logic that is permanently configured (e.g., as a special-purpose processor, such as a field programmable gate array (FPGA) or an application-specific integrated circuit (ASIC)) to perform certain operations. A hardware module may also comprise programmable logic or circuitry (e.g., as encompassed within a general-purpose processor or other programmable processor) that is temporarily configured by software to perform certain operations. It will be appreciated that the decision to implement a hardware module mechanically, in dedicated and permanently configured circuitry, or in temporarily configured circuitry (e.g., configured by software) may be driven by cost and time considerations.

Accordingly, the term "hardware module" should be understood to encompass a tangible entity, be that an entity that is physically constructed, permanently configured (e.g., hardwired), or temporarily configured (e.g., programmed) to operate in a certain manner or to perform certain operations described herein. Considering embodiments in which hardware modules are temporarily configured (e.g., programmed), each of the hardware modules need not be configured or instantiated at any one instance in time. For example, where the hardware modules comprise a general-purpose processor configured using software, the general-purpose processor may be configured as respective different hardware modules at different times. Software may accordingly configure a processor, for example, to constitute a particular hardware module at one instance of time and to constitute a different hardware module at a different instance of time.

Hardware modules can provide information to, and receive information from, other hardware modules. Accordingly, the described hardware modules may be regarded as being communicatively coupled. Where multiple of such hardware modules exist contemporaneously, communications may be achieved through signal transmission (e.g., over appropriate circuits and buses) that connect the hardware modules. In embodiments in which multiple hardware modules are configured or instantiated at different times, communications between such hardware modules may be achieved, for example, through the storage and retrieval of information in memory structures to which the multiple hardware modules have access. For example, one hardware module may perform an operation and store the output of that operation in a memory device to which it is communicatively coupled. A further hardware module may then, at a later time, access the memory device to retrieve and process the stored output. Hardware modules may also initiate communications with input or output devices, and can operate on a resource (e.g., a collection of information).

The various operations of example methods described herein may be performed, at least partially, by one or more processors that are temporarily configured (e.g., by software) or permanently configured to perform the relevant operations. Whether temporarily or permanently configured, such processors may constitute processor-implemented modules that operate to perform one or more operations or functions. The modules referred to herein may, in some example embodiments, comprise processor-implemented modules.

Similarly, the methods or routines described herein may be at least partially processor-implemented. For example, at least some of the operations of a method may be performed by one or more processors or processor-implemented hardware modules. The performance of certain of the operations may be distributed among the one or more processors, not only residing within a single machine, but deployed across a number of machines. In some example embodiments, the processor or processors may be located in a single location (e.g., within a home environment, an office environment or as a server farm), while in other embodiments the processors may be distributed across a number of locations.

The performance of certain of the operations may be distributed among the one or more processors, not only residing within a single machine, but deployed across a number of machines. In some example embodiments, the one or more processors or processor-implemented modules may be located in a single geographic location (e.g., within a home environment, an office environment, or a server farm). In other example embodiments, the one or more processors or processor-implemented modules may be distributed across a number of geographic locations.

Unless specifically stated otherwise, discussions herein using words such as "processing," "computing," "calculating," "determining," "presenting," "displaying," or the like may refer to actions or processes of a machine (e.g., a computer) that manipulates or transforms data represented as physical (e.g., electronic, magnetic, or optical) quantities within one or more memories (e.g., volatile memory, nonvolatile memory, or a combination thereof), registers, or other machine components that receive, store, transmit, or display information.

As used herein any reference to "one embodiment" or "an embodiment" means that a particular element, feature, structure, or characteristic described in connection with the embodiment is included in at least one embodiment. The appearances of the phrase "in one embodiment" in various places in the specification are not necessarily all referring to the same embodiment.

Some embodiments may be described using the expression "coupled" and "connected" along with their derivatives. For example, some embodiments may be described using the term "coupled" to indicate that two or more elements are in direct physical or electrical contact. The term "coupled," however, may also mean that two or more elements are not in direct contact with each other, but yet still co-operate or interact with each other. The embodiments are not limited in this context.

As used herein, the terms "comprises," "comprising," "includes," "including," "has," "having" or any other variation thereof, are intended to cover a non-exclusive inclusion. For example, a process, method, article, or apparatus that comprises a list of elements is not necessarily limited to only those elements but may include other elements not expressly listed or inherent to such process, method, article, or apparatus. Further, unless expressly stated to the contrary, "or" refers to an inclusive or and not to an exclusive or. For example, a condition A or B is satisfied by any one of the following: A is true (or present) and B is false (or not present), A is false (or not present) and B is true (or present), and both A and B are true (or present).

In addition, use of the "a" or "an" are employed to describe elements and components of the embodiments herein. This is done merely for convenience and to give a general sense of the description. This description, and the claims that follow, should be read to include one or at least one and the singular also includes the plural unless it is obvious that it is meant otherwise.

This detailed description is to be construed as providing examples only and does not describe every possible embodiment, as describing every possible embodiment would be impractical, if not impossible. One could implement numerous alternate embodiments, using either current technology or technology developed after the filing date of this application.

We claim:

1. A computer-implemented method for identifying pharmacological phenotypes, the method executed by one or more processors programmed to perform the method, the method comprising:
   identifying a plurality of single nucleotide polymorphisms (SNPs) correlated with a particular set of pharmacological phenotypes;
   comparing the plurality of SNPs to a database of SNPs to identify additional SNPs that are linked to the plurality of SNPs, wherein the plurality of SNPs and additional SNPs are included in a set of permissive candidate variants;
   performing, by one or more processors, a bioinformatics analysis to filter the set of permissive candidate variants into a subset of intermediate candidate variants based on at least one of: regulatory function, variant dependence, a presence of target gene relationships for the permissive candidate variants, or whether the permissive candidate variants are non-synonymous coding variants with a minor allele frequency;
   performing, by the one or more processors, a network analysis to filter the subset of intermediate candidate variants into candidate variants of SNPs, genes associated with the SNPs, or networks associated with the SNPs which are causally related to the particular set of pharmacological phenotypes;
   obtaining a biological sample of a patient;
   comparing the biological sample to the SNPs which are causally related to the particular set of pharmacological phenotypes; and
   providing, by the one or more processors, an indication of one or more pharmacological phenotypes for the patient for display to a health care provider based on the comparison.

2. The method of claim 1, wherein performing a bioinformatics analysis to filter the set of permissive candidate variants into a subset of intermediate candidate variants includes:
   evaluating, by the one or more processors, genomic regions around the set of permissive candidate variants for regulatory function.

3. The method of claim 2, wherein genomic regions around the set of permissive candidate variants are evaluated for regulatory function to at least one of: (1) determine whether sequence contexts for the set of permissive candidate variants influence the regulatory function, or (2) determine target genes for the set of permissive candidate variants.

4. The method of claim 3, wherein target genes for the set of permissive candidate variants are determined using machine learning techniques.

5. The method of claim 1, wherein performing a bioinformatics analysis to filter the set of permissive candidate variants into a subset of intermediate candidate variants includes:
   scoring, by the one or more processors, each of the permissive candidate variants based on at least one of: regulatory function, variant dependence, a presence of target gene relationships for the permissive candidate variants, or whether the permissive candidate variants are non-synonymous coding variants with a minor allele frequency; and
   assigning, by the one or more processors, one or more of the permissive candidate variants that are scored above a threshold score to the subset of intermediate candidate variants.

6. The method of claim 1, wherein the particular set of pharmacological phenotypes includes a set of warfarin phenotypes, and the identified plurality of SNPs which are causally related to the set of warfarin phenotypes include a warfarin response pathway.

7. The method of claim 1, wherein providing the one or more pharmacological phenotypes for the patient for display to a health care provider includes:
   generating, by the one or more processors, a risk analysis display for the patient including at least one of: a predicted response by the patient to each of one or more drugs, a risk of one or more illnesses, or a likelihood of substance abuse.

8. The method of claim 1, wherein the one or more pharmacological phenotypes include at least one of: a predicted response by second patient to one or more drugs, a risk of one or more illnesses, an adverse drug event or adverse drug reaction to the one or more drugs, or a likelihood of substance abuse.

9. A computing device for identifying pharmacological phenotypes using statistical modeling and machine learning techniques, the computing device comprising:
a communication network,
one or more processors; and
a non-transitory computer-readable memory coupled to the one or more processors and storing thereon instructions that, when executed by the one or more processors, cause the computing device to:
identify a plurality of single nucleotide polymorphisms (SNPs) correlated with a particular set of pharmacological phenotypes;
compare the plurality of SNPs to a database of SNPs to identify additional SNPs that are linked to the plurality of SNPs, wherein the plurality of SNPs and additional SNPs are included in a set of permissive candidate variants;
perform a bioinformatics analysis to filter the set of permissive candidate variants into a subset of intermediate candidate variants based on at least one of: regulatory function, variant dependence, a presence of target gene relationships for the permissive candidate variants, or whether the permissive candidate variants are non-synonymous coding variants with a minor allele frequency;
perform a network analysis to filter the subset of intermediate candidate variants into candidate variants of SNPs, genes associated with the SNPs, or networks associated with the SNPs which are causally related to the particular set of pharmacological phenotypes;
obtain a biological sample of a patient;
compare the biological sample to the SNPs which are causally related to the particular set of pharmacological phenotypes; and
provide, via the communication network, an indication of one or more pharmacological phenotypes for the patient for display to a health care provider based on the comparison.

10. The computing device of claim 9, wherein to perform a bioinformatics analysis to filter the set of permissive candidate variants into a subset of intermediate candidate variants, the instructions cause the computing device to:
evaluate genomic regions around the set of permissive candidate variants for regulatory function.

11. The computing device of claim 10, wherein genomic regions around the set of permissive candidate variants are evaluated for regulatory function to at least one of: (1) determine whether sequence contexts for the set of permissive candidate variants influence the regulatory function, or (2) determine target genes for the set of permissive candidate variants.

12. The computing device of claim 11, wherein target genes for the set of permissive candidate variants are determined using machine learning techniques.

13. The computing device method of claim 9, wherein to perform a bioinformatics analysis to filter the set of permissive candidate variants into a subset of intermediate candidate variants, the instructions cause the computing device to:
score each of the permissive candidate variants based on at least one of: regulatory function, variant dependence, a presence of target gene relationships for the permissive candidate variants, or whether the permissive candidate variants are non-synonymous coding variants with a minor allele frequency; and
assign one or more of the permissive candidate variants that are scored above a threshold score to the subset of intermediate candidate variants.

14. The computing device of claim 9, wherein the particular set of pharmacological phenotypes includes a set of warfarin phenotypes, and the identified plurality of SNPs which are causally related to the set of warfarin phenotypes include a warfarin response pathway.

15. The computing device of claim 9, wherein to provide the one or more pharmacological phenotypes for the patient for display to a health care provider, the instructions cause the computing device to:
generate a risk analysis display for the patient including at least one of: a predicted response by the patient to each of one or more drugs, a risk of one or more illnesses, or a likelihood of substance abuse.

16. A method for treating a patient comprising:
obtaining a biological sample of a patient;
comparing or having compared the biological sample to a set of single nucleotide polymorphisms (SNPs) within a warfarin response pathway having a plurality of SNPs each of which are causally related to warfarin response phenotypes;
determining a dosage of warfarin for administering to the patient based on the comparison; and
administering the determined dosage of warfarin to the patient.

17. The method of claim 16, wherein the one or more SNPs in the warfarin response pathway are identified by:
identifying a plurality of SNPs correlated with warfarin response phenotypes;
comparing the plurality of SNPs to a database of SNPs to identify additional SNPs that are linked to the plurality of SNPs, wherein the plurality of SNPs and additional SNPs are included in a set of permissive candidate variants;
performing a bioinformatics analysis to filter the set of permissive candidate variants into a subset of intermediate candidate variants based on at least one of: regulatory function, variant dependence, a presence of target gene relationships for the permissive candidate variants, or whether the permissive candidate variants are non-synonymous coding variants with a minor allele frequency; and
performing a pathway analysis to filter the subset of intermediate candidate variants into candidate variants of SNPs, genes associated with the SNPs, or pathways associated with the SNPs which are causally related to the warfarin response phenotypes.

18. The method of claim 16, wherein the warfarin response phenotypes include at least one of: a warfarin efficacy phenotype, an adverse warfarin response phenotype, a warfarin dose phenotype, hemostatic factors and hematological phenotypes, hemorrhaging end-stage coagulation, or thrombin generation potential phenotypes.

19. The method of claim 16, further comprising:
comparing or having compared SNPs in the biological sample to the set of SNPs within the warfarin response pathway; and assigning scores to the SNPs in the biological sample that match with the set of SNPs within the warfarin response pathway; and combining the assigned scores to determine the dosage for administering to the patient.

20. The method of claim 16, wherein the warfarin response pathway includes one or more of: complement factor H related 5 (CFHR5) gene, fibrinogen alpha chain gene (FGA) gene, flavin containing monoxygenase 5 (FMO5) gene, histidine rich glycoprotein (HRG) gene, kininogen 1 (KNG1) gene, surfeit 4 (SURF4) gene, alpha 1-3-N-acetylgalactosaminyltransferase and alpha 1-3-galactosyltransferase (ABO) gene, lysozyme (LYZ) gene, polycomb group ring finger 3 (PCGF3) gene, serine protease 8 (PRSS8) gene, transient receptor potential cation channel subfamily C member 4 associated pattern (TRPC4AP) gene, solute carrier family 44 member 2 (SLC44A2) gene, sphingosine kinase 1 (SPHK1) gene, or ubiquitin specific peptidase 7 (USP7) gene.

\* \* \* \* \*